United States Patent
Iba et al.

(10) Patent No.: US 11,479,769 B2
(45) Date of Patent: Oct. 25, 2022

(54) TECHNIQUE FOR TREATING CANCER USING STRUCTURALLY-REINFORCED S-TUD

(71) Applicants: National University Corporation Chiba University, Chiba (JP); GeneDesign, Inc., Ibaraki (JP); NOF Corporation, Tokyo (JP)

(72) Inventors: Hideo Iba, Chiba (JP); Takeshi Haraguchi, Chiba (JP); Hirokazu Nankai, Ibaraki (JP); Hideaki Sato, Ibaraki (JP)

(73) Assignees: National University Corporation Chiba University, Chiba (JP); GeneDesign, Inc., Osaka (JP); NOF Corporation, Tokyo (JP)

( * ) Notice: Subject to any disclaimer, the term of this patent is extended or adjusted under 35 U.S.C. 154(b) by 202 days.

(21) Appl. No.: 16/494,743

(22) PCT Filed: Mar. 16, 2018

(86) PCT No.: PCT/JP2018/010514
§ 371 (c)(1),
(2) Date: Sep. 16, 2019

(87) PCT Pub. No.: WO2018/169063
PCT Pub. Date: Sep. 20, 2018

(65) Prior Publication Data
US 2020/0032262 A1 Jan. 30, 2020

(30) Foreign Application Priority Data

Mar. 17, 2017 (JP) .............................. JP2017-053124

(51) Int. Cl.
*C07H 21/02* (2006.01)
*C07H 21/04* (2006.01)
*C12N 15/113* (2010.01)
*A61P 35/00* (2006.01)
*A61K 9/127* (2006.01)
*A61K 31/713* (2006.01)

(52) U.S. Cl.
CPC ............ *C12N 15/113* (2013.01); *A61K 9/127* (2013.01); *A61K 31/713* (2013.01); *A61P 35/00* (2018.01); *C12N 2310/113* (2013.01); *C12N 2310/3231* (2013.01); *C12N 2320/32* (2013.01)

(58) Field of Classification Search
CPC ...................... C12N 2310/141; C12N 15/113
See application file for complete search history.

(56) References Cited

U.S. PATENT DOCUMENTS

| 2007/0167387 A1 | 7/2007 | Imanishi et al. |
| 2011/0245481 A1 | 10/2011 | Iba et al. |
| 2014/0335157 A1 | 11/2014 | Tange et al. |

FOREIGN PATENT DOCUMENTS

| CA | 2 975 371 A1 | 8/2016 | |
| EP | 1 661 905 A1 | 5/2006 | |
| EP | 2 363 467 A1 | 9/2011 | |
| EP | 2 781 507 A1 | 9/2014 | |
| EP | 3 351 632 A1 | 9/2016 | |
| EP | 3 357 498 A1 | 9/2017 | |
| EP | 3252043 A1 | 12/2017 | |
| WO | 2005/021570 A1 | 3/2005 | |
| WO | 2010/047216 A1 | 4/2010 | |
| WO | WO 2011/126842 A2 * | 10/2011 | ....... C12N 2310/141 |
| WO | 2013/073480 A1 | 5/2013 | |
| WO | WO 2014/134144 A1 * | 9/2014 | ....... C12N 2310/141 |
| WO | 2016/121942 A1 | 8/2016 | |
| WO | 2016/126844 A1 | 8/2016 | |
| WO | 2017/047097 A1 | 3/2017 | |

OTHER PUBLICATIONS

Haraguchi et al., "Dynamics and plasticity of the epithelial to mesenchymal transition induced by miR-200 family inhibition," *Scientific Reports* 6:21117, DOI: 10.1038/srep21117, 2016, 12 pages.
Rahman et al., "Design, Synthesis, and Properties of 2'4'-BNA$^{nc}$: A Bridged Nucleic Acid Analogue,"*J. Am. Chem. Soc.* 130(14):4886-4896, 2008.

* cited by examiner

*Primary Examiner* — Amy H Bowman
(74) *Attorney, Agent, or Firm* — Seed IP Law Group LLP

(57) ABSTRACT

Provided is a novel technique for treating cancer using structurally-reinforced S-TuD. Provided are: a composition for the prevention or treatment of tumors, said composition comprising an miRNA inhibitory complex including RNA of analog thereof; and a method for preventing or treating tumors using said composition. The miRNA inhibitory complex preferably includes at least one double-stranded structure and an miRNA-binding sequence. Two strands of the miRNA binding sequence preferably bind individually to two strands on at least one end of the double-stranded structure. According to some of the aspects of the present invention, there is provided a delivery system for delivering such an miRNA inhibitory complex.

1 Claim, 17 Drawing Sheets

Specification includes a Sequence Listing.

FIG. 4

① S-TuD-141/200c-1_17-pf-S10-BT6-MBSB1 tAGGAUCAUC AGAUUACCAGACAGUGUUAAGA GUAUtCUGGt SEQ ID NO:9
AUCCtAGtAG AGAAUUAUGACGGCCCAUtAAGA CAtAAGACCA SEQ ID NO:10

② S-TuD-NCs-S10-BT6-MBSB1 tAGGAUCAUC AACGtAUGGACGUCGAGCCCAA GUAUtCUGGt SEQ ID NO:11
AUCCtAGtAG AACCCGGAGCUGCAGCUAUGCAA CAtAAGACCA SEQ ID NO:12

FIG. 10

S-TuD200c

㊶ S-TuD-200c-1_22-pf
UACGGCGCUAGGAUCAUC　AACCCAUCAUUACCCGGCAGUAUUACAA　GUAUUCUGGA　SEQ ID NO:18
AUGCCGCGAUCCUAGUAG　　　　　　　　　　　　　　　　　　　　　　CAUAAGACCU　SEQ ID NO:19

㊷ S-TuD-200c-1_22-pf-L18B6
tACGGCGCUAGGAUCAUC　AACCCAUCAUUACCCGGCAGUAUUACAA　GtAUUctGGA　SEQ ID NO:20
AUGCCGCGAtCCUAGtAG　　　　　　　　　　　　　　　　　　　　　　CAUAAGACCt　SEQ ID NO:21
　　　　　　　　　　　AACAUUAUGACGGCCCAUUACUACCCAA

㊸ S-TuD-200c-1_22-pf-L18B6-MBSB1 (complementary sequence to seed region includes BNA)
tACGGCGCUAGGAUCAUC　AACCCAUCAUUACCCGGCAGtAUtACAA　GtAUUctGGA　SEQ ID NO:22
AUGCCGCGAtCCUAGtAG　　　　　　　　　　　　　　　　　　　　　　CAUAAGACCt　SE

Fig. 16-1

S-TuD21

Conventional S-TuD-21

```
                   AACAUCAGUCGGAUAAGCUACAA GUAUUCUGGA  SEQ ID NO:35
UACGGGCGCUAGGAUCAUC
AUGCCCGCGAUCCUAGUAG                                   
                   AACAUCGAAUAGGCUGACUACAA CAUAAGACCU  SEQ ID NO:36
```

Improved S-TuD-21

```
                   AACAtCAgUCGGAUAAGCUACAA GUAUtCUGGt  SEQ ID NO:39
tAGGAUCAUC
AUCCtAGtAG                                   
                   AACAUCGAAUAGGCUgACtACAA CAtAAGACCA  SEQ ID NO:40
```

BNANC(NMe): lower case

TECHNIQUE FOR TREATING CANCER USING STRUCTURALLY-REINFORCED S-TUD

STATEMENT REGARDING SEQUENCE LISTING

The Sequence Listing associated with this application is provided in text format in lieu of a paper copy, and is hereby incorporated by reference into the specification. The name of the text file containing the Sequence Listing is 690219_401USPC_SEQUENCE_LISTING.txt. The text file is 14.0 KB, was created on Nov. 23, 2021, and is being submitted electronically via EFS-Web.

TECHNICAL FIELD

The present invention relates to a novel cancer therapeutic method using a structurally enhanced synthetic Tough Decoy (S-TuD), an associated therapeutic agent and drug delivery medium.

BACKGROUND ART

A microRNA (miRNA) forms a gene regulation network by regulating a large number of target genes and serves a critical role in many biological phenomena including generation. Various inhibitors for inhibiting miRNAs have been developed (WO 2010/047216—Patent Literature 1).

Inhibitory nucleic acids such as S-TuD are used for experimental suppression of miRNAs. Some of the inventors are involved in the development of enhanced inhibitory nucleic acids.

CITATION LIST

Patent Literature

[PTL 1] International Publication No. WO 2010/047216

SUMMARY OF INVENTION

Solution to Problem

The inventors have completed the present invention by finding that an miRNA inhibitory complex comprising an RNA or an analog thereof, by comprising at least one bridged nucleic acid (BNA) (as used herein, complexes comprising an BNA are also referred to as BNA modified inhibitory nucleic acid "S-TuD"), has the inhibitory activity strengthened and biological activity enhanced, such that a disease (e.g., cancer or the like) can be effectively treated. In a specific embodiment, the inventors have found that tumor is effectively suppressed by using a complex comprising at least one bridged nucleic acid (BNA) when inhibiting cancer related miRNA (e.g., miR-200 family). In addition, it was found that the effect is also observed in concurrent inhibition of a plurality of different members of cancer related miR-NAs.

The present invention has found that BNA modified inhibitory nucleic acid "S-TuD" has a reduced size, increased serum stability, and enhanced capability to inhibit microRNAs compared to conventional "S-TuD" to attain a tumor therapeutic method by inhibiting miRNAs. The BNA modified inhibitory nucleic acid "S-TuD" of the invention has expectation to improve the effect compared to conventional S-TuD.

Therefore, one embodiment of the invention among various embodiments provide a composition for preventing or treating tumor, comprising an miRNA inhibiting complex comprising an RNA or an analog thereof and at least one BNA, and a method for preventing or treating a tumor using the same. An miRNA inhibiting complex comprises at least one double-stranded structure and an miRNA binding sequence. Two strands of the miRNA binding sequence are each bound to one of two strands on at least one end of the double-stranded structure. Such a structure increases the serum stability and enhances the capability to inhibit miR-NAs of the miRNA inhibiting complex used in the present invention, which is advantageous in preventing or treating tumor.

For example, the following items are provided in a preferred embodiment of the invention.

(Item A1)

A composition for preventing or treating tumor, comprising an miRNA inhibiting complex comprising an RNA or an analog thereof, wherein the miRNA inhibiting complex comprises at least one double-stranded structure and an miRNA binding sequence, wherein two strands of the miRNA binding sequence are each bound to one of two strands on at least one end of the double-stranded structure, and wherein the miRNA inhibiting complex comprises at least one bridged nucleic acid (BNA).

(Item A2)

The composition of the preceding item, wherein the BNA comprises a BNA that is bridged via at least one atom selected from the group consisting of oxygen and carbon on the position 2' side and via at least one atom selected from the group consisting of carbon and nitrogen and carbon on the position 4' side.

(Item A3)

The composition of any one of the preceding items, wherein the BNA comprises a 2',4' substituted bridged nucleic acid represented by

[Chemical Formula 1]

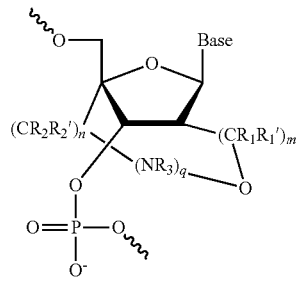

BNA-1 wherein $R_1$, $R_{1'}$, $R_2$, $R_{2'}$, and $R_3$ each independently represent a group selected from the group consisting of a hydrogen atom, a substituted or unsubstituted alkyl group, a substituted or unsubstituted alkenyl group, a substituted or unsubstituted cycloalkyl group, a substituted or unsubstituted aryl group, a substituted or unsubstituted aralkyl group, a substituted or unsubstituted acyl group, a substituted or unsubstituted sulfonyl group, a substituted or unsubstituted silyl group, and a functional molecule unit substituent, m is an integer from 0 to 2, Base represents a group selected from the group consisting of an adeninyl group, a thyminyl group, a uracilyl group, an inosinyl group, a cytosinyl group, a guaninyl group, and a methylcytosinyl group, n is an integer from 1 to 3, and q is an integer that is 0 or 1.
(Item A4)
The composition of any one of the preceding items, wherein the BNA comprises a 2',4' substituted bridged nucleic acid represented by

[Chemical Formula 2]

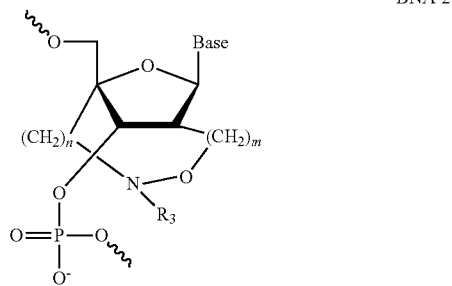

BNA-2 wherein $R_3$ represents a group selected from the group consisting of a hydrogen atom, an alkyl group, an alkenyl group, a cycloalkyl group, an aryl group, an aralkyl group, an acyl group, a sulfonyl group, a silyl group, and a functional molecule unit substituent, Base represents a group selected from the group consisting of an adeninyl group, a thyminyl group, a uracilyl group, an inosinyl group, a cytosinyl group, a guaninyl group, and a methylcytosinyl group, m is an integer from 0 to 2, and n is an integer from 1 to 3.
(Item A5)
The composition of any one of the preceding items, wherein the BNA comprises

[Chemical Formula 3]

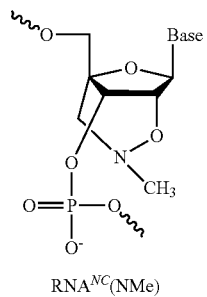

$RNA^{NC}(NMe)$ or a 2',4'-methano bridged nucleic acid (LNA).
(Item A6)
The composition of any one of the preceding items, wherein the BNA is $BNA^{NC}(NMe)$.
(Item A7)
The composition of any one of the preceding items, wherein the miRNA inhibiting complex comprises two or more of the double-stranded structures, wherein strands comprising the miRNA binding sequence are each bound to one of two strands on one end of a first double-stranded structure of the double-stranded structures, and the other ends of the strands are each bound to one of two strands of a second double-stranded structure of the two or more of the double-stranded structures, so that the strands are sandwiched between the two or more of the double-stranded structures.

(Item A8)
The composition of any one of the preceding items, wherein the double-stranded structure is at least 6 bases long.
(Item A9)
The composition of any one of the preceding items, wherein the double-stranded structure is at least 8 bases long.
(Item A10)
The composition of any one of the preceding items, wherein the double-stranded structure is 50 bases long or less.
(Item A11)
The composition of any one of the preceding items, wherein the miRNA inhibiting complex comprises 2 to 5 miRNA binding sequences.
(Item A12)
The composition of any one of the preceding items, wherein the miRNA inhibiting complex comprises two miRNA binding sequences.
(Item A13)
The composition of any one of the preceding items, wherein the miRNA inhibiting complex comprises the structure represented by

[Chemical Formula 4]

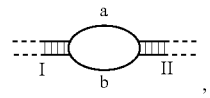

(C)

wherein I and II in the structure are double-stranded structures, and each of a and b of the structure comprises an miRNA binding sequence.
(Item A14)
The composition of any one of the preceding items, wherein the miRNA binding sequence comprises 5'-CAGUGUU-3' (wherein a uracil base is optionally a thymine base), and/or 5'-CAGUAUU-3' (wherein a uracil base is optionally a thymine base).
(Item A15)
The composition of any one of the preceding items, wherein the miRNA inhibiting complex comprises two miRNA binding sequences, one of the miRNA binding sequences comprising 5'-CAGUGUU-3' (wherein a uracil base is optionally a thymine base), and the other miRNA binding sequence comprising 5'-CAGUAUU-3' (wherein a uracil base is optionally a thymine base).
(Item A16)
A nucleic acid molecule, comprising: sequences of 5'-CAGUGUU-3' (wherein a uracil base is optionally a thymine base), and 5'-CAGUAUU-3' (wherein a uracil base is optionally a thymine base); and at least one bridged nucleic acid (BNA).
(Item A16-2)
A nucleic acid molecule comprising: two miRNA binding sequences, one of the miRNA binding sequences comprising 5'-CAGUGUU-3' (wherein a uracil base is optionally a thymine base), or 5'-CAGUAUU-3' (wherein a uracil base is optionally a thymine base), and the other miRNA binding sequence comprising 5'-CAGUGUU-3' (wherein a uracil base is optionally a thymine base), or 5'-CAGUAUU-3' (wherein a uracil base is optionally a thymine base); and at least one bridged nucleic acid (BNA).

(Item A17)
A nucleic acid molecule comprising: two miRNA binding sequences, one of the miRNA binding sequences comprising 5'-CAGUGUU-3' (wherein a uracil base is optionally a thymine base), and the other miRNA binding sequence comprising 5'-CAGUAUU-3' (wherein a uracil base is optionally a thymine base); and at least one bridged nucleic acid (BNA).

(Item A18A)
A nucleic acid molecule comprising an miRNA binding sequence comprising the sequence of SEQ ID NO: 1 (wherein a uracil base is optionally a thymine base), and an miRNA binding sequence comprising the sequence of SEQ ID NO: 2 (wherein a uracil base is optionally a thymine base).

(Item A18B)
A nucleic acid molecule comprising an miRNA binding sequence comprising the sequence of SEQ ID NO: 3 (wherein a uracil base is optionally a thymine base), and an miRNA binding sequence comprising the sequence of SEQ ID NO: 4 (wherein a uracil base is optionally a thymine base).

(Item A19A)
A nucleic acid molecule comprising: the sequence of SEQ ID NO: 9 (wherein a uracil base is optionally a thymine base), and the sequence of SEQ ID NO: 10 (wherein a uracil base is optionally a thymine base); and at least one bridged nucleic acid (BNA).

(Item A19B)
A nucleic acid molecule comprising the sequence of SEQ ID NO: 5 (wherein a uracil base is optionally a thymine base), and the sequence of SEQ ID NO: 6 (wherein a uracil base is optionally a thymine base).

(Item AA1)
A nucleic acid molecule comprising: the sequence of 5'-AUAAGCU-3' (wherein a uracil base is optionally a thymine base); and at least one bridged nucleic acid (BNA).

(Item AA2)
A nucleic acid molecule comprising: an miRNA binding sequence comprising the sequence of SEQ ID NO: 33 (wherein a uracil base is optionally a thymine base); and at least one bridged nucleic acid (BNA).

(Item AA3)
A nucleic acid molecule, comprising an miRNA binding sequence comprising the sequence of SEQ ID NO: 34 (wherein a uracil base is optionally a thymine base).

(Item AA4)
A nucleic acid molecule comprising the sequence of SEQ ID NO: 37 and/or SEQ ID NO: 38.

(Item A20)
A composition comprising the nucleic acid molecule of any one of the preceding items.

(Item A21)
The composition of any one of the preceding items for preventing or treating tumor.

(Item A22)
The composition of any one of the preceding items, wherein the tumor is carcinoma.

(Item A23)
The composition of any one of the preceding items, wherein the tumor is colon cancer, lung cancer, or breast cancer.

(Item A24)
The composition of any one of the preceding items for promoting epithelial-mesenchymal transition of the tumor.

(Item A25)
The composition of any one of the preceding items, wherein the miRNA inhibiting complex or nucleic acid molecule is in a form contained in a carrier for nucleic acid delivery.

(Item A26)
The composition of any one of the preceding items, wherein the carrier is selected from the group consisting of lipid nanoparticles (LNP), a cationic liposome, a non-cationic liposome, a cationic polymer, a non-cationic polymer, β-glucan, an atelocollagen, PLGA nanoparticles, a surfactant peptide, and a super apatite.

(Item A27)
The composition of any one of the preceding items, wherein the carrier is an LNP, the LNP comprising a cationic lipid.

(Item A28)
The composition of any one of the preceding items, wherein the LNP comprises a cationic lipid, a helper lipid, and a PEGylated lipid.

(Item A29) The composition of any one of the preceding items, wherein the cationic lipid comprises a tertiary amine and/or a disulfide bond in a molecule.

(Item B1)
A composition comprising an miRNA inhibiting complex comprising an RNA or an analog thereof and a carrier for nucleic acid delivery, wherein the miRNA inhibiting complex comprises at least one double-stranded structure and an miRNA binding sequence, wherein two strands of the miRNA binding sequence are each bound to one of two strands on at least one end of the double-stranded structure, and the miRNA inhibiting complex comprises at least one bridged nucleic acid (BNA).

(Item B1-1)
The composition of item B1, having a feature of any one of items A1 to A29.

(Item B2)
The composition of any one of the preceding items, which is a pharmaceutical composition.

(Item B3)
The composition of any one of the preceding items for delivering the miRNA inhibiting complex to a desirable site.

(Item B4)
The composition of any one of the preceding items, wherein the BNA comprises a BNA that is bridged via at least one atom selected from the group consisting of oxygen and carbon on the position 2' side and via at least one atom selected from the group consisting of carbon and nitrogen and carbon on the position 4' side.

(Item B5)
The composition of any one of the preceding items, wherein the BNA comprises a 2',4' substituted bridged nucleic acid represented by

[Chemical Formula 5]

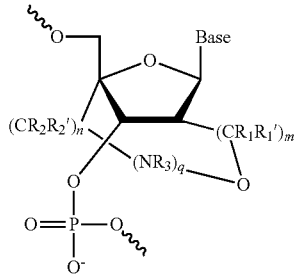

wherein $R_1$, $R_{1'}$, $R_2$, $R_{2'}$, and $R_3$ each independently represent a group selected from the group consisting of a hydrogen atom, a substituted or unsubstituted alkyl group, a substituted or unsubstituted alkenyl group, a substituted or unsubstituted cycloalkyl group, a substituted or unsubstituted aryl group, a substituted or unsubstituted aralkyl group, a substituted or unsubstituted acyl group, a substituted or unsubstituted sulfonyl group, a substituted or unsubstituted silyl group, and a functional molecule unit substituent, m is an integer from 0 to 2, Base represents a group selected from the group consisting of an adeninyl group, a thyminyl group, a uracilyl group, an inosinyl group, a cytosinyl group, a guaninyl group, and a methylcytosinyl group, n is an integer from 1 to 3, and q is integer that is 0 or 1.

(Item B6)

The composition of any one of the preceding items, wherein the BNA comprises a 2',4' substituted bridged nucleic acid represented by

[Chemical Formula 6]

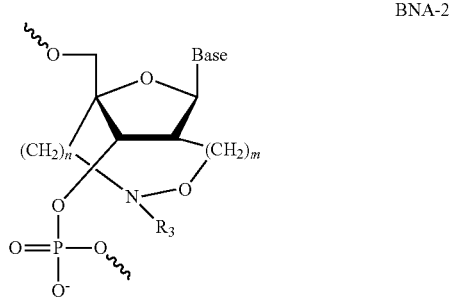

BNA-2 wherein $R_3$ represents a group selected from the group consisting of a hydrogen atom, an alkyl group, an alkenyl group, a cycloalkyl group, an aryl group, an aralkyl group, an acyl group, a sulfonyl group, a silyl group, and a functional molecule unit substituent, Base represents a group selected from the group consisting of an adeninyl group, a thyminyl group, a uracilyl group, an inosinyl group, a cytosinyl group, a guaninyl group, and a methylcytosinyl group, m is an integer from 0 to 2, and n is an integer from 1 to 3.

(Item B7)

The composition of any one of the preceding items, wherein the BNA comprises

[Chemical Formula 7]

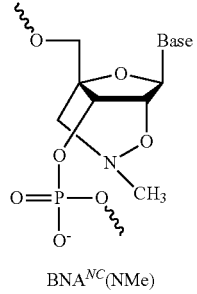

BNA$^{NC}$(NMe)

or a 2',4'-methano bridged nucleic acid (LNA).

(Item B8)

The composition of any one of the preceding items, wherein the BNA is BNA$^{NC}$(NMe).

(Item B9)

The composition of any one of the preceding items, wherein the miRNA inhibiting complex comprises two or more of the double-stranded structures, wherein strands comprising the miRNA binding sequence are each bound to one of two strands on one end of a first double-stranded structure of the double-stranded structures, and the other ends of the strands are each bound to one of two strands of a second double-stranded structure of the two or more of the double-stranded structures, so that the strands are sandwiched between the two or more of the double-stranded structures.

(Item B10)

The composition of any one of the preceding items, wherein the double-stranded structure is at least 6 bases long.

(Item B11)

The composition of any one of the preceding items, wherein the double-stranded structure is at least 8 bases long.

(Item B12)

The composition of any one of the preceding items, wherein the double-stranded structure is 50 bases long or less.

(Item B13)

The composition of any one of the preceding items, wherein the miRNA inhibiting complex comprises 2 to 5 miRNA binding sequences.

(Item B14)

The composition of any one of the preceding items, wherein the miRNA inhibiting complex comprises two miRNA binding sequences.

(Item B15)

The composition of any one of the preceding items, wherein the miRNA inhibiting complex comprises the structure represented by

[Chemical Formula 8]

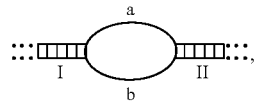

(C)

wherein I and II in the structure are double-stranded structures, and each of a and b of the structure comprises an miRNA binding sequence.

(Item B16)

The composition of any one of the preceding items, wherein the miRNA binding sequence comprises 5'-CAGUGUU-3' (wherein a uracil base is optionally a thymine base), and/or 5'-CAGUAUU-3' (wherein a uracil base is optionally a thymine base).

(Item B17)

The composition of any one of the preceding items, wherein the miRNA inhibiting complex comprises two miRNA binding sequences, one of the miRNA binding sequences comprising 5'-CAGUGUU-3' (wherein a uracil base is optionally a thymine base), and the other miRNA binding sequence comprising 5'-CAGUAUU-3' (wherein a uracil base is optionally a thymine base).

(Item B18A)

The composition of any one of the preceding items, wherein the miRNA inhibiting complex comprises an miRNA binding sequence comprising SEQ ID NO: 1 (wherein a uracil base is optionally a thymine base), and an miRNA binding sequence comprising SEQ ID NO: 2 (wherein a uracil base is optionally a thymine base).

(Item B18B)

The composition of any one of the preceding items, wherein the miRNA inhibiting complex comprises an miRNA binding sequence comprising SEQ ID NO: 3 (wherein a uracil base is optionally a thymine base), and an miRNA binding sequence comprising SEQ ID NO: 4 (wherein a uracil base is optionally a thymine base).

(Item B19A)

The composition of any one of the preceding items, wherein the miRNA inhibiting complex comprises the sequence of SEQ ID NO: 5 (wherein a uracil base is optionally a thymine base), and the sequence of SEQ ID NO: 6 (wherein a uracil base is optionally a thymine base).

(Item B19B)

The composition of any one of the preceding items, wherein the miRNA inhibiting complex comprises the sequence of SEQ ID NO: 9 (wherein a uracil base is optionally a thymine base), and the sequence of SEQ ID NO: 10 (wherein a uracil base is optionally a thymine base).

(Item B20)

The composition of any one of the preceding items, wherein the carrier is selected from the group consisting of lipid nanoparticles (LNP), a cationic liposome, a non-cationic liposome, a cationic polymer, a non-cationic polymer, β-glucan, an atelocollagen, PLGA nanoparticles, a surfactant peptide, and a super apatite.

(Item B21)

The composition of any one of the preceding items, wherein the carrier is an LNP, the LNP comprising a cationic lipid.

(Item B22)

The composition of any one of the preceding items, wherein the LNP comprises a cationic lipid, a helper lipid, and a PEGylated lipid.

(Item B23)

The composition of any one of the preceding items, wherein the cationic lipid comprises a tertiary amine and/or a disulfide bond in a molecule.

(Item C1)

A composition comprising:

a lipid membrane structure comprising, as a constituent lipid of a membrane, a compound represented by formula (1')

[Chemical Formula 9]

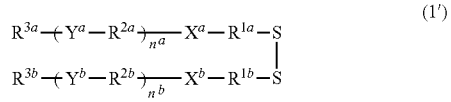

(1')

wherein $X^a$ and $X^b$ are independently a substituent comprising a tertiary amine, s is 1 or 2, $R^4$ represents an alkyl group with 1 to 6 carbons, $n^a$ and $n^b$ are independently 0 or 1, $R^{1a}$ and $R^{1b}$ independently represent an alkylene group with 1 to 6 carbons, $R^{2a}$ and $R^{2b}$ independently represent an alkylene group with 1 to 6 carbons, $Y^a$ and $Y^b$ independently represent an ester bond, an amide bond, a carbamate bond, an ether bond, or a urea bond, $R^{3a}$ and $R^{3b}$ independently represent a sterol residue, a lipophilic vitamin derivative residue, or an aliphatic hydrocarbon group with 12 to 22 carbons, a sterol residue is a cholesteryl group, a cholestaryl group, stigmasteryl group, a β-sitosteryl group, a lanosteryl group, or an ergosteryl group, and a lipophilic vitamin is retinoic acid, retinol, retinal, ergosterol, 7-dehydrocholesterol, calciferol, cholecalciferol, dihydroergocalciferol, dihydrotachysterol, tocopherol, or tocotrienol; and a nucleic acid complex encapsulated by the lipid membrane structure;

wherein the nucleic acid complex is an miRNA inhibiting complex comprising an RNA or an analog thereof, wherein the miRNA inhibiting complex comprises at least one double-stranded structure and an miRNA binding sequence, wherein two strands of the miRNA binding sequence are each bound to one of two strands on at least one end of the double-stranded structure, and wherein the miRNA inhibiting complex comprises at least one bridged nucleic acid (BNA).

(Item C1-1)

The composition of item C1, having the feature of any one of items A1 to A29 and items B1 to B23.

(Item C2)

The composition of any one of the preceding items, wherein $X^a$ and $X^b$ are independently $X^1$, $X^2$, or $X^3$:

[Chemical Formula 10]

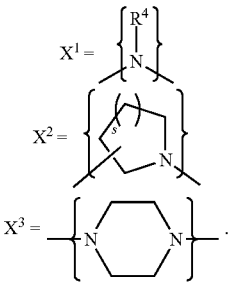

(Item C3)

The composition of any one of the preceding items, wherein $R^{3a}$ and $R^{3b}$ in formula (1') are independently a lipophilic vitamin derivative residue.

(Item C4)

The composition of any one of the preceding items, wherein $Y^a$ and $Y^b$ in formula (1') are independently an ester bond.

(Item C5)

The composition of any one of the preceding items, wherein $n^a$ and $n^b$ in formula (1') are 1.

(Item C6)

The composition of any one of the preceding items, wherein $R^{3a}$ and $R^{3b}$, $Y^a$ and $Y^b$, and/or $X^a$ and $X^b$ in formula (1') are identical.

(Item C7-1)

A composition comprising:

a lipid membrane structure comprising, as a constituent lipid of a membrane, a compound represented by formula (1)

[Chemical Formula 11]

$$R^{3a}-(Y^a-R^{2a})_{n^a}-X^a-R^{1a}-S$$
$$R^{3b}-(Y^b-R^{2b})_{n^b}-X^b-R^{1b}-S$$
(1)

wherein $X^a$ and $X^b$ are independently $X^1$, $X^2$, or $X^3$

[Chemical Formula 12]

$$X^1 = \left\{ \begin{array}{c} R^4 \\ | \\ N \end{array} \right\} \quad X^2 = \left\{ \begin{array}{c} \\ N \end{array} \right\}$$

$$X^3 = \left\{ N \bigcirc N \right\},$$

s is 1 or 2, $R^4$ represents an alkyl group with 1 to 6 carbons, $n^a$ and $n^b$ are independently 0 or 1, $R^{1a}$ and $R^{1b}$ independently represent an alkylene group with 1 to 6 carbons, $R^{2a}$ and $R^{2b}$ independently represent an alkylene group with 1 to 6 carbons, $Y^a$ and $Y^b$ independently represent an ester bond, an amide bond, a carbamate bond, an ether bond, or a urea bond, $R^{3a}$ and $R^{3b}$ independently represent a sterol residue, a lipophilic vitamin derivative residue, or an aliphatic hydrocarbon group with 12 to 22 carbons, a sterol residue is a cholesteryl group, a cholestaryl group, a stigmasteryl group, a β-sitosteryl group, a lanosteryl group, or an ergosteryl group, and a lipophilic vitamin is retinoic acid, retinol, retinal, ergosterol, 7-dehydrocholesterol, calciferol, cholecalciferol, dihydroergocalciferol, dihydrotachysterol, tocopherol, or tocotrienol; and a nucleic acid complex encapsulated by the lipid membrane structure;

wherein the nucleic acid complex is an miRNA inhibiting complex comprising an RNA or an analog thereof, wherein the miRNA inhibiting complex comprises at least one double-stranded structure and an miRNA binding sequence, wherein two strands of the miRNA binding sequence are each bound to one of two strands on at least one end of the double-stranded structure, and wherein the miRNA inhibiting complex comprises at least one bridged nucleic acid (BNA).

(Item C7-2)

A composition comprising:

a lipid membrane structure comprising, as a constituent lipid of a membrane, a compound represented by formula (1)

[Chemical Formula 13]

$$R^{3a}-(Y^a-R^{2a})_{n^a}-X^a-R^{1a}-S$$
$$R^{3b}-(Y^b-R^{2b})_{n^b}-X^b-R^{1b}-S$$
(1)

wherein $X^a$ and $X^b$ are independently $X^1$ or $X^2$,

[Chemical Formula 14]

$$X^1 = \left\{ \begin{array}{c} R^4 \\ | \\ N \end{array} \right\}$$

$$X^2 = \left\{ \begin{array}{c} \\ N \end{array} \right\},$$

s is 1 or 2, $R^4$ represents an alkyl group with 1 to 6 carbons, $n^a$ and $n^b$ are independently 1, $R^{1a}$ and $R^{1b}$ independently represent an alkylene group with 1 to 6 carbons, $R^{2a}$ and $R^{2b}$ independently represent an alkylene group with 1 to 6 carbons, $Y^a$ and $Y^b$ independently represent an ester bond, an amide bond, a carbamate bond, an ether bond, or a urea bond, $R^{3a}$ and $R^{3b}$ independently represent a sterol residue, a lipophilic vitamin derivative residue, or an aliphatic hydrocarbon group with 12 to 22 carbons, a sterol residue is a cholesteryl group, a cholestaryl group, a stigmasteryl group, a β-sitosteryl group, a lanosteryl group, or an ergosteryl group, and a lipophilic vitamin is retinoic acid, retinol, retinal, ergosterol, 7-dehydrocholesterol, calciferol, cholecalciferol, dihydroergocalciferol, dihydrotachysterol, tocopherol, or tocotrienol; and a nucleic acid complex encapsulated by the lipid membrane structure;

wherein the nucleic acid complex is an miRNA inhibiting complex comprising an RNA or an analog thereof, wherein the miRNA inhibiting complex comprises at least one double-stranded structure and an miRNA binding sequence, wherein two strands of the miRNA binding sequence are each bound to one of two strands on at least one end of the double-stranded structure, and wherein the miRNA inhibiting complex comprises at least one bridged nucleic acid (BNA).

(Item C8)

The composition of any one of the preceding items, wherein $X^a$ and $X^b$ are independently $X^2$.

(Item C9)

The composition of any one of the preceding items, wherein $R^{1a}$ and $R^{3b}$ are independently a lipophilic vitamin derivative residue or an aliphatic hydrocarbon group with 12 to 22 carbons.

(Item O10)

The composition of any one of the preceding items, wherein $R^{1a}$ and $R^{3b}$ are independently a lipophilic vitamin derivative residue.

(Item C11)
The composition of any one of the preceding items, wherein the lipophilic vitamin derivative residue is a residue derived from a reactant of a lipophilic vitamin having a hydroxyl group and succinic acid anhydride or a glutaric acid anhydride.

(Item C12)
The composition of any one of the preceding items, wherein $R^{1a}$ and $R^{3b}$ are independently an aliphatic hydrocarbon group with 12 to 22 carbons.

(Item 013)
The composition of any one of the preceding items, comprising:
a lipid membrane structure comprising, as a constituent lipid of a membrane, a compound represented by formula (4)

[Chemical Formula 15]

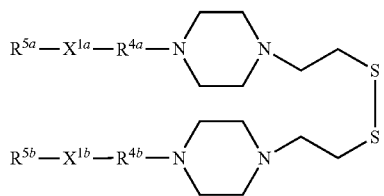

(4)

wherein
$R^{4a}$ and $R^{4b}$ are independently an alkylene group or oxydialkylene group with 8 carbons or less,
$X^{1a}$ and $X^{1b}$ independently represent an ester bond, an amide bond, a carbamate bond, or an ether bond,
$R^{5a}$ and $R^{5b}$ independently represent a sterol residue, a lipophilic vitamin residue, or an aliphatic hydrocarbon group with 13 to 23 carbons,
a sterol residue is a cholesteryl group, a cholestaryl group, a stigmasteryl group, a β-sitosteryl group, a lanosteryl group, or an ergosteryl group, and
a lipophilic vitamin is retinoic acid, retinol, retinal, ergosterol, 7-dehydrocholesterol, calciferol, cholecalciferol, dihydroergocalciferol, dihydrotachysterol, tocopherol, or tocotrienol; and
a nucleic acid complex encapsulated by the lipid membrane structure;
wherein the nucleic acid complex is an miRNA inhibiting complex comprising an RNA or an analog thereof, wherein the miRNA inhibiting complex comprises at least one double-stranded structure and an miRNA binding sequence, wherein two strands of the miRNA binding sequence are each bound to one of two strands on at least one end of the double-stranded structure, and wherein the miRNA inhibiting complex comprises at least one bridged nucleic acid (BNA).

(Item C15)
The composition of any one of the preceding items, wherein $R^{4a}$ and $R^{4b}$ in formula (4) are independently an alkylene group with 8 carbons or less.

(Item C16)
The composition of any one of the preceding items, wherein $X^{1a}$ and $X^{1b}$ in formula (4) are ester bonds.

(Item C17)
The composition of any one of the preceding items, wherein $R^{5a}$ and $R^{5b}$ in formula (4) are independently a lipophilic vitamin residue or an aliphatic hydrocarbon group with 13 to 23 carbons.

(Item C18)
The composition of any one of the preceding items, wherein $R^{5a}$ and $R^{5b}$ in formula (4) are independently a lipophilic vitamin residue.

(Item C19)
The composition of any one of the preceding items, wherein $R^{5a}$ and $R^{5b}$ in formula (4) are independently an aliphatic hydrocarbon group with 13 to 23 carbons.

(Item C20)
The composition of any one of the preceding items, wherein the BNA is $BNA^{NC}$(NMe).

(Item C21)
The composition of any one of the preceding items, wherein the miRNA inhibiting complex comprises two or more of the double-stranded structures, wherein strands comprising the miRNA binding sequence are each bound to one of two strands on one end of a first double-stranded structure of the double-stranded structures, and the other ends of the strands are each bound to one of two strands of a second double-stranded structure of the two or more of the double-stranded structures, so that the strands are sandwiched between the two or more of the double-stranded structures.

(Item C22)
The composition of any one of the preceding items, wherein the miRNA inhibiting complex comprises two miRNA binding sequences.

(Item C23)
The composition of any one of the preceding items, wherein the miRNA inhibiting complex comprises the structure represented by

[Chemical Formula 16]

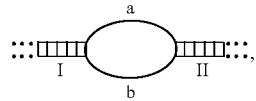

(C)

wherein I and II in the structure are double-stranded structures, and each of a and b of the structure comprises an miRNA binding sequence.

(Item C24)
The composition of any one of the preceding items, wherein the miRNA binding sequence comprises 5'-CAGUGUU-3' (wherein a uracil base is optionally a thymine base), and/or 5'-CAGUAUU-3' (wherein a uracil base is optionally a thymine base).

(Item C25)
The composition of any one of the preceding items, wherein the miRNA inhibiting complex comprises two miRNA binding sequences, one of the miRNA binding sequences comprising 5'-CAGUGUU-3' (wherein a uracil base is optionally a thymine base), and the other miRNA binding sequence comprising 5'-CAGUAUU-3' (wherein a uracil base is optionally a thymine base).

(Item C26A)
The composition of any one of the preceding items, wherein the miRNA inhibiting complex comprises an miRNA binding sequence comprising the sequence of SEQ ID NO: 1 (wherein a uracil base is optionally a thymine base), and an miRNA binding sequence comprising the sequence of SEQ ID NO: 2 (wherein a uracil base is optionally a thymine base).

(Item C26B)

The composition of any one of the preceding items, wherein the miRNA inhibiting complex comprises an miRNA binding sequence comprising the sequence of SEQ ID NO: 3 (wherein a uracil base is optionally a thymine base), and an miRNA binding sequence comprising the sequence of SEQ ID NO: 4 (wherein a uracil base is optionally a thymine base).

(Item C27A)

The composition of any one of the preceding items, wherein the miRNA inhibiting complex comprises the sequence of SEQ ID NO: 5 (wherein a uracil base is optionally a thymine base), and the sequence of SEQ ID NO: 6 (wherein a uracil base is optionally a thymine base).

(Item C27B)

The composition of any one of the preceding items, wherein the miRNA inhibiting complex comprises the sequence of SEQ ID NO: 9 (wherein a uracil base is optionally a thymine base), and the sequence of SEQ ID NO: 10 (wherein a uracil base is optionally a thymine base).

(Item D1)

An miRNA inhibiting complex comprising an RNA or an analog thereof for use in treating or preventing tumor, wherein the miRNA inhibiting complex comprises at least one double-stranded structure and an miRNA binding sequence, wherein two strands of the miRNA binding sequence are each bound to one of two strands on at least one end of the double-stranded structure, and wherein the miRNA inhibiting complex comprises at least one bridged nucleic acid (BNA).

(Item D2)

An miRNA inhibiting complex for the use of any one of the preceding items, further having the feature of any one or more of the preceding items.

(Item E1)

A method of preventing or treating tumor in a subject, comprising administering to the subject an effective amount of the compound, miRNA inhibiting complex, or nucleic acid molecule of any one of the preceding items.

(Item E2)

The method of any one of the preceding items, further having the feature of any one or more of the preceding items.

(Item F1)

Use of an miRNA inhibiting complex comprising an RNA or an analog thereof for use in treating or preventing tumor, wherein the miRNA inhibiting complex comprises at least one double-stranded structure and an miRNA binding sequence, wherein two strands of the miRNA binding sequence are each bound to one of two strands on at least one end of the double-stranded structure, and wherein the miRNA inhibiting complex comprises at least one bridged nucleic acid (BNA).

(Item F2)

The use of any one of the preceding items, further having the feature of any one or more of the preceding items.

In each of the above items, inventions combining any two or more inventions described in each item that is dependent from the same item are already intended in the invention described in a superordinate item from which they are dependent. The present specification is intended for any inventive element described herein and any combination thereof. The present specification is also intended for the above inventions, which exclude any element described herein or any combination thereof. When a specific embodiment is described herein as a preferred embodiment, the present specification discloses not only such an embodiment, but also inventions that exclude such an embodiment from a more superordinate invention disclosed herein including such an embodiment.

Advantageous Effects of Invention

The improved S-TuD of the invention has the miRNA inhibitory activity strengthened compared to conventional S-TUD. Prevention and treatment of tumor can be materialized with such an improved S-TuD by inhibiting an miRNA such as the miR-200 family.

BRIEF DESCRIPTION OF DRAWINGS

FIG. 4 depicts the structures of (1) S-TuD-141/200c-1_17-pf-S10-BT6-MBSB1 (having an MBS for miR-141 and miR-200c) and (2) S-TuD-NCs-S10-BT6-MBSB1-s (MBS is not complementary to miR). Lower case letters in the sequence indicate the location substituted with $BNA^{NC}$ (NMe).

FIG. 10 shows the structures of various S-TuD for miR-200c, which are, from the top, (41) S-TuD-200c-1_22-pf, (42) S-TuD-200c-1_22-pf-L18B6, (43) S-TuD-200c-1_22-pf-L18B6-MBSB1 (complementary sequence of seed region with $BNA^{NC}$(NMe) modification), (44) S-TuD-200c-1_22-pf-L18B6-MBSB2 (complementary sequence of non-seed region with $BNA^{NC}$(NMe) modification), and (45) S-TuD- 200c-1_22-pf-S10-BT6-MBSB2 (complementary sequence of non-seed region with BNA$^{NC}$(NMe) modification)

FIG. 15 shows sequence information of psiCHECK2-T21-5p-s, psiCHECK2-T21-5p-a, psiCHECK2-T200c-3p-s, and psiCHECK2-T200c-3p-a used in the production of a luciferase reporter vector. All of the sequences are unmodified DNAs.

FIG. 16-1 shows the structure of oligo that was used.

FIG. 16-2 shows results of a reporter assay for miR-21 using the oligo in FIG. 16-1. The left side shows results for 300 pM, and the right side shows results for 1000 pM. The bars indicate the ratio of control reporter activity to miR-21 reporter inhibitory activity. The bars are higher for higher miR-21 inhibitory effects.

FIG. 17-1 shows the structure of oligo that was used.

FIG. 17-2 shows results of a reporter assay for miR-200c using the oligo in FIG. 17-1. The left side shows results for 10 pM, and the right side shows results for 100 pM. The bars indicate the ratio of control reporter activity to miR-200c reporter inhibitory activity. The bars are higher for higher miR-200c inhibitory effects.

FIG. 17-3 shows results of a reporter assay for miR-200c. The results with H358 cells introduced with TuD-141/200c expression lentiviral vector are shown. The bars indicate the ratio of control reporter activity to miR-200c reporter inhibitory activity. The bars are higher for higher miR-200c inhibitory effects.

DESCRIPTION OF EMBODIMENTS

Figure 1:
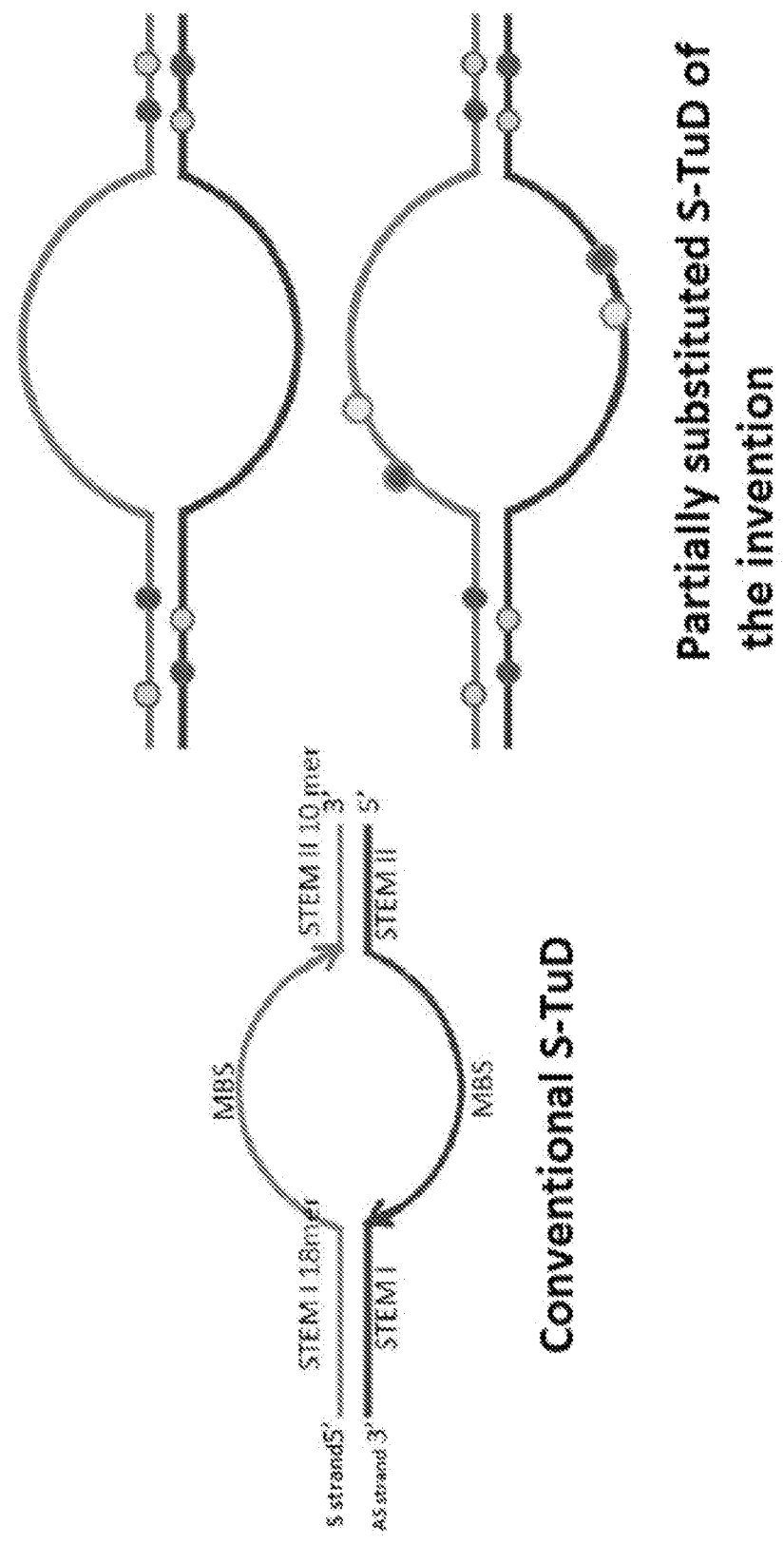
FIG. 1 depicts a schematic diagram of a conventional S-TuD and a partially substituted S-TuD of the invention.

The present invention is described hereinafter. Throughout the entire specification, a singular expression should be understood as encompassing the concept thereof in plural form, unless specifically noted otherwise. Thus, singular articles (e.g., "a", "an", "the", and the like in the case of English) should also be understood as encompassing the concept thereof in plural form, unless specifically noted otherwise. Further, the terms used herein should be understood to be used in the meaning that is commonly used in the art, unless specifically noted otherwise. Thus, unless defined otherwise, all terminologies and scientific technical terms that are used herein have the same meaning as the general understanding of those skilled in the art to which the present invention pertains. In case of a contradiction, the present specification (including the definitions) takes precedence.

<miRNA Inhibiting Complex>

The present invention has found that the miRNA inhibiting complex described in detail below can be used for preventing or treating various diseases, especially treating or preventing tumor, as a medicament. Some of the embodiments of the invention provide a composition comprising the miRNA inhibiting complex described in detail below for treating or preventing tumor.

The present invention also provides a composition comprising the miRNA inhibiting complex described in detail below and a carrier for nucleic acid delivery. The miRNA inhibiting complex described herein can be delivered more suitably to a target by combining such a carrier for nucleic acid delivery.

The improved miRNA inhibiting complex used herein can efficiently and specifically inhibit miRNAs. PCT/JP2016/004252 can be referred for details, which is incorporated herein by reference. The miRNA inhibiting complex used herein is characterized by comprising at least one double-stranded structure, at least one strand comprising an miRNA binding sequence (MBS) binding to two strands on at least one end of the double-stranded structure, and comprising at least one bridged nucleic acid (BNA). The inhibiting complex used in the present invention is also known as "S-TuD". In the present invention, a double-stranded structure is also referred to as a "first" double-stranded structure so that the structure can be distinguished from another double-stranded structure that can be comprised in the complex used herein. The complex used herein may or may not be single stranded (i.e., single molecule bound by a covalent bond). For example, the complex may be comprised of a single strand, double strand, or more strands. For example, any complex consisting of a double-stranded RNA with RNA strands comprising an MBS each bound to one of two strands on one end of a double-stranded structure, as long as the complex comprises at least one bridged nucleic acid (BNA, such as BNA$^{NC}$(NMe)), is encompassed in the scope of complex used in the present invention. For example, a single RNA strand comprising at least one MBS can be bound to two strands on one end of a double-stranded structure. In such a case, two strands on one end of a double-stranded structure would be linked by an RNA strand comprising an MBS. An RNA linking two strands of a double-stranded structure comprises at least one MBS, but for example two, three, or more MBSes can be comprised. A double-stranded structure comprises a stem loop or a hairpin. In other words, a double-stranded structure can be a double-stranded structure comprised in a stem loop or a hairpin. Since an improved miRNA inhibiting complex has high inhibition efficiency and serum stability, the effect of suppressing tumor in vivo can be expected to be improved.

As used herein, "non-seed" region refers to bases other than the 2nd to 8th bases from the 5' end of miRNA required for the activity of the miRNA in the sequence of the miRNA, specifically the 9th to 21st bases from the 5' end of the miRNA. The "non-seed binding region" in the complex used in the present invention refers to a sequence that binds with high complementarity to the non-seed region of an miRNA in the MBS, and "stem region" refers to a double-stranded structure. The comprised BNA may or may not be comprised in a non-seed binding region, and may or may not be comprised in a stem region (see FIG. 1). The biological activity enhancing effect and the like found in the present invention is confirmed for complexes comprising a BNA in a non-seed binding region and stem region. It is understood that the activity is similarly enhanced in accordance with the comprised BNA, even if the BNA is comprised only in a non-seed binding region or only in a stem region.

The miRNA inhibiting complex used in the present invention can be a structure with a double-stranded structure, comprising at least one RNA or an analog thereof. The complex preferably comprises one or two molecules comprising an RNA or an analog thereof.

In the present invention, an "miRNA binding sequence (MBS)" refers to a sequence binding to an miRNA. An MBS comprises at least a moiety that is complementary to an miRNA so that the MBS can bind to the miRNA. As shown in Japanese Patent No. 4936343, an MBS may or may not be a sequence that is fully complementary to an miRNA. For example, an MBS may be a sequence of a naturally-occurring RNA targeted by an miRNA. For example, an MBS comprises at least 10, such as 11 bases or more, 12 bases or more, 13 bases or more, 14 bases or more, 15 bases or more, 16 bases or more, 17 bases or more, 18 bases or more, 19 bases or more, 20 bases or more, 21 bases or more, 22 bases or more, 23 bases or more, or 24 bases or more contiguous or non-contiguous bases that are complementary to an miRNA. The complementary bases are contiguous, or have a gap at three positions or less, two positions or less, and preferably one position. The gaps may be unpaired (bulges) on the MBS side and/or the miRNA side. Gaps at one position may have a bulge base on only one of the strands, or unpaired bases on both strands. They can be designed to include unpaired bases on at least the MBS side. The number of bases in a single bulge or mismatch is, for example, six bases or less, preferably five bases or less, four bases or less, three bases or less, two bases or less, or one base on a single strand for each bulge of mismatch at one position. An MBS that can form a bulge exhibits a higher miRNA inhibiting effect than an MBS consisting of a fully complementary sequence in some cases. Thus, an MBS can be designed to form a bulge to attain higher miRNA inhibiting effects. For example, the following MBSes are not readily degraded so that they can be expected to have high activity: MBSes in which 10th and/or 11th base from the 3' end of the MBS are not complementary to an miRNA, or MBSes comprising extra bases between 10th and 11th bases (or MBSes in which the 10th and/or 11th base from the 5' end of a target sequence in an miRNA (a sequence that hybridizes with an MBS) are not complementary to the MBS, or MBSes comprising unpaired bases between the 10th and 11th bases). However, there is no need to comprise a bulge if a modified base with high resistance to degradation is used. In such a case, an MBS may be designed so that, for example, bases including the 10th and 11th bases from the 5' end of an miRNA are unpaired. For example, an MBS may be designed so that 9th to 11th, 10th to 12th, or 9th to 12th bases are unpaired. Alternatively, an MBS may be designed so that there is no unpaired base on the miRNA side, but the MBS has an unpaired base between 10th and 11th bases from the 3' end on the MBS side (or between sites corresponding to the 10th and 11th bases from the 5' end of a target sequence (sequence that hybridizes with the MBS) in an miRNA). Unpaired bases may be present on the miRNA side and/or the MBS side, but are preferably at least on the MBS side. The number of unpaired nucleotides in each strand can be appropriately adjusted. For example, it is one to six nucleotides, preferably one to five nucleotides, or more preferably three to five nucleotides, such as three, four, or five nucleotides. It is known that a match in the 2nd to 8th bases from the 5' end ("seed region") of an miRNA is important for target recognition by the miRNA (Jackson A L et al., RNA 12(7): 1179-1187, 2006; Lewis B P et al., Cell 120: 15-20, 2005; Brennecke et al. PLoS BIOLOGY 3, 0404-0418, 2005; Lewis et al. Cell 115, 787-798, 2003; Kiriakidou et al. Genes & Development 18, 1165-1178, 2004). In fact, the miRNA-inhibiting RNAs used herein having an MBS that matches only in the seed region and thus has low complementarity with other regions can effectively inhibit miRNAs. In the present invention, an MBS is preferably a sequence of which an miRNA seed region (2nd to 8th bases from the 5' end of an miRNA) is fully complementary thereto. In this case, a G:U pair (U:G pair) may be considered as complementary, but it is preferable to consider only G:C (C:G) and A:U (U:A) pairs as complementary. In the present invention, an MBS is preferably fully complementary to an miRNA seed region (2nd to 8th bases from the 5' end of an miRNA), and comprises at least eight, more preferably nine, and more preferably ten contiguous bases that are complementary to the miRNA. Furthermore, an MBS of the present invention preferably comprises a total of 11 or more bases, more preferably 12 or more bases, and more preferably 13 or more bases that are complementary to an miRNA.

Preferably, an MBS is a sequence that hybridizes with an miRNA sequence under physiological conditions. Physiological conditions are, for example, 150 mM NaCl and 15 mM sodium citrate at pH 7.0 and 37° C. More preferably, an MBS is a sequence that hybridizes with an miRNA sequence under stringent conditions. Stringent conditions are, for example, conditions under 1×SSC ("1×SSC" means 150 mM NaCl and 15 mM sodium citrate at pH 7.0) or 0.5×SSC at 42° C., more preferably conditions under 1×SSC or 0.5×SSC at 45° C., and more preferably conditions under 1×SSC or 0.5×SSC at 50° C. In hybridization, for example, one of an miRNA sequence-comprising RNA and an MBS-comprising RNA is labeled, and the other is immobilized to a membrane to hybridize the two. Hybridization may be carried out under conditions such as in a solution containing 5×SSC, 7% (W/V) SDS, 100 μg/ml denatured salmon sperm DNA, and 5×Denhardt's solution (1×Denhardt's solution contains 0.2% polyvinyl pyrrolidone, 0.2% bovine serum albumin, and 0.2% Ficoll), at for example 37° C., 45° C., or 50° C. After incubation for a sufficient time (e.g., three, four, five, or six hours or more) and then washing under the above conditions, it is possible to detect whether the labeled nucleic acid is hybridized to determine whether a nucleic acid hybridizes under said conditions.

Alternatively, an MBS preferably exhibits high homology to the complementary sequence of an miRNA sequence. Examples of "high homology" include a nucleotide sequence with 70% or greater, 75% or greater, 76% or greater, 77% or greater, 78% or greater, 79% or greater, 80% or greater, 81% or greater, 82% or greater, 83% or greater, 84% or greater, 85% or greater, 86% or greater, 87% or greater, 88% or greater, 89% or greater, 90% or greater, 93% or greater, 95% or greater, 96% or greater, 97% or greater, 98% or greater, or 99% or greater identity. The base sequence identity can be determined using, for example, the BLAST program (Altschul, S. F. et al., J. Mol. Biol. 215: 403-410, 1990). This can be searched using default parameters, for example, on the BLAST web page of the NCBI (National Center for Biotechnology Information) (Altschul S. F. et al., Nature Genet. 3:266-272, 1993; Madden, T. L. et al., Meth. Enzymol. 266:131-141, 1996; Altschul S. F. et al., Nucleic Acids Res. 25:3389-3402, 1997; Zhang J. & Madden T. L., Genome Res. 7:649-656, 1997). For example, the sequence identity can be determined by creating an alignment of two sequences with the blast 2 sequences program (Tatiana A et al., FEMS Microbiol. Lett. 174:247-250, 1999) which compares two sequences. Gaps outside of an miRNA base sequence are ignored, and inner gaps are treated, for example, in the same manner as mismatches to calculate the value of identity to the entire miRNA base sequence (total base length determined by adding the gaps inside the sequence) in alignment. However, as shown in Japanese Patent No. 4936343, a mismatch between an MBS and an miRNA can elevate the miRNA inhibiting activity. Thus, it is preferable, for example, to calculate the identity by ignoring gaps inserted into an miRNA sequence inside the alignment.

Alternatively, an MBS can consist of a sequence with one or several base insertions, substitutions, and/or deletions with respect to a sequence complementary to an miRNA sequence. An MBS can consist of a sequence that has eight or less, seven or less, six or less, five or less, four or less, three or less, two or less, or one base insertion, substitution, and/or deletion with respect to a sequence complementary to an miRNA sequence. Alternatively, an MBS can consist of a sequence that has eight or less, seven or less, six or less, five or less, four or less, three or less, two or less, or one base insertion with respect to a sequence complementary to an miRNA sequence. An MBS with a mismatch has higher miRNA inhibiting activity than an MBS with a sequence that is fully complementary to an miRNA sequence in some cases. It is understood that this is because an MBS that is fully complementary to an miRNA may be cleaved by an RISC comprising an miRNA, thus decreasing the expression level of the miRNA inhibiting RNA. However, it is not necessary to comprise a bulge if a modified base with high resistance to degradation is used. In particular, high activity can be expected from an MBS designed to have the 10th and/or 11th base from the 3' end of the MBS unpaired (or the 10th and/or 11th base from the 5' end of a target sequence in an miRNA that hybridizes with an MBS is unpaired when hybridized with the MBS), or to comprise unpaired bases between the 10th and 11th bases, when the MBS is hybridized with the miRNA. Such unpairing may be, for example, a bulge on the MBS side. The number of bases forming a bulge is one to six bases, preferably one to five bases, and more preferably three to five bases (e.g., three, four, or five bases). An MBS may consist of an RNA, comprise a nucleic acid analog, or consist of a nucleic acid analog. In particular, the miRNA inhibiting effect is expected to be elevated by converting a site cleaved in an MBS (10th and/or 11th base from the 3' end of the MBS, etc.) into a nucleic acid analog in order to prevent cleavage. It is also favorable to use nucleic acids that have a sugar or a backbone such as phosphorothioate or 2"-O-methyl (Krutzfeldt, J. et al., Nucleic Acids Res. 35: 2885-2892; Davis, S. et al., 2006, Nucleic Acids Res. 34: 2294-2304)

There are no particular limitations on miRNAs targeted by the miRNA inhibiting complexes used herein. miRNAs derived from any species of plants, nematodes, and vertebrates may be targeted, as long as they have an miRNA structure. A very large number of miRNA sequences are known in various organisms, including humans, mice, chickens, zebrafish, and *Arabidopsis thaliana* (see the webpage of miR Base::Sequences: microrna.sanger.ac.uk/sequences/). For example, miRNAs of mammals including mice, rats, goats, and the like, primates including monkeys, and humans can be targeted. Examples thereof include miRNAs in the miR-200 family (e.g., miR-200a, miR-200b, miR-200c, miR-141, and miR-429), preferably miR-200c, miR-141, and the like. Examples of miRNAs that can be targeted include miR-21, miRNAs of the miR-17-92 cluster (e.g., miR-17, miR-18a, miR-19a, miR-20a, miR-19b-1, miR-92a-1), miR-155, miR-133a, miR-196b, miR-197, miR-205, miR-125b, miR-135b, miR-106a, miR-10a/10b, miR-146a, miR-182, miR-96, and the like.

Figure 2:
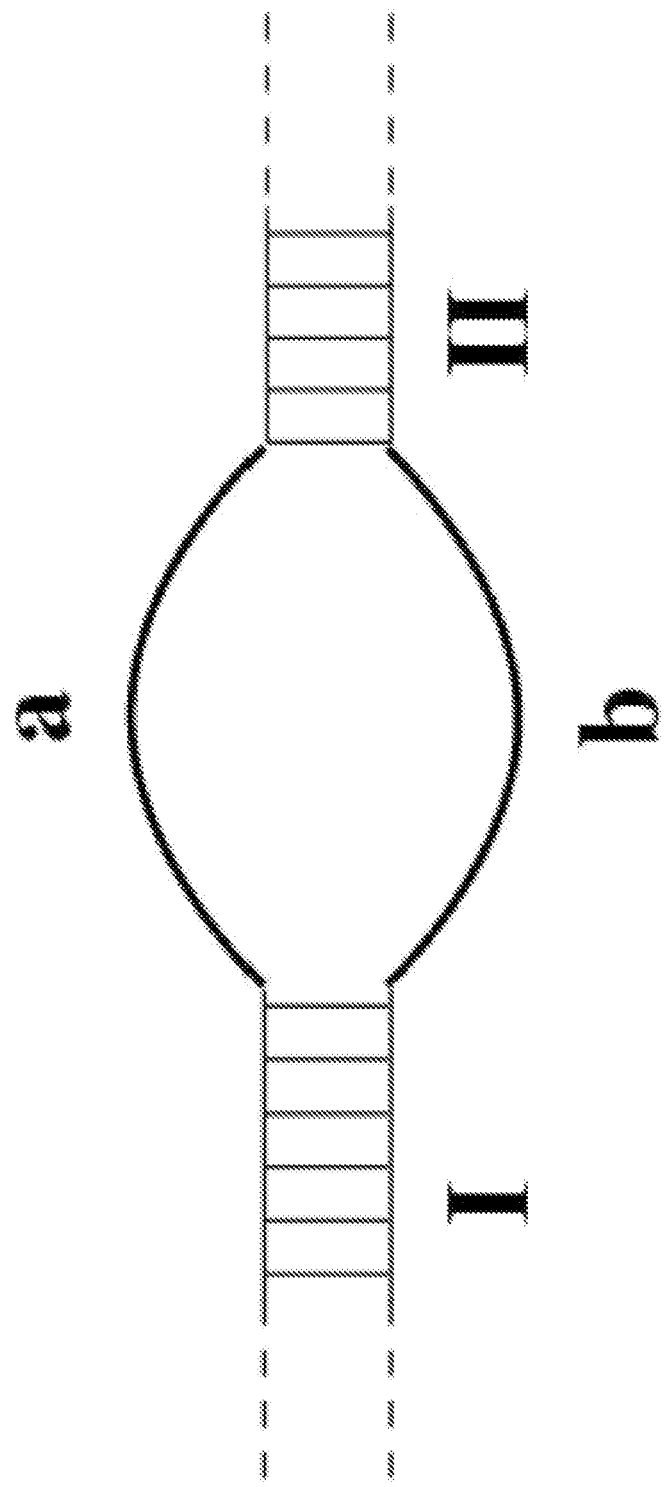
FIG. 2 depicts a typical structure of an miRNA inhibiting complex used herein, depicting a mode in which two RNA strands comprising an MBS are each bound to a respective strand of two double-stranded structures so that the strands are sandwiched by the two double-stranded structures.
Figure 3:
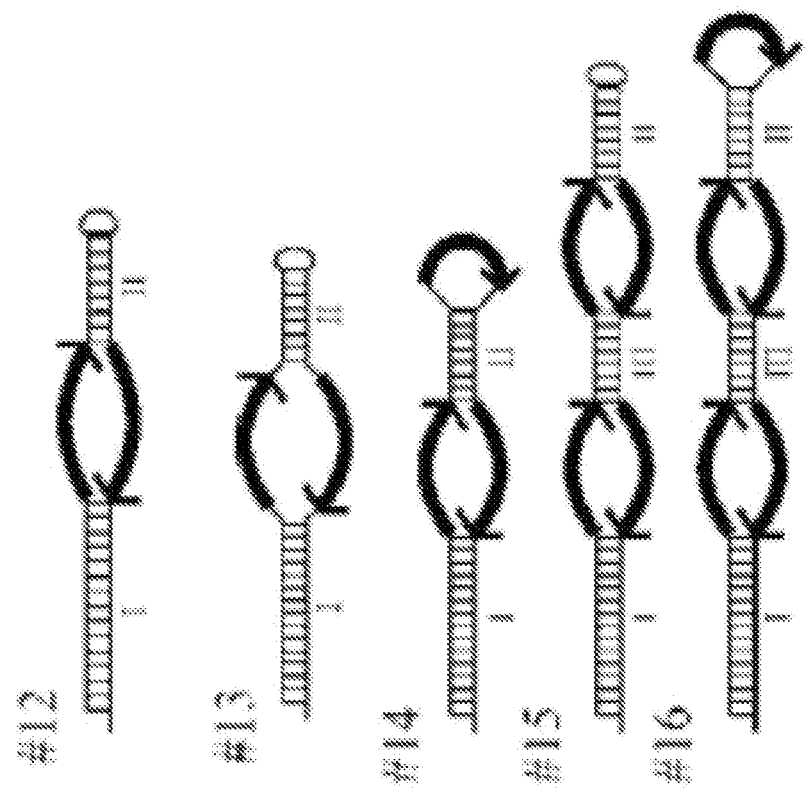
FIG. 3 also depicts a typical structure of an miRNA inhibiting complex used herein, where #12 to #16 are depicted as typical examples. In this regard, two RNA strands comprising an MBS are bound to the respective paired strand of double-stranded structures. Thus, the directions of the RNA strands are in opposition directions with respect to each other.

In one embodiment, the miRNA inhibiting complex used herein further comprises a second double-stranded structure in addition to a first double-stranded structure, has a structure in which RNA strands comprising an MBS are each bound to one of two strands on one end of the first double-stranded structure, wherein the other ends of the RNA strands are each bound to one of two strands on one end of the second double-stranded structure so that the RNA strands are sandwiched between the first double-stranded structure and the second double-stranded structure. For example, the miRNA inhibiting complex comprises a plurality of miRNA binding sequences such as 2 to 5 miRNA binding sequences. A miRNA inhibiting complex comprising a plurality of miRNA binding sequences is advantageous for simultaneously suppressing a plurality of miRNAs and useful in treating or preventing tumor, which is effectively treated or prevented by suppression of a plurality of miRNAs. In one embodiment, the miRNA inhibiting complex comprises two miRNA binding sequences. The double stranded structure may be a double-strand or a quadruple strand such as a G-quadruplex. For example, the present invention in one embodiment further comprises a second double-stranded structure in addition to a first double-stranded structure, and has a structure in which RNA strands comprising an MBS are each bound to one of two strands on one end to which an MBS is bound of the first double-stranded structure, wherein the other ends of the RNA strands are each bound to one of two strands of the second double-stranded structure so that the RNA strands are sandwiched between the first double-stranded structure and the second double-stranded structure. For example, said RNA complex has a structure having at least two double-stranded structures, wherein four RNA strands constituting the two double-stranded structures are each bound to an RNA comprising an MBS without mediation of any of the remaining three strands. More simply stated, such an miRNA inhibiting complex is an miRNA-inhibiting complex in which two RNA strands comprising an MBS are each bound to one strand of two double-stranded structures so that the strands are sandwiched between the two double-stranded structures (FIG. 2). In other words, the present invention encompasses an RNA, which is an RNA complex having the structure of FIG. 2, wherein the RNA strands a and b are sandwiched between double-stranded structures I and II, and one or more MBSes are comprised in each of said a and b. The two RNA strands comprising an MBS are bound to the respective paired strands in the double-stranded structures. Thus, the directions of the RNA strands are opposite to each other (FIG. 3, #12 to #16). By adding an MBS to each of the two strands in this manner, higher miRNA-inhibiting activity can be exerted.

Each of the two RNA strands comprising an MBS, which are sandwiched between two double-stranded structures, comprises one or more MBSes. Such MBSes may have the same or different sequences, target the same miRNA, or sequences that bind to different target miRNAs. For example, a single strand may comprise two or more, e.g., two, three, four, or five MBSes (FIG. 3, #12 to #16). For example, one or two MBSes may be comprised in each strand sandwiched between two double-stranded structures. For example, the miRNA inhibiting complex used herein may comprise two MBSes in total, and the two MBSes may have the same sequence or may be sequences that bind to the same miRNA, or may have different sequence or may be sequences that bind to different miRNAs.

Each of the paired strands in a double strand comprised in the miRNA inhibiting complex used herein is generally a separate RNA molecule as disclosed above, but one or both ends of the double strand may be bound to be straight or cyclic. "Straight" is a term that is used relative to "cyclic", meaning only that a strand has ends. Of course, this does not mean that a secondary structure is not formed. An miRNA inhibiting complex comprised of a straight single-stranded RNA can be produced, for example, by a single RNA synthesis. For example, when comprising two double-stranded structures, two strands on one end (the side to which an MBS is not bound) of a second double-stranded structure can be linked with a loop to form a single strand as a whole. A sequence linking a double strand may comprise one or more MBSes (e.g., FIG. 3; #13, #14, and #16). To make the sequence as compact as possible, the double strands can be linked with a short loop. A double strand can be bound with a sequence of, for example, one to ten bases, preferably one to eight bases, two to six bases, three to five bases, such as four bases. Examples of the sequences include, but are not particularly limited to, 5'-GUCA-3'. For example, the present invention encompasses an RNA having the structure of FIG. 3 #13, in which RNA strands a and b are sandwiched between double-stranded structures I and II, wherein the double-stranded structure II forms a hairpin (or a stem loop), and each of said a and b comprises one or more MBSes.

The sequence of a double-stranded structure comprised in the miRNA inhibiting complex used herein is not particularly limited, and thus can have any length of bases. A preferred embodiment is disclosed in more detail below.

The sequences of base pairs forming a double-stranded structure can be designed appropriately so that a double strand can be formed specifically and stably in an miRNA inhibiting complex. For example, it is preferable to avoid a homopolymeric sequence with a long repetition of the same base (e.g., eight or more bases, preferably seven or more bases, more preferably five or more bases, more preferably four or more bases, and more preferably three or more bases). It is also preferable to avoid sequences in which sequences of several bases are repeated in tandem, such as two-base repeat sequences or three to four base repeat sequences. The GC content of the double-stranded moiety can be adjusted appropriately, which is for example 12% to 85%, preferably 15% to 80%, 20% to 75%, 25% to 73%, 32% to 72%, 35% to 70%, 37% to 68%, or 40% to 65%. An example thereof include, but is not limited to, the sequences of stem I and stem II shown in Japanese Patent No. 4936343. An example of a quadruple strand includes a G-quadruplex, which can have the specific sequence of GGG-loop-GGG-loop-GGG-loop-GGG (SEQ ID NO: 42). In this regard, the sequence of loop can be selected appropriately. For example, all of the three loops may be a single base (e.g., M (A or C)), or three bases.

MBSes and double-stranded structures may be linked directly or via another sequence. For example, an MBS can be bound to an end of a double-stranded structure via a suitable linker or a spacer sequence. While significant inhibitory activity can be obtained by directly linking an MBS to a double-stranded moiety, an addition of a linker (also referred to as a spacer) further elevates the inhibitory effect on miRNAs. A linker or spacer sequence between an MBS sequence and a double-stranded structure may increase the accessibility of an MBS to an miRNA, which is present in RISC. The length of a linker or spacer may be adjusted appropriately. Examples thereof include one to ten bases, preferably one to nine bases, one to eight bases, one to seven bases, one to six bases, one to five bases, one to four bases, and one to three bases. For example, two or more MBSes can also be linked via a linker or spacer. There is no particular limitation on the sequence of a linker or spacer. For example, it can be a sequence consisting of A and/or C, or a sequence comprising more A and/or C than other bases. Further, it is preferable to not make the linker or spacer sequences to form stable base pairs between opposing linker or spacer sequences or MBSes. Examples thereof include AGA, AAC, CAA, ACC, CCA, sequences comprising any one of them, and the like. A pair of linker or spacer sequences that are added to both sides of an MBS may be inverted sequences (mirror-image sequences). For example, AAC can be added to the 5' side of an MBS and CAA can be added to the 3' side.

Nucleic acids constituting the miRNA inhibiting complexes used herein are characteristically modified by a specific modified nucleic acid of the invention, but may comprise a modified nucleic acid other than the specific modified nucleic acid. For example, nucleotides constituting a nucleic acid may comprise, in addition to the specific modified nucleic acids of the invention, a naturally-occurring nucleotide, modified nucleotide, artificial nucleotide, or combination thereof. As long as the specific modified nucleic acid mentioned herein is comprised, nucleic acids comprised in the miRNA inhibiting complexes used herein may also consist of RNAs in addition to the specific modified nucleic acid, or may be RNA/DNA chimeras, or may comprise other nucleic acid analogs or any combination thereof. As long as the specific modified nucleic acid of the invention is comprised, nucleic acids include not only those bound by a phosphodiester bond, but also those having an amide bond or another backbone (peptide nucleic acids (PNAs) and the like). Nucleic acid analogs include, for example, naturally-occurring and artificial nucleic acids. They may also be nucleic acid derivatives, nucleic acid analogs, nucleic acid derivatives, or the like. Such nucleic acid analogs are well known in the art. Examples thereof include, but are not limited to, phosphorothioate, phosphoramidate, methylphosphonate, chiral methylphosphonate, 2"-O-methylribonucleotide, and peptide nucleic acid (PNA). The PNA backbones may include a backbone consisting of aminoethylglycine, polyamide, polyethyl, polythioamide, polysulfinamide, polysulfonamide, or a combination thereof (Krutzfeldt, J. et al., Nucleic Acids Res. 35: 2885-2892; Davis, S. et al., 2006, Nucleic Acids Res. 34: 2294-2304; Boutla, A. et al., 2003, Nucleic Acids Res. 31: 4973-4980; Hutvagner, G. et al., 2004, PLoS Biol. 2: E98; Chan, J. A. et al., 2005, Cancer Res. 65: 6029-6033; Esau, C. et al., 2004, J. Biol. Chem. 279: 52361-52365; Esau, C. et al., 2006, Cell Metab. 3: 87-98).

(Bridged Nucleic Acid (BNA) Used in the Present Invention)

One of the features of the miRNA inhibiting complex used in the present invention is to comprise a stabilizing nucleic acid as a specific modified nucleic acid, i.e., a modified nucleic acid promoting double-strand formation, such as, in the broadest sense, a bridged nucleic acid (BNA).

As used herein, "bridged nucleic acid (BNA) "(BNA refers to both Bicyclic Nucleic Acid and Bridged Nucleic Acid; also referred to as "bridged/bicyclic nucleic acid") refers to any modified nucleic acid, which is linked (bridged) between positions 2' and 4' of a nucleic acid to have two cyclic (bicyclic) structures.

In one exemplary embodiment, a bridged nucleic acid can be used as a stabilizing nucleic acid used in the present invention (i.e., modified nucleic acid promoting double-strand formation). Examples of bridged nucleic acids that can be used include those described in Japanese Patent No. 4731324, Pradeep S. Pallan et al., Chem Commun (Camb). 2012 Aug. 25; 48(66): 8195-8197. doi:10.1039/c2cc32286b, including Locked Nucleic Acid (LNA), ethylene nucleic acids such as 2"-O,4"-C-ethylene bridged nucleic acid (ENA), other bridged nucleic acids (BNA), hexitol nucleic acid (HNA), morpholino nucleic acids, tricyclo-DNA (tcDNA), polyether nucleic acids (see for example U.S. Pat. No. 5,908,845) cyclohexene nucleic acids (CeNA), and combinations thereof.

As used herein, "substitution" refers to substitution of a specific hydrogen atom of an organic compound such as a bridged nucleic acid (BNA) with another atom or group of atoms.

As used herein, a "substituent" refers to an atom or a functional group substituting another atom or functional group in a chemical structure of a bridged nucleic acid (BNA) or the like.

Examples of substituents that can be used in the miRNA inhibiting complex used herein include, but are not limited to, alkyl, cycloalkyl, alkenyl, cycloalkenyl, alkynyl, cycloalkynyl, alkoxy, carbocyclic group, heterocyclic group, halogen, hydroxy, thiol, cyano, nitro, amino, carboxy, carbamoyl, acyl, acylamino, thiocarboxy, amido, substituted carbonyl, substituted thiocarbonyl, substituted sulfonyl, and substituted sulfinyl. All substituents can be substituents other than hydrogen.

As used herein, substitution refers to substitution of one or more hydrogen atoms in a certain organic compound or a substituent with another atom or group of atoms, or conversion thereof into a double or triple bond, unless specifically noted otherwise. It is also possible to remove one hydrogen atom and substitute it with a monovalent substituent or form a double bond with a single bond. In addition, it is possible to remove two hydrogen atoms and substitute them with a divalent substituent or form a triple bond with a single bond.

As used herein, "alkyl" refers to a monovalent group generated by losing one hydrogen atom from an aliphatic hydrocarbon (alkane) such as methane, ethane, or propane. Alkyl is generally represented by $C_nH_{2n+1}$ (wherein n is a positive integer). Alkyl can be a straight or a branched strand. A specific example thereof can be C1-C2 alkyl, C1-C3 alkyl, C1-C4 alkyl, C1-C5 alkyl, C1-C6 alkyl, C1-C7 alkyl, C1-C8 alkyl, C1-C9 alkyl, C1-C10 alkyl, C1-C11 alkyl, or C1-C20 alkyl, or C1-C2 substituted alkyl, C1-C3 substituted alkyl, C1-C4 substituted alkyl, C1-C5 substituted alkyl, C1-C6 substituted alkyl, C1-C7 substituted alkyl, C1-C8 substituted alkyl, C1-C9 substituted alkyl, C1-C10 substituted alkyl, C1-C11 substituted alkyl, or C1-C20 substituted alkyl. In this regard, C1-C10 alkyl, for example, refers to a straight or branched alkyl with 1 to 10 carbon atoms. As used herein, "substituted alkyl" refers to alkyl having H of alkyl substituted with a substituent specified herein. Specific examples thereof include, but are not limited to, $CH_3OCH_2—$, $CH_3OCH_2CH_2—$, $CH_3OCH_2CH_2CH_2—$, $HOCH_2—$, $HOCH_2CH_2—$, $HOCH_2CH_2CH_2—$, $NCCH_2—$, $NCCH_2CH_2—$, $NCCH_2CH_2CH_2—$, $FCH_2—$, $FCH_2CH_2—$, $FCH_2CH_2CH—$, $H_2NCH_2—$, $H_2NCH_2CH_2—$, $H_2NCH_2CH_2CH_2—$, $HOOCCH_2—$, $HOOCCH_2CH_2—$, and $HOOCCH_2CH_2CH_2—$.

As used herein, "alkylene" refers to a divalent group generated by losing two hydrogen atoms from an aliphatic hydrocarbon (alkane) such as methane, ethane, or propane. Alkylene is generally represented by $—C_nH_{2n}—$ (wherein n is a positive integer). Alkylene can be a straight or branched strand. As used herein, "substituted alkylene" refers to alkylene with H of alkylene substituted with an aforementioned substituent. A specific example thereof can be C1 alkylene, C1-C2 alkylene, C1-C3 alkylene, C1-C4 alkylene, C1-C5 alkylene, C1-C6 alkylene, C1-C7 alkylene, C1-C8 alkylene, C1-C9 alkylene, C1-C10 alkylene, C1-C11 alkylene or C1-C20 alkylene, or C1-C2 substituted alkylene, C1-C3 substituted alkylene, C1-C4 substituted alkylene, C1-C5 substituted alkylene, C1-C6 substituted alkylene, C1-C7 substituted alkylene, C1-C8 substituted alkylene, C1-C9 substituted alkylene, C1-C10 substituted alkylene, C1-C11 substituted alkylene, or C1-C20 substituted alkylene. In this regard, C1-C10 alkylene, for example, refers to a straight or branched alkylene with 1 to 10 carbon atoms. For example, C1-C10 substituted alkylene refers to C1-C10 alkylene having one or more hydrogen atoms substituted with a substituent. As used herein, "alkylene" may comprise one or more atoms selected from an oxygen atom and a sulfur atom.

As used herein, "cycloalkyl" refers to alkyl having a cyclic structure. "Substituted cycloalkyl" refers to cycloalkyl having H of cycloalkyl substituted with an aforementioned substituent. A specific example thereof can be C3-C4 cycloalkyl, C3-C5 cycloalkyl, C3-C6 cycloalkyl, C3-C7 cycloalkyl, C3-C8 cycloalkyl, C3-C9 cycloalkyl, C3-C10 cycloalkyl, C3-C11 cycloalkyl, C3-C20 cycloalkyl, C3-C4 substituted cycloalkyl, C3-C5 substituted cycloalkyl, C3-C6 substituted cycloalkyl, C3-C7 substituted cycloalkyl, C3-C8 substituted cycloalkyl, C3-C9 substituted cycloalkyl, C3-C10 substituted cycloalkyl, C3-C11 substituted cycloalkyl, or C3-C20 substituted cycloalkyl.

As used herein, "alkenyl" refers to a monovalent group generated by losing one hydrogen atom from an aliphatic hydrocarbon having a double bond in the molecule. Alkenyl is generally represented by $C_nH_{2n-1}—$ (wherein n is a positive integer that is 2 or greater). "Substituted alkenyl" refers to alkenyl with H of alkenyl substituted with an aforementioned substituent. A specific example thereof can be C2-C3 alkenyl, C2-C4 alkenyl, C2-C5 alkenyl, C2-C6 alkenyl, C2-C7 alkenyl, C2-C8 alkenyl, C2-C9 alkenyl, C2-C10 alkenyl, C2-C11 alkenyl or C2-C20 alkenyl, or C2-C3 substituted alkenyl, C2-C4 substituted alkenyl, C2-C5 substituted alkenyl, C2-C6 substituted alkenyl, C2-C7 substituted alkenyl, C2-C8 substituted alkenyl, C2-C9 substituted alkenyl, C2-C10 substituted alkenyl, C2-C11 substituted alkenyl, or C2-C20 substituted alkenyl. In this regard, C2-C10 alkyl, for example, refers to straight or branched alkenyl comprising 2 to 10 carbon atoms. For example, C2-C10 substituted alkenyl refers to C2-C10 alkenyl with one or more hydrogen atoms substituted with a substituent.

As used herein, "aryl" refers to a group generated by one hydrogen atom binding to an aromatic hydrocarbon ring leaving. As used herein, aryl is encompassed by carbocyclic group. A phenyl group ($C_6H_5$-) is induced from benzene, tolyl group ($CH_3C_6H_4—$) is induced from toluene, xylyl group (($CH_3$)$_2C_6H_3$-) is induced from xylene, and naphthyl group ($C_{10}H_B—$) is induced from naphthalene.

As used herein, "aralkyl" refers to an alkyl group with one hydrogen atom of an alkyl group substituted with an aryl group. A specific example of an aralkyl group can be benzyl group, phenethyl group, 1-naphthyl ethyl group, or the like.

As used herein, "acyl" refers to a monovalent group, which is produced by removing OH from carboxylic acid. Representative examples of acyl groups include acetyl ($CH_3CO—$), benzoyl ($C_6H_5CO—$), and the like. "Substituted acyl" refers to acyl with hydrogen substituted with an aforementioned substituent.

As used herein, "sulfonyl" collectively refers to those comprising the characteristic group —SO$_2$—. "Substituted sulfonyl" refers to sulfonyl having a substitution with an aforementioned substituent.

As used herein, "silyl" is generally a group represented by SiR$_1$R$^2$R$_3$— (wherein R$_1$, R$_2$, and R$_3$ are each independently selected from the group consisting of hydrogen, alkyl, cycloalkyl, alkenyl, cycloalkenyl, alkynyl, cycloalkynyl, alkoxy, carbocyclic group, and heterocyclic group). A specific example thereof can be trimethylsilyl group, triethylsilyl group, triethylsilyl group, tert-butyldimethylsilyl group, triisopropylsilyl group, or tert-butyldiphenylsilyl group.

As used herein, "functional molecule unit substituent" refers to groups including labeling molecules (e.g., molecule species including fluorescent molecules, chemiluminescent molecules, radioactive isotope atoms, and the like), DNA or RNA cleavage activity molecules, intracellular or nuclear translocation signal peptides and the like.

In one embodiment, the BNA can be a BNA that is bridged via at least one atom selected from the group consisting of oxygen and carbon on the position 2' side and via at least one atom selected from the group consisting of carbon and nitrogen and carbon on the position 4' side.

In a representative embodiment, the BNA used in the present invention is a 2',4' substituted bridged nucleic acid represented by the following BNA-1

[Chemical Formula 17]

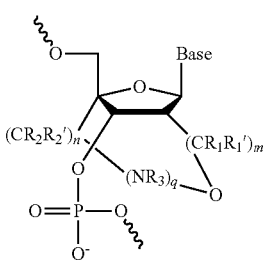

BNA-1 wherein R$_1$, R$_1'$, R$_2$, R$_2'$, and R$_3$ each independently represent a group selected from the group consisting of a hydrogen atom, a substituted or unsubstituted alkyl group, a substituted or unsubstituted alkenyl group, a substituted or unsubstituted cycloalkyl group, a substituted or unsubstituted aryl group, a substituted or unsubstituted aralkyl group, a substituted or unsubstituted acyl group, a substituted or unsubstituted sulfonyl group, a substituted or unsubstituted silyl group, and a functional molecule unit substituent, such as, but not limited to, a substituted or unsubstituted phenoxyacetyl group, alkyl group with 1 to 5 carbons, alkenyl group with 1 to 5 carbons, aryl group with 6 to 14 carbons, methyl group substituted with 1 to 3 aryl groups, lower aliphatic or aromatic sulphonyl group such as methane sulphonyl group or p-toluene sulphonyl group, aliphatic acyl group with 1 to 5 carbons such as acetyl group, or aromatic acyl group such as benzoyl group, n is an integer from 1 to 3, and q is an integer that is 0 or 1.

Base is a purine-9-yl group, a 2-oxo-pyrimidine-1-yl group, or a derivative thereof. Examples are provided by for example, but not limited to, Japanese Patent No. 4731324, and typical examples thereof in the present invention include 6-aminopurine-9-yl (i.e., adeninyl), 2-amino-6-chloropurine-9-yl, 2-amino-6-fluoropurine-9-yl, 2-amino-6-bromopurine-9-yl, 2-amino-6-hydroxypurine-9-yl (i.e., guaninyl), 6-amino-2-chloropurine-9-yl, 6-amino-2-fluoropurine-9-yl, 2,6-dimethoxypurine-9-yl, 2,6-dichloropurine-9-yl, 6-mercaptopurine-9-yl, 2-oxo-4-amino-1, 2-dihydropyrimidine-1-yl (i.e., cytosinyl), 2-oxo-4-amino-5-fluoro-1,2-dihydropyrimidine-1-yl, 4-amino-2-oxo-5-chloro-1,2-dihydropyrimidine-1-yl, 2-oxo-4-methoxy-1,2-dihydropyrimidine-1-yl, 2-oxo-4-mercapto-1,2-dihydropyrimidine-1-yl, 2-oxo-4-hydroxy-1,2-dihydropyrimidine-1-yl (i.e., uracilyl), 2-oxo-4-hydroxy-5-methyl-1,2-dihydropyrimidine-1-yl (i.e., thyminyl), 4-amino-5-methyl-2-oxo-1,2-dihydropyrimidine-1-yl (e.g., 5-methylcytosinyl), 9-β-D-ribofuranosyl hypoxanthinyl (i.e., inosinyl) and derivatives thereof, preferably adeninyl, thyminyl, guaninyl, uracilyl, inosinyl, cytosinyl, 5-methylcytosinyl, and derivatives thereof.

In another representative embodiment, the BNA used in the present invention includes a 2',4' substituted bridged nucleic acid represented by the following BNA-2

[Chemical Formula 18]

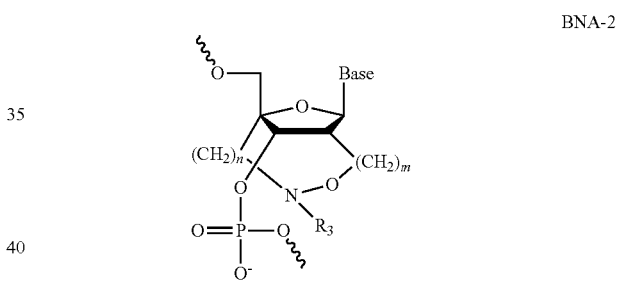

BNA-2 wherein R$_3$ represents a group selected from the group consisting of a hydrogen atom, a substituted or unsubstituted alkyl group, a substituted or unsubstituted alkenyl group, a substituted or unsubstituted cycloalkyl group, a substituted or unsubstituted aryl group, a substituted or unsubstituted aralkyl group, a substituted or unsubstituted acyl group, a substituted or unsubstituted sulfonyl group, a substituted or unsubstituted silyl group, and a functional molecule unit substituent, such as, but not limited to, a phenoxyacetyl group, alkyl group with 1 to 5 carbons, alkenyl group with 1 to 5 carbons, aryl group with 6 to 14 carbons, methyl group substituted with 1 to 3 aryl groups, lower aliphatic or aromatic sulphonyl group such as methane sulphonyl group and p-toluene sulphonyl group, aliphatic acyl group with 1 to 5 carbons such as acetyl group, or aromatic acyl group such as benzoyl group, m is an integer from 0 to 2, and n is an integer from 1 to 3. Base is the same as that described for BNA-1, which can be preferably adeninyl, guaninyl, thyminyl, uracinyl, inosinyl, cytosinyl, 5-methylcytosinyl, and derivatives thereof.

In another representative embodiment, the BNA used in the present invention is the following BNA-3

[Chemical Formula 19]

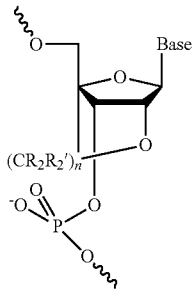

BNA-3 wherein $R_2$ and $R_{2'}$ each independently represent a group selected from the group consisting of a hydrogen atom, a substituted or unsubstituted alkyl group, a substituted or unsubstituted alkenyl group, a substituted or unsubstituted cycloalkyl group, a substituted or unsubstituted aryl group, a substituted or unsubstituted aralkyl group, a substituted or unsubstituted acyl group, a substituted or unsubstituted sulfonyl group, a substituted or unsubstituted silyl group, and a functional molecule unit substituent, such as, but not limited to, a methyl group or O-methoxyethyl group, and Base is the same as that described for BNA-3, which can be preferably adeninyl, guaninyl, thyminyl, uracinyl, inosinyl, cytosinyl, 5-methylcytosinyl, and derivatives thereof, wherein n is an integer from 1 to 3, but one of $R_2$ and $R_{2'}$ is not hydrogen.

Examples of BNAs with a branch in a bridged strand are, but not limited thereto, BNA(cEt)

[Chemical Formula 20]

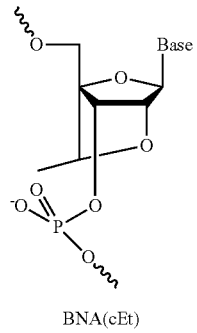

BNA(cEt)

(cEt: 2',4'-constrained ethyl). Although BNA(cEt) has thermostability and mismatch identification similar to conventional LNAs, it is known to have improved stability against nuclease.

In a representative embodiment, the BNA used in the present invention may be

[Chemical Formula 21]

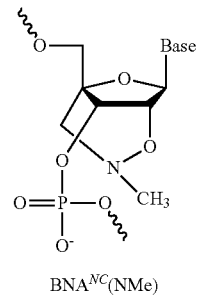

BNA$^{NC}$(NMe)

(which is denoted herein as "BNA$^{NC}$(NMe)" unless specifically noted otherwise, but may also be described as "(2',4'-)BNA$^{NC}$", wherein Base has the same aforementioned definition, which is preferably selected from the group consisting of adeninyl, thyminyl, guaninyl, uracilyl, inosinyl, cytosinyl, and 5-methylcytosinyl.

As used herein, a "protecting group" refers to a group used for protecting a functional group from a specific chemical reaction. As used herein, a protecting group may be denoted as "PG".

Preferably, BNA$^{NC}$(NMe) or LNA, more preferably BNA$^{NC}$(NMe), is used as a BNA.

In a preferred embodiment, m is 0 and n is 1.

Thus, when used in miRNAs, this can be an oligonucleotide or a pharmacologically acceptable salt thereof as a DNA oligonucleotide or an RNA oligonucleotide comprising one or more of one or more types of unit structures of nucleosides represented by the general formula (II) described below. In this regard, the form of bond between each nucleoside in an oligonucleotide may comprise one or more phosphothioate bonds [—OP(O) (S—)O-] besides a phosphodiester bond [—OP(O$_2$—)O-] which is the same as a naturally-occurring nucleic acid. When comprising two or more of one or more types of the aforementioned structures, Base can be the same or different between the structures.

A DNA or RNA oligonucleotide analog (II) comprising an artificial nucleic acid BNA$^{NC}$(NMe) [in general formula (I), $R_1$ and $R_2$ are hydrogen, and $R_3$ is hydrogen or methyl group], which is one type of the present invention, has the excellent characteristic described below. This is because the capability to form a double strand with respect to a complementary RNA strand is extremely high.

The Tm value increases 3 to 6° C. for each BNA$^{NC}$(NMe) introduced into a DNA oligonucleotide (per one modification) Moreover, there is hardly any increase (improvement) in the capability to form a double strand with respect to a complementary DNA strand. This characteristic entails a dramatic increase in the Tm value (significant improvement in the capability to form a double strand) as in BNA modified DNA oligonucleotides in terms of binding affinity to complementary RNA strands, but improvement in the capability to form a double strand with respect to a complementary DNA strand is observed in BNA modified DNA oligonucleotides compared to unmodified DNA oligonucleotides (increase of 2 to 4° C. in the Tm value per modification). In contrast, improvement in binding affinity is hardly observed in BNA$^{NC}$(NMe) modified DNA oligonucleotides. Thus, BNA$^{NC}$(NMe) modified DNA oligonucleotides have excellent selective binding affinity to an RNA strand.

(2) BNA$^{NC}$(NMe) modified DNA oligonucleotides also have superior capability to form a triple strand with respect to a double-stranded DNA strand.

The Tm value increases 7 to 12° C. in forming a triple strand with respect to a double-stranded DNA strand when a BNA$^{NC}$(NMe) unit is introduced into a DNA oligonucleotide. Further, a triple strand formation requires sequence selectivity for strictly identifying a base sequence and binding only to a target sequence. Meanwhile, the difference in the Tm value for a matching sequence and a mismatching sequence of a BNA$^{NC}$(NMe) modified DNA oligonucleotide is 25° C. or greater, thus having better sequence selectivity than a naturally-occurring DNA oligonucleotide. The nuclease resistance of BNA$^{NC}$(NMe) is excellent.

BNA$^{NC}$(NMe) modified oligonucleotides have higher nuclease resistance than naturally-occurring DNA oligonucleotides, but much lower than S-oligo (phosphorothioate oligonucleotide). The BNA$^{NC}$(NMe) modified oligonucleotide of the invention has better nuclease resistance than S-oligo, which is highly valued for its excellent nuclease resistance, not to mention BNA modified oligonucleotides. The BNA$^{NC}$(NMe) modified oligonucleotide of the invention is also characterized by strong resistance to degradation in vivo.

(3) The N—O bond comprised in the artificial nucleic acid, BNA$^{NC}$(NMe) of the invention, can be selectively cleaved under moderate conditions with a reducing reagent to free an NH group and an OH group. By using the NH group and the OH group to bind a molecule with another function, various complexes (conjugates) can be readily obtained, before or after the preparation of an oligonucleotide analog. Labeling molecules such as molecular species including fluorescent molecules, chemiluminescent molecules, and radioactive isotope atoms, various DNA (RNA) cleavage activity molecules, intracellular or nuclear translocation signal peptides, or the like can be used as molecules with another function.

DNA or RNA oligonucleotide analogs with a BNA$^{NC}$ (NMe) modification in various forms are highly useful, not only as highly functional materials for development of genetic medicaments using antisense method, antigene method, decoy method, gene homologous recombination, RNA interference process, or the like, but also as a substrate for gene diagnosis methods such as a molecular beacon or DNA chip, or as material for developing reagents used for research such as gene function analysis/elucidation.

Examples of suitable compounds among the compounds (BNA-1) of the invention and salts thereof include (5) compounds in which $R_3$ is a hydrogen atom, alkyl group with 1 to 5 carbons, alkenyl group with 1 to 5 carbons, aryl group with 6 to 14 carbons, methyl group substituted with 1 to 3 aryl groups, lower aliphatic or aromatic sulphonyl group such as methane sulphonyl group or p-toluene sulphonyl group, aliphatic acyl group with 1 to 5 carbons such as acetyl group, aromatic acyl group such as benzoyl group or phenoxyacetyl group, and a salt thereof, and compounds in which a functional molecule unit substituent of $R_3$ is a fluorescent or chemiluminescent labeling molecule, nucleic acid cleavage activity functional group, or intracellular or nuclear translocation signal peptide, and (6) Base is as disclosed above, preferably an adeninyl group, a thyminyl group, a uracilyl group, an inosinyl group, a cytosinyl group, a guaninyl group, a methylcytosinyl group, or a derivative thereof.

The nucleoside analog and oligonucleotide analog of the invention can be synthesized based on the methods described in the Examples and conventional technologies in the art.

(1) Synthesis of Nucleoside Analog ((BNA-1) and (BNA-2))

Compounds represented by the general formulas (BNA-1) and (BNA-2) can be synthesized based on the methods described in the Examples and conventional technologies in the art. The methods described in the Examples can be referred to for the specific reaction conditions, protecting group introducing reagent, and reaction reagent, but they are not limited thereto. Reaction conditions and reagents that can be used based on the common general knowledge of the art can be appropriately used. For example, the methods described in Japanese Laid-Open Publication No. 2000-297097 or Japanese Laid-Open Publication No. 10-304889 can be referred to. The raw materials for the compounds of the invention can be synthesized by referring to the method described in Japanese Laid-Open Publication No. 10-304889 when Base in general formula (I) or (II) has various naturally-occurring or non-naturally-occurring nucleic acid bases and other aromatic heterocycles or aromatic hydrocarbon rings.

(General Synthesis Example for Nucleoside Analogs)

[Chemical Formula 22]

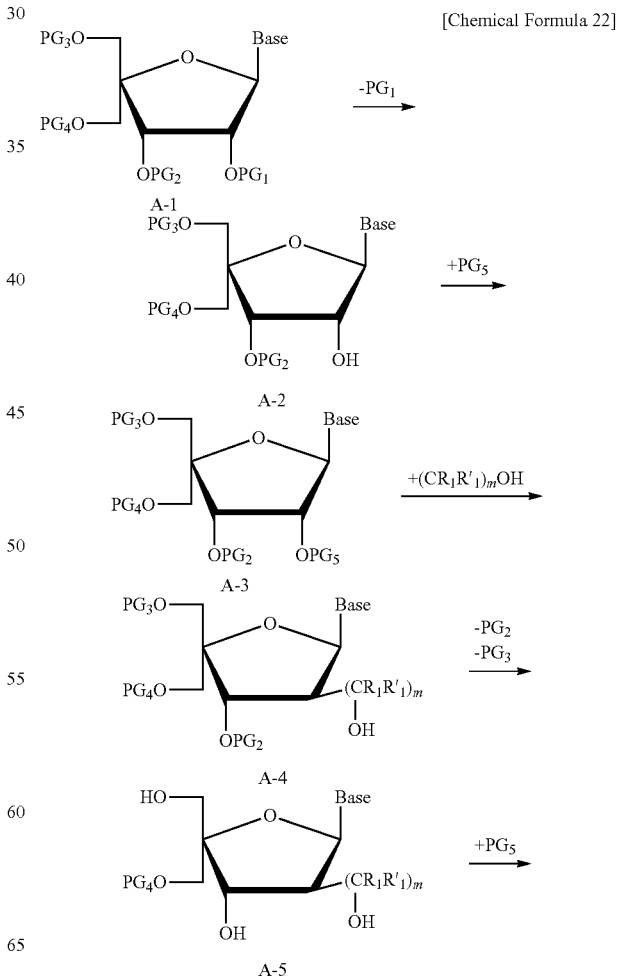

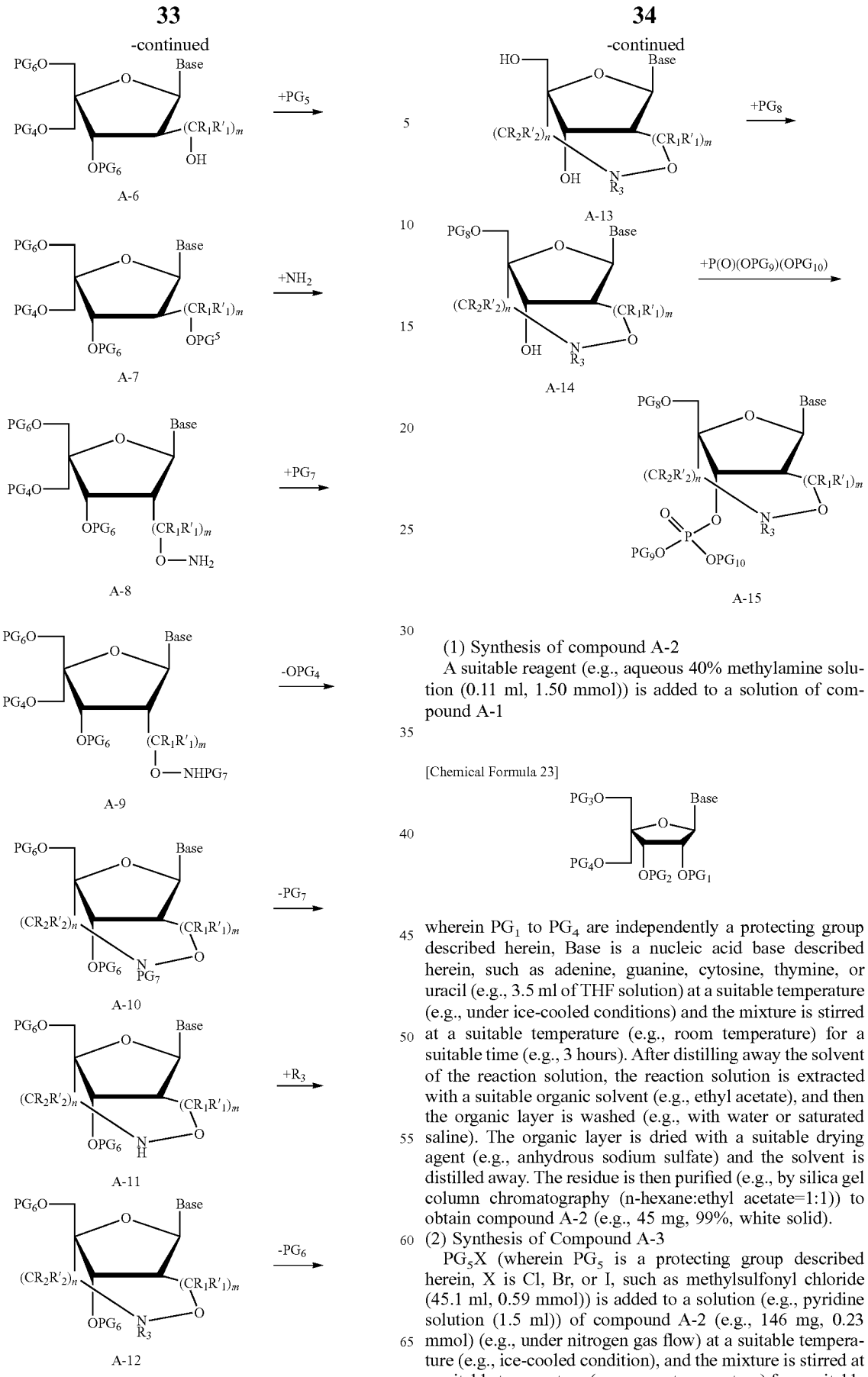

(1) Synthesis of compound A-2

A suitable reagent (e.g., aqueous 40% methylamine solution (0.11 ml, 1.50 mmol)) is added to a solution of compound A-1

[Chemical Formula 23]

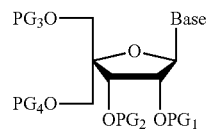

wherein $PG_1$ to $PG_4$ are independently a protecting group described herein, Base is a nucleic acid base described herein, such as adenine, guanine, cytosine, thymine, or uracil (e.g., 3.5 ml of THF solution) at a suitable temperature (e.g., under ice-cooled conditions) and the mixture is stirred at a suitable temperature (e.g., room temperature) for a suitable time (e.g., 3 hours). After distilling away the solvent of the reaction solution, the reaction solution is extracted with a suitable organic solvent (e.g., ethyl acetate), and then the organic layer is washed (e.g., with water or saturated saline). The organic layer is dried with a suitable drying agent (e.g., anhydrous sodium sulfate) and the solvent is distilled away. The residue is then purified (e.g., by silica gel column chromatography (n-hexane:ethyl acetate=1:1)) to obtain compound A-2 (e.g., 45 mg, 99%, white solid).

(2) Synthesis of Compound A-3

$PG_5X$ (wherein $PG_5$ is a protecting group described herein, X is Cl, Br, or I, such as methylsulfonyl chloride (45.1 ml, 0.59 mmol)) is added to a solution (e.g., pyridine solution (1.5 ml)) of compound A-2 (e.g., 146 mg, 0.23 mmol) (e.g., under nitrogen gas flow) at a suitable temperature (e.g., ice-cooled condition), and the mixture is stirred at a suitable temperature (e.g., room temperature) for a suitable time (e.g., 1 hour). The reaction is quenched (e.g., by adding water to the reaction solution), and the reaction solution is extracted with a suitable organic solvent (e.g., ethyl acetate). Next, the organic layer is washed (e.g., with saturated sodium bicarbonate water or saturated saline), and then dried with a suitable drying agent (e.g., anhydrous sodium sulfate). The solvent is removed under reduced pressure to obtain compound A-3. Compound A-3 can also be used in the following reaction without purification.

(3) Synthesis of Compound A-4

A suitable reagent (e.g., aqueous 1M sodium hydroxide solution (0.70 ml, 0.70 mmol)) is added to a solution (e.g., water-ethanol solution (1:2, 6 ml)) of compound A-3 (e.g., 170 mg) at a suitable temperature (e.g., room temperature), and the mixture is stirred for a suitable time (e.g., 1 hour) to introduce $(CR_1R_{1'})_m OH$ at position 2' ($R_1$ and $R_{1'}$ are substituents described herein). After neutralization (e.g., with aqueous 10% hydrochloric acid solution), a reaction solution is extracted with a suitable organic solvent (e.g., ethyl acetate). The organic layer is washed (e.g., with water or saturated saline), and then dried with a suitable drying agent (e.g., anhydrous sodium sulfate). The solvent is distilled away under reduced pressure. The resulting crude product is purified (e.g., by silica gel column chromatography (chloroform:methanol=15:1) to obtain compound A-4 (e.g., 139 mg, 95% (2 stages), white solid).

(4) Synthesis of Compound A-5

A suitable reagent (e.g., 20% palladium hydroxide-carbon powder (0.60 g), or cyclohexene (5.2 ml, 51 mmol)) is added to a solution (e.g., ethanol solution (10 ml)) of compound A-4 (e.g., 0.80 g, 1.28 mmol) (e.g., under nitrogen gas flow) and the mixture is stirred for a suitable time (e.g., 5 hours) under a suitable temperature condition (e.g., heating under reflux) to remove $PG_2$ and $PG_3$. The step of removing $PG_2$ and the step of removing $PG_3$ may be the same step or different steps. After filtering the reaction solution, the solvent is distilled away under reduced pressure. The resulting crude product A-5 can be used in the following reaction without purification.

(5) Synthesis of Compound A-6

$PG_6X$ (wherein $PG_6$ is a protecting group described herein and X is Cl, Br, or I, such as 1,3-dichloro-1,1,3,3-tetraisopropyldisiloxane (0.45 ml, 1.41 mmol)) and a base (e.g., imidazole (0.38 g, 5.63 mmol)) are added to a solution (e.g., N,N-dimethylformamide solution (10 ml)) of compound A-5 (e.g., 0.46 g) (e.g., under nitrogen gas flow), and the mixture is stirred at a suitable temperature (e.g., room temperature) for a suitable time (e.g., 5 hours) to introduce $PG_6$. A reaction solution is extracted with a suitable organic solvent (e.g., ether). The organic layer is washed (e.g., with water or saturated saline), and then dried with a suitable drying agent (e.g., magnesium sulfate). The solvent is distilled away under reduced pressure, and the resulting crude product is purified (e.g., by silica gel column chromatography (n-hexane:ethyl acetate=2:1-1:1)) to obtain compound A-6 (e.g., 0.60 g, 68% (2 stages), white solid).

(6) Synthesis of Compound A-7

$PG_5X$ (wherein $PG_5$ is a protecting group described herein and X is Cl, Br, or I, such as anhydrous trifluoromethanesulfonic acid (0.15 ml, 0.88 mmol)) and base (e.g., 4-(dimethylamino)pyridine (7 mg, 0.06 mmol)) are added to a solution (e.g., pyridine solution (3 ml)) of compound A-6 (e.g., 200 mg, 0.29 mmol) (e.g., under nitrogen gas flow) at a suitable temperature (e.g., under ice cooled condition). The mixture is stirred at a suitable temperature (e.g., room temperature) for a suitable time (e.g., 7.5 hours). The reaction is quenched (e.g., by adding water to the reaction solution) to extract the reaction solution with a suitable organic solvent (e.g., dichloromethane). The organic layer is washed (e.g., with saturated sodium bicarbonate water or saturated saline) and then dried with a suitable drying agent (e.g., anhydrous sodium sulfate). The solvent is distilled away under reduced pressure to obtain compound A-7. The resulting A-7 can be used in the following reaction without purification.

(7) Synthesis of Compound A-8

Compound A-8 introduced with an amino group in a hydroxy group at position 2' of compound A-7 is synthesized. Examples of synthesis methods thereof include, but are not limited to the following: a suitable reagent (e.g., N-hydroxyphthalimide (67 mg, 0.41 mmol) or 1,8-diazabicyclo[5.4.0]-7-undecene (61 (1, 0.41 mmol)) is added to a solution (e.g., acetonitrile solution (3 ml)) of compound A-7 (e.g., 0.29 g) (under nitrogen gas flow) at a suitable temperature (e.g., room temperature), and the mixture is stirred at a suitable temperature (e.g., room temperature) for a suitable time (e.g., 12 hours). The reaction solution is extracted with a suitable organic solvent (e.g., dichloromethane). The organic layer is washed (e.g., with water or saturated saline) and then dried with a suitable drying agent (e.g., anhydrous sodium sulfate). The solvent is distilled away under reduced pressure and the resulting crude product is purified (e.g., by silica gel column chromatography (chloroform)) to obtain compound A-7'. A suitable reagent (e.g., hydrazine monohydrate (0.12 ml, 2.38 mmol)) is added to a solution (e.g., ethanol solution (35 ml)) of the resulting compound A-7' (1.16 g, 1.40 mmol), and the mixture is stirred at a suitable temperature (e.g., room temperature) for a suitable time (e.g., 10 minutes). After distilling away the solvent of the reaction solution, the solution is filtered, and a filtrate is extracted with a suitable organic solvent (e.g., ethyl acetate). The organic layer is washed (e.g., with water or saturated saline), then dried with a suitable drying agent (anhydrous sodium sulfate) The solvent is distilled away under reduced pressure. The obtained A-8 can be used in the following reaction without purification.

(8) Synthesis of Compound A-9

A suitable reagent (e.g., saturated sodium bicarbonate water (4.0 ml, 4.2 mmol)) and $PG_7X$ (wherein $PG_7$ is a protecting group described herein and X is Cl, Br, or I, such as benzyl chloroformate (0.30 ml, 2.1 mmol)) are added to a solution (e.g., methylene chloride solution (15 ml)) of compound A-8 (0.93 g) (e.g., under nitrogen gas flow) at a suitable temperature (e.g., under ice-cooling condition), and the mixture is stirred for a suitable time (e.g., 1 hour) The reaction is quenched (e.g., by adding saturated sodium bicarbonate water), and the reaction solution is extracted with a suitable organic solvent (e.g., ethyl acetate). The organic layer is washed (e.g., with water or saturated saline), and dried with a suitable drying agent (e.g., magnesium sulfate). The solvent is distilled away under reduced pressure and the resulting crude product is purified (e.g., by silica gel column chromatography (n-hexane-ethyl acetate=4:1)) to obtain compound A-9 (e.g., 0.92 g, 94% (2 stages), white solid).

(9) Synthesis of Compound A-10

A solution (e.g., tetrahydrofuran solution (15 ml)) of compound A-9 (e.g., 3.81 g, 4.57 mmol) is dripped into a base (e.g., tetrahydrofuran suspension (25 ml) of sodium hydroxide (60% in oil, 0.55 g, 13.7 mmol) (e.g., under nitrogen gas flow) at a suitable temperature (e.g., under ice-cooled condition), and the mixture is stirred for a suitable time (e.g., 1 hour). $OPG_4$ is removed and positions 2' and 4' are bridged by stirring at a suitable temperature (e.g., room temperature) for a suitable time (e.g., 5 hours) The step of removing $OPG_4$ and the step of bridging positions 2' and 4' may be the same or different steps. After neutralization (e.g., with saturated aqueous oxalic acid solution), a reaction solution is extracted with a suitable organic solvent (e.g., ethyl acetate). The organic layer is washed (e.g., with water or saturated saline), then dried with a suitable drying agent (e.g., anhydrous sodium sulfate) The solvent is distilled away under reduced pressure, and the resulting crude product is purified (e.g., by silica gel column chromatography (chloroform→chloroform:methanol=100:1)) to obtain compound A-10 (e.g., 2.87 g, 95%, white solid).

(10) Synthesis of Compound A-11

A suitable reagent (e.g., 1M boron trichloride hexane solution (5.29 ml, 5.29 mmol)) is added to a solution (e.g., methylene chloride solution (10 ml)) of compound A-10 (e.g., 0.35 mg, 0.53 mmol) (e.g., under nitrogen gas flow) at a suitable temperature (e.g., under ice-cooled condition), and the mixture is stirred for a suitable time (e.g., 1 hour). The reaction is quenched (e.g., by adding saturated sodium bicarbonate water to the reaction solution). The reaction solution is extracted with a suitable organic solvent (e.g., ethyl acetate). The organic layer is washed (e.g., with water or saturated saline), and then dried with a suitable drying agent (e.g., anhydrous sodium sulfate). The solvent is distilled away under reduced pressure, and the resulting crude product is purified (e.g., by silica gel column chromatography (chloroform:methanol=50:1)) to obtain compound A-11 (e.g., 0.27 g, 96%, white solid).

(11) Synthesis of Compound A-12

A suitable reagent (e.g., aqueous 20% formaldehyde solution (0.06 ml, 0.40 mmol)) is added to a solution (e.g., 1 M pyridinium p-toluenesulfonate-methanol solution (3.6 ml)) of compound A-11 (0.19 g, 0.36 mmol) at a suitable temperature (e.g., room temperature), and the mixture is stirred for a suitable time (e.g., 10 minutes). Furthermore, a suitable reagent (e.g., sodium cyanoborohydride (45 mg, 0.72 mmol)) is added at a suitable temperature (e.g., under ice-cooled condition) to substitute an amino group with substituent $R_3$ ($R_3$ is a substituent described herein). The mixture is stirred for a suitable time (e.g., 1 hour). The reaction solution is extracted with a suitable organic solvent (e.g., ethyl acetate) and washed (e.g., with water, saturated sodium bicarbonate water, or saturated saline). The organic layer is dried with a suitable drying agent (e.g., with anhydrous sodium sulfate). The solvent is distilled away under reduced pressure, and the resulting crude product is purified (e.g., by silica gel column chromatography (n-hexane:ethyl acetate=2:1)) to obtain compound A-12 (e.g., 0.19 g, 100%, white solid).

(12) Synthesis of Compound A-13

A suitable reagent (e.g., fluorinated tetra-n-butylammonium (0.17 ml, 0.17 mmol in 1M tetrahydrofuran)) is added to a solution (e.g., tetrahydrofuran solution (2 ml)) of compound A-12 (46 mg, 0.085 mmol), and the mixture is stirred at a suitable temperature (e.g., room temperature) for a suitable time (e.g., 5 minutes). The solvent is distilled away under reduced pressure, and the resulting crude product is purified (e.g., by silica gel column chromatography (ethyl acetate:methanol=15:1)) to obtain compound A-13 (e.g., 25 mg, 100%, white solid).

(13) Synthesis of Compound A-14

A suitable reagent (e.g., 4,4'-dimethoxytrityl chloride (e.g., 0.22 g, 0.64 mmol)) is added to a solution (e.g., pyridine solution (10 ml)) of compound A-13 (e.g., 0.16 g, 0.54 mmol), and the mixture is stirred at a suitable temperature (e.g., room temperature) for a suitable time (e.g., 12 hours). For example, saturated sodium bicarbonate water is added to a reaction solution, and the reaction solution is extracted with a suitable organic solvent (e.g., ethyl acetate). The organic layer is washed (e.g., with water or saturated saline), and then dried with a suitable drying agent (e.g., anhydrous sodium sulfate). The solvent is distilled away under reduced pressure, and the resulting crude product is purified (e.g., by silica gel column chromatography (1% trimethylamine containing n-hexane:ethyl acetate=1:2→ethyl acetate:methanol=30:1)) to obtain compound A-14 (e.g., 0.30 g, 93%, white solid).

(14) Synthesis of Compound A-15

A suitable reagent (e.g., 2-cyanoethyl-N,N,N',N'-tetraisopropylphosphoroamidite (0.13 ml, 0.42 mmol)) is added to a solution (e.g., acetonitrile solution (6 ml)) of compound A-14 (e.g., 0.17 g, 0.28 mmol) and a suitable reagent (e.g., 4,5-dicyanoimidazole (40 mg, 0.34 mmol)). The mixture is stirred at a suitable temperature (e.g., room temperature) for a suitable time (e.g., 4 hours) to modify a hydroxy group at position 3' with $P(O)(OPG_9)(OPG_{10})$ ($PG_9$ and $PG_{10}$ are each independently a protecting group described herein). The reaction is quenched (e.g., by adding saturated sodium bicarbonate water to a reaction solution), and the reaction solution is extracted with a suitable organic solvent (e.g., ethyl acetate). The organic layer is washed (e.g., with saturated sodium bicarbonate water, water, or saturated saline), and then dried with a suitable drying agent (e.g., anhydrous sodium sulfate). The solvent is distilled away under reduced pressure. The resulting crude product is purified (e.g., by silica gel column chromatography (1% triethylamine containing n-hexane:ethyl acetate=1:1) and then re-precipitated (ethyl acetate-hexane) to obtain compound A-15 (e.g., 0.20 g, 88%, white solid).

(BNA-3)

A compound represented by general formula BNA-3 can be synthesized based on the method described in the Examples and conventional technologies in the art. The methods described in the Examples can be referred to for the specific reaction conditions, protecting group introducing reagent, and reaction reagent, but they are not limited thereto. Reaction conditions and reagents that can be used based on the common general knowledge of the art can be appropriately used. For example, the methods described in J. Org. Chem. 2010, 75, 1569-1581 can be referred to. The raw materials for the compounds of the invention can be synthesized by referring to the method described in J. Org. Chem. 2010, 75, 1569-1581 when Base in general formula (I) or (II) has various naturally-occurring or non-naturally-occurring nucleic acid bases and other aromatic heterocycles or aromatic hydrocarbon rings.

General Synthesis Example of BNA-3

[Chemical Formula 24]

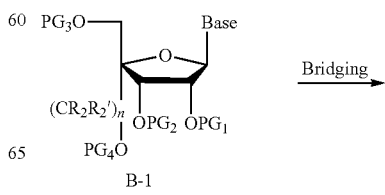

B-1

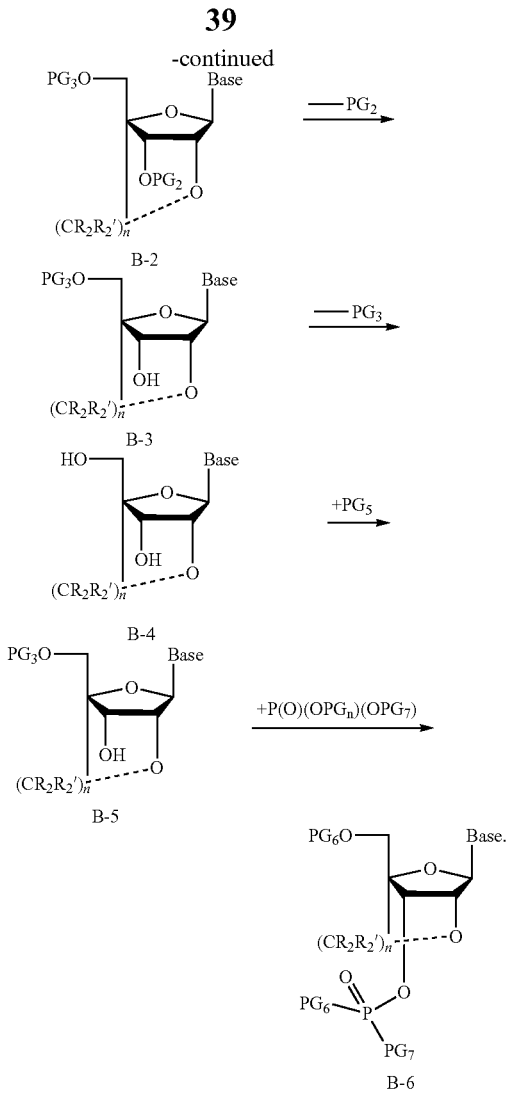

(1) Synthesis of Compound B-2

A suitable reagent (e.g., potassium carbonate) is added to a solution of compound B-1

[Chemical Formula 25]

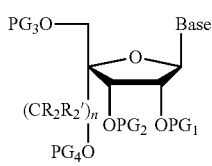

wherein $PG_1$ to $PG_4$ are independently a protecting group described herein, $R_2$ and $R_2'$ are substituents described herein, and Base is a nucleic acid base described herein, such as an adeninyl group, a thyminyl group, a guaninyl group, or a methylcytosinyl group) at a suitable temperature (e.g., under nitrogen gas flow), and the mixture is stirred at a suitable temperature for a suitable time. The reaction is quenched (e.g., by adding water to the reaction solution), and the reaction solution is extracted with a suitable organic solvent (e.g., ethyl acetate). The organic layer is washed (e.g., with saturated saline). The organic layer is dried with a suitable drying agent (e.g., sodium sulfate). After distilling away the solvent, the residue is purified (e.g., with silica gel column chromatography) to obtain compound B-2.

(2) Synthesis of Compound B-3

A suitable reagent (e.g., 2,3-dichloro-5,6-dicyano-p-benzoquinone (DDQ) is added to a solution of compound B-2 (e.g., under nitrogen gas flow) at a suitable temperature (e.g., room temperature), and the mixture is stirred at a suitable temperature (e.g., room temperature) for a suitable time (e.g., 12 hours). The reaction is quenched (e.g., by adding water to the reaction solution), and the reaction solution is extracted with a suitable organic solvent (e.g., ethyl acetate). The organic layer is washed (e.g., with saturated saline), and then dried with a suitable drying agent (e.g., anhydrous sodium sulfate). The solvent is distilled away under reduced pressure to obtain compound B-3.

(3) Synthesis of Compound B-4

A suitable reagent (e.g., triethylamine trihydrofluoride) is added to a solution of compound B-3 (e.g., under nitrogen gas flow) at a suitable temperature (e.g., under ice-cooled condition), and the mixture is stirred at a suitable temperature (e.g., room temperature) for a suitable time (e.g., 12 hours). The reaction is quenched (e.g., by adding water to the reaction solution), and the reaction solution is extracted with a suitable organic solvent (e.g., ethyl acetate). The organic layer is washed (e.g., with saturated saline), and then dried with a suitable drying agent (e.g., anhydrous sodium sulfate). The solvent is distilled away under reduced pressure to obtain compound B-4.

(3) Synthesis of Compound B-5

$PG_5X$ (wherein $PG_5$ is a protecting group described herein and X is Cl, Br, or I, such as dimethoxytrityl chloride) is added to a solution of compound B-4 (e.g., under nitrogen gas flow) at a suitable temperature (e.g., room temperature), and the mixture is stirred at a suitable temperature (e.g., room temperature) for a suitable time (e.g., 12 hours). The reaction is quenched (e.g., by adding water to the reaction solution), and the reaction solution is extracted with a suitable organic solvent (e.g., ethyl acetate). The organic layer is washed (e.g., with saturated saline), and then dried with a suitable drying agent (e.g., anhydrous sodium sulfate). The solvent is distilled away under reduced pressure to obtain compound B-5.

(3) Synthesis of Compound B-6

A suitable reagent (e.g., 2-cyanoethyl-N,N,N',N'-tetraisopropylphosphoamidite) is added to a solution of compound B-5 (e.g., under nitrogen gas flow) at a suitable temperature (e.g., room temperature), and the mixture is stirred at a suitable temperature (e.g., room temperature) for a suitable time (e.g., 4 hours) to modify a hydroxy group at position 3' with $P(O)(OPG_6)(OPG_7)$ ($PG_6$ and $PG_7$ are each independently a protecting group described herein). The reaction is quenched (e.g., by adding water to the reaction solution), and the reaction solution is extracted with a suitable organic solvent (e.g., ethyl acetate). The organic layer is washed (e.g., with saturated saline) and then dried with a suitable drying agent (e.g., with anhydrous sodium sulfate). The solvent is distilled away under reduced pressure to obtain compound B-6.

(2) Synthesis of Oligonucleotide Analog

Various oligonucleotide analogs including the nucleoside analog used in the present invention can be synthesized using a known DNA synthesizer. The production of purified oligonucleotide analog can be then confirmed by purifying the resulting oligonucleotide analog using a reverse phase column and analyzing the purity of the product with reverse phase HPLC or MALDI-TOF-MS. One or more nucleoside analogs of the invention can be in an oligonucleotide analog. The nucleoside analog may also be present while being separated at two or more sites in the oligonucleotide analog with one or more naturally occurring nucleotides interposed therebetween. The present invention can synthesize an oligonucleotide analog having the nucleoside analog of the invention introduced at a required position and at a required number (length). The length of an entire oligonucleotide analog is 2 to 50, preferably 8 to 30 nucleotide units.

The oligonucleotide analog used in the present invention is resistant to nuclease degradation, so that the analog can be in the body for a long period after administration thereto. In addition, the oligonucleotide analog of the invention forms a double strand with a sense RNA to inhibit transcription of an in vivo component (protein), which is a pathological factor, into an mRNA. Such an analog is understood to inhibit the proliferation of infected viruses.

In view of the above, the oligonucleotide analog of the invention is expected to be useful as a medicament for treating a disease by inhibiting the function of a gene, including antitumor agents and antiviral agents. In other words, the present invention provides an oligonucleotide analog and a manufacturing intermediate thereof, i.e., nucleoside analog, having stable and excellent antisense or antigene activity or excellent activity as a primer for initiating amplification or a detection agent for a specific gene.

DNA or RNA oligonucleotide analogs (oligonucleotide analogs) prepared by modifying, in various forms, a 2',4'-BNANC monomer that is one of the nucleoside analogs used in the present invention are useful as materials for various physiological/bioactive substances or medicaments, functional materials of double-stranded oligonucleotides for RNA interference or decoy processes, functional materials for DNA chips or molecular beacons targeting a single-stranded nucleic acid such as cDNA, functional materials for various applications in antisense methods (including ribozymes and DNAzymes), antigene methods, and gene homologous recombination methods, materials for high sensitivity analysis of in vivo trace elements in combination with a fluorescent or light emitting substance, or materials for developing reagents used for research such as gene function analysis/elucidation.

The nucleoside analog or oligonucleotide analog of the invention can be used, for example, as a topically administered formulation in combination with a conventionally used additive such as a buffer and/or a stabilizer. As a topical formulation, a conventionally used pharmaceutical carrier can be combined to prepare an ointment, cream, liquid agent, plaster, or the like.

(General synthesis example for oligonucleotides constituting S-TuD)

Oligonucleotides constituting the S-TuD used in the present invention are synthesized with a synthesizer (e.g., nS-8II synthesizer or AKTA oligopilot synthesizer). A controlled pore glass solid phase carrier (e.g., 2'-O-methyl-RNA CPG, Link Technologies), 2'-O-methyl-RNA phosphoramidite having a standard protecting group (examples thereof include, but are not limited to, 5'-O-dimethoxytrityl-N6-benzoyladenosine-2'-O-methyl-3'-O—N,N'-diisopropylphosphoramidite, 5'-O-dimethoxytrityl-N4-acetylcytidine-2'-O-methyl-3'-O—N,N'-diisopropylphosphoramidite, 5'-O-dimethoxytrityl-N2-isobutyrylguanosine-2'-O-methyl-3'-O—N,N'-diisopropylphosphoramidite, and 5'-O-dimethoxytrityluridine-2'-O-methyl-3'-O—N,N'-diisopropylphosphoramidite (which are manufactured by Sigma-Aldrich), and 2',4'-BNA$^{NC}$ (2'-O,4'-C-aminomethylene bridged nucleic acid) thymidine phosphoramidite, i.e., 2'-O,4'-C-aminomethylene-5'-O-dimethoxytrityl-thymidine-N,N'-diisopropylphosphoramidite, 2',4'-BNA$^{NC}$ adenosine phosphoramidite, i.e., 2'-O,4'-C-aminomethylene-5'-O-dimethoxytrityl-N6-benzoyladenosine-N,N'-diisopropylphosphoramidite (which are manufactured by BNA), and LNA (Locked nucleic acid) (2'-O,4'-C-methylene ribonucleic acid) thymidine phosphoramidite, i.e., 2'-O,4'-C-methylene-5'-O-dimethoxytritylthymidine-N,N'-diisopropylphosphoramidite (manufactured by Exiqon)) are used in oligonucleotide synthesis. All phosphoramidites are used in a suitable solvent (e.g., acetonitrile (CH$_3$CN)) at a suitable concentration (e.g., 0.1 M). For 2'-O-methylRNA, BNA, and LNA, a suitable linking/reuse time (e.g., 15 minutes) is used. Examples of activating agents include, but are not limited to, 5-benzylmercapto-tetrazole (0.25 M, Wako Pure Chemical Industries). For example, PO-oxidation uses, but is not limited to, iodine/water/pyridine.

(General Example of Deprotection (General Example of Nucleobase Deprotection))

After the completion of synthesis, the synthesized carrier is transferred to a suitable container (e.g., glass bottle). Oligonucleotides are cleaved from the carrier by deprotecting a base and a phosphoric acid group at a suitable temperature (e.g., 45° C.) for a suitable time (e.g., 13 hours) using 15 mL of a mixture of equal parts of aqueous 40% methylamine solution and 33% methylamine ethanol solution for 1 g of carrier. The step of deprotecting a base and the step of deprotecting a phosphoric acid group may be the same or different steps. An ethanol ammonium mixture is then filtered and placed in a suitable container (e.g., new 250 mL bottle). The carrier is washed (e.g., with 2×40 mL of ethanol/water (1:1 v/v)). The solvent is distilled away for exsiccation (e.g., using a rotary evaporator (roto-vap)).

(General Example for HPLC Purification)

Oligonucleotides are purified by HPLC (e.g., reverse phase ion pair HPLC with a Source 15 RPC gel column). Examples of buffer include, but are not limited to, 5% CH$_3$CN, 0.1 M triethylamine acetic acid buffer (pH 7.0) (buffer A) and 90% CH$_3$CN, 0.1 M triethylamine acetic acid buffer (pH 7.0) (buffer B). Fractions comprising a full-length oligonucleotide are pooled while retaining a protecting group (e.g., dimethoxytrityl group) at the 5' end and are subjected to the next purification. The oligonucleotide pool is then purified by HPLC (e.g., Source 30Q anion pair HPLC). Examples of solution and buffer include, but are not limited to, 0.6% trifluoroacetate (solution A), 20 mM sodium phosphate buffer (pH 7.5) (buffer C), and 2M sodium chloride (buffer D) in 20 mM sodium phosphate buffer. After removing the protecting group at the 5' end, fractions comprising a full-length oligonucleotide are pooled, desalinated, and then lyophilized. The compound is ultimately analyzed, for example, with MALDI-TOF/MS and reverse phase HPLC (e.g., ion pair reverse phase HPLC of X-Bridge).

(General Example of Double-Strand Formation)

After a purified single-stranded oligonucleotide is dissolved into a suitable solvent (e.g., distilled water), the oligonucleotide concentration is determined (e.g., by measuring absorbance using a UV spectrophotometer). Each complementary strand is mixed to be at an equimolar concentration by using the determined concentration and is heated at a suitable temperature (e.g., 95° C.) for a suitable time (e.g., 10 minutes) then gradually cooled to allow the formation of a double strand. Double-strand formation is confirmed by, for example, non-denaturing gel electrophoresis.

A nucleic acid may also comprise a conjugant at an end. Examples of a conjugant include lipophilic substances, terpene, protein binding substances, vitamins, carbohydrates, retinoids, peptides, and the like.

(Other Special Forms of Single Stranded RNA)

The miRNA inhibiting complex used herein can be designed to be comprised of a straight single-stranded nucleic acid (FIG. 3). The present invention relates especially to a complex in which all MBSes are aggregated to one side (right side in FIG. 3) of a double-stranded structure (stem I in FIG. 2), while each strand of the double-stranded structure is structured to be closed on that side (i.e., linked by a sequence comprising an MBS), and both ends of a single-stranded RNA are on the opposite side of the double-stranded structure (FIG. 3). A sequence comprising an MBS may comprise an additional double-stranded structure (stem II, III, or the like in FIG. 3). The length of a single-stranded RNA may be appropriately determined. Examples thereof include 500 bases or less, preferably 450 bases or less, 420 bases or less, 400 bases or less, 380 bases or less, 360 bases or less, 340 bases or less, 320 bases or less, 300 bases or less, 280 bases or less, 260 bases or less, 240 bases or less, 220 bases or less, 200 bases or less, 180 bases or less, 160 bases or less, 140 bases or less, 120 bases or less, 100 bases or less, or 80 bases or less. Examples of the length of a single-stranded RNA forming a complex with two MBSes and two double-stranded structures include 60 to 300 bases, preferably 70 to 250 bases, 80 to 200 bases, 90 to 180 bases, or 100 to 150 bases. A first double-stranded structure (double-stranded structure close to both ends of a single-stranded RNA) can be, for example, 15 to 30 bp, preferably 16 to 28 bp, preferably 17 to 25 bp, preferably 17 to 24 bp, such as 17 bp, 18 bp, 19 bp, 20 bp, 21 bp, 22 bp, 23 bp, or 24 bp. A second double-stranded structure (additional double-stranded structure comprised in a sequence comprising an MBS) may be shorter than the first double-stranded structure in order to materialize a compact size of the whole complex. Examples of the length thereof include 4 bp to 20 bp, such as 5 bp to 15 bp, 5 bp to 12 bp, 5 bp to 10 bp, 6 bp to 9 bp, and 7 bp to 8 bp.

The present invention also relates to an RNA constituting the miRNA inhibiting complex used herein (wherein the RNA includes naturally-occurring RNAs and nucleic acid analogs), comprising a BNA. The complex of the invention can be constructed by intramolecular annealing of RNA when an miRNA inhibiting RNA complex is comprised of one molecule of the RNA, or by annealing RNAs when it is comprised of two or more RNA molecules. These RNAs can be appropriately synthesized. For example, a desired RNA can be manufactured by chemical synthesis of RNA.

A nucleic acid encoding at least one MBS may comprise two or more MBSes. A pair or a set of more complementary sequences that can form a double-stranded structure may be comprised in a contiguous sequence. Examples of such nucleic acids include nucleic acids comprising at least one MBS on each of the ends of a pair of complementary sequences, and the pair of complementary sequences forming at least one double-stranded structure. Such a nucleic acid specifically comprises a pair of complementary sequences that can form a stem between two MBSes. The stem corresponds to the aforementioned second double-stranded structure. Alternatively, a sequence forming a G-quadruplex instead of a second double-stranded structure may be comprised.

Said nucleic acid may comprise two or more structural units comprising a pair of complementary sequences that can form a double-stranded structure between two MBSes. Multiple such structural units can be comprised in a nested form. Between a pair of complementary sequences that can form a double-stranded structure between a pair of MBSes, there can be a sequence comprising an additional pair of MBSes and a pair of complementary sequences that can form a double-stranded structure therebetween (#15 or #16 in FIG. 3 or the like). The sequences of MBSes may be the same or different.

Insertion of such a nucleic acid between the aforementioned pair of complementary sequences results in a nucleic acid with a structure, to which a sequence with a structure of MBS-sequence forming a second double-stranded structure-MBS is inserted between a pair of complementary sequences that form a first double-stranded structure. A specific example thereof is a nucleic acid with a structure to which a sequence with a structure of MBS-pair of complementary sequences forming a second double-stranded structure-MBS is inserted. A nucleic acid consisting of two double-stranded structures and a pair of opposing single strands (each comprising an MBS) therebetween is compact and exhibits sufficient miRNA inhibiting activity.

A pair of complementary sequences that can form a double-stranded structure and MBSes can be linked via an appropriate linker or a spacer. The length of a linker or a spacer is described herein. Further, a complementary sequence may be linked via a linker or a spacer. When a double strand is formed, the linker or spacer forms a loop, thus forming a stem loop with the double strand. The length of a loop may be appropriately adjusted. The details thereof are described herein. Alternatively, a sequence forming a G-quadruplex can be appropriately used instead of a double strand.

One aspect of the invention provides a nucleic acid molecule comprising: the sequences of 5'-CAGUGUU-3' and 5'-CAGUAUU-3' and at least one bridged nucleic acid (BNA). One aspect of the invention provides a nucleic acid molecule comprising: two miRNA binding sequences, one of the miRNA binding sequences comprising 5'-CAGUGUU-3' or 5'-CAGUAUU-3', and the other miRNA binding sequence comprising 5'-CAGUGUU-3' or 5'-CAGUAUU-3'; and at least one bridged nucleic acid (BNA). One embodiment of the invention provides a nucleic acid molecule comprising: two miRNA binding sequences, one of the miRNA binding sequences comprising 5'-CAGUGUU-3' and the other miRNA binding sequence comprising 5'-CAGUAUU-3'; and at least one bridged nucleic acid (BNA).

One embodiment of the invention provides a nucleic acid molecule comprising an miRNA binding sequence comprising the sequence of SEQ ID NO: 1 and an miRNA binding sequence comprising the sequence of SEQ ID NO: 2. Still another embodiment of the invention is a nucleic acid molecule comprising the sequence of SEQ ID NO: 9 and the sequence of SEQ ID NO: 10.

The nucleic acid molecule or miRNA inhibiting complex of the invention can comprise any number of the BNAs used in the present invention at any position. For example, one nucleic acid molecule or miRNA inhibiting complex can comprise 1, 2, 3, 4, 5, 6, 7, 8, 9, 10, 11, 12, 13, 14, 15, 16, 17, 18, 19, 20, or more BNAs. As described above, an effect can be exerted even when comprising only one BNA. A BNA can be comprised in an MBS and/or double-stranded structure. Improvement in serum stability and capability to inhibit miRNAs can be expected even if one of MBS and double-stranded structure comprises a BNA. In a particularly preferred embodiment, both an MBS and double-stranded structure comprise a BNA. For example, miR-200C can be successfully suppressed with a nucleic acid molecule with a BNA modification at a position shown in FIG. 10 (lower case letter in the Figure). The same suppression effect is also observed in miRNAs other than miR-200C such as miR21.

(Inhibition of miRNA)

The present invention provides a composition comprising the nucleic acid molecule described herein and a method using the same, including those described above. In a preferred embodiment, a composition is for preventing or treating tumor. A method for preventing or treating tumor using said composition is also provided.

In one embodiment, the tumor targeted by the present invention is carcinoma. In another embodiment, the tumor targeted by the present invention is colon cancer, lung cancer, or breast cancer. The composition of the invention can also be used for promoting epithelial-mesenchymal transition of the tumor. The present invention also provides a composition for such an application and a method for such use. One aspect of the invention relates to a composition comprising an miRNA inhibiting complex wherein the miRNA inhibiting complex is in a form contained in a carrier for nucleic acid delivery. Use of a suitable carrier promotes serum stability of the miRNA inhibiting complex and delivery thereof to a target tissue, and is especially useful for therapeutic and prophylactic use.

The inventors have found that a significant change in a subpopulation of cancer cells including induction of epithelial-mesenchymal transition (EMT) is induced when tetracycline inducible expression systems were combined for a specific and potent inhibitor for a target miRNA, TuD (Tough Decoy) RNA, and applied the system to simultaneously suppress miR-200c and miR-141 expression in a human colon cancer cell strain by TuD expression.

For the effect of miR-200 family inhibition on tumor cells, when a specific subpopulation in a cell population of triple negative breast cancer cells was identified based on a cell surface marker to observe the mode of such cells interconverting among subpopulations, a subpopulation with an epithelial trait was unexpectedly found to exhibit significantly higher tumorigenicity.

Furthermore, it has been elucidated that tumorigenicity significantly decreases when a plurality of members of the miR-200 family are simultaneously inhibited in the tumor cells. Further, simultaneous inhibition of a plurality of miR-200 family members in a subpopulation of ESA(−) tumor cells results in no tumorigenicity being observed, which is already low to begin with.

These results demonstrate that miR-200 family members are deeply involved in tumorigenicity, especially growth of primary tumor at the primary lesion, and tumorigenicity can be reduced very efficiently by effectively inhibiting miR-200 family members. It has been understood that cells with less differentiated mesenchymal phenotype carrying cells among tumor cells have higher tumorigenicity. However, the inventors have revealed that epithelial phenotype carrying cells contribute significantly to tumorigenicity, and have demonstrated that tumor growth can be suppressed by inhibiting miR-200 family members promoting EMT in tumor to tip the balance of a tumor cell population from epithelial to mesenchymal. In other words, some aspects of the invention demonstrate that growth of primary tumor can be effectively suppressed, and regression of existing tumor can be materialized, through inhibition of miR-200 family members. In particular, the present invention is capable of not only suppressing tumor by targeting cancer stem cells, but also preventing the generation of cancer stem cells from non-cancer cells at the same time.

The present invention can also target and inhibit miRNAs described below besides miR-200 family members. It is understood that desired treatment can be materialized, including suppression of tumor growth, tumor regression, prevention of generation of cancer stem cells from non-cancer stem cells, and the like in accordance with the targeted miRNA by such miRNA inhibition. The inhibiting complex of the invention can be designed to bind to any miRNA exemplified herein.

miR-205 suppresses EMT by suppressing Zeb1 and Zeb2 in the same manner as the miR-200 family (Nature Cell Biology volume 10, pages 593-601 (2008)). It is also reported that miR-205 can be a diagnostic marker because the expression thereof is elevated in lung cancer (Biomed Pharmacother. 2017 July; 91: 823-830.) For this reason, it is understood that miR-205 can be targeted in the same manner as the miR-200 family members.

Expression of miR-21 is abnormally elevated in various types of cancer such as colon cancer, lung cancer, breast cancer, pancreatic cancer, liver cancer, glioblastoma, skin cancer, thyroid cancer, cervical cancer, and hemocyte system cancer (DOI: 10.1111/j.1582-4934.2008.00556.x) Inhibition of miR-21 in liver cancer cells suppresses cell growth, motility, and capability to infiltrate. Inhibition of miR-21 in glioblastoma cells induces apoptosis. miR-21 contributes to chemoresistance in breast cancer, colon cancer, lung cancer, pancreatic cancer, prostate cancer, liver cancer, ovarian cancer, glioma, head and neck cancer, gastric cancer, and bladder cancer (Biomed Rep. 2016 October; 5(4): 395-402.)

Examples of miRNAs of the miR-17-92 cluster include miR-17, miR-18a, miR-19a, miR-20a, miR-19b-1, and miR-92a-1, which are in the 13th chromosome as a cluster. Elevated expression of an miRNA in the miR-17-92 cluster is observed in lung cancer, breast cancer, colon cancer, pancreatic cancer, prostate cancer, thyroid cancer, and leukemia (Front Med (Lausanne). 2015; 2: 64)

miR-155 contributes to the malignant trait of cancer in glioma, lung cancer, colon cancer, liver cancer, breast cancer, osteosarcoma, oral squamous cell carcinoma, and lymphoma. miR-155 also contributes to resistance to anticancer chemotherapy or radiation therapy in lung cancer, colon cancer, prostate cancer, breast cancer, or the like (Bayraktar, R. & Van Roosbroeck, K. Cancer Metastasis Rev (2018) 37: 33.). In addition, it is reported with regard to miR-155 that: expression is abnormally elevated in colon cancer, lung cancer, and breast cancer (Proc Natl Acad Sci USA 2006; 103: 2257-61.); suppression of oncogenesis was observed when anti-miR-155 was administered to breast cancer cell strain MDA-MB-231 and transplanted into mice (DOI: 10.1158/0008-5472.CAN-09-4250); and tumor growth is inhibited if lung cancer cell with miR-155 suppressed with an inhibitor is transplanted, and the inhibitory effect is enhanced with concomitant use of miR-21 inhibition (Oncotarget. 2016 Dec. 20; 7(51): 84508-84519.)

It is reported with regard to miR-133a that the prognosis is poor if miR-133a is highly expressed in osteosarcoma, and concomitant use of miR-133a inhibition and chemotherapy in osteosarcoma carrying mice suppressed lung metastasis and extended the overall survival (Stem Cells. 2014 April; 32(4): 959-73.)

It is reported with regard to miR-196b that the prognosis of the miR-196b high expression group is poor in pancreatic cancer (Carcinogenesis. 2017 Apr. 1; 38(4):425-431.)

It is reported with regard to miR-197 that a lung cancer cell strain with miR-197 inhibited suppresses tumor growth after transplantation to mice (Cell Death and Differentiation (2014) 21, 774-782).

It is reported that miR-125b contributes to molecule targeted therapeutic drug resistance in gastric cancer, and the prognosis is poor in high expression groups (Exp Ther Med. 2017 July; 14(1): 657-663.)

It is reported that miR-135b is highly expressed in colon cancer, and the prognosis is poor in high expression groups (Cancer Cell. 2014 Apr. 14; 25(4): 469-483.), and prognosis is poor for miR-135b high expression groups in lung cancer, and tumor growth is suppressed when an inhibitor is administered to lung cancer cell strain transplanted mice (Nat Commun. 2013; 4:1877. doi: 10.1038/ncomms2876.)

It is reported that miR-106a is highly expressed in lung cancer and the prognosis is poor, and lung cancer cell growth is suppressed if miR-106a is inhibited in the cell (Int J Clin Exp Pathol. 2015 Apr. 1; 8(4): 3827-34.); and the prognosis is poor for miR-106a high expression groups in colon cancer (Med Mol Morphol. 2017 June; 50(2): 76-85.)

It is reported with regard to miR-10a/10b that cell growth is suppressed if miR-10a of a lung cancer cell strain is inhibited (Oncotarget. 2015 Oct. 6; 6(30):30239-50.), and the prognosis is poor for the miR-10b high expression group in lung cancer (Clin Transl Oncol (2015) 17: 209-214).

It is reported that the expression of miR-146a is elevated in osteosarcoma, and the prognosis is poor for high expression groups, and growth in mice is suppressed for osteosarcoma with miR-146a inhibited (Oncotarget. 2017; 8: 74276-74286.)

It is reported with regard to miR-182 that cell growth and colonization capability are suppressed if miR-182 is inhibited in colon cancer cells (Oncol Rep. 2015 May; 33(5): 2592-8.)

It is reported with regard to miR-96 that cell growth is suppressed if miR-96 is inhibited in prostate cancer cells (Oncogene. 2015 Sep. 3; 34(36): 4767-76.)

A preferred embodiment of the invention is characterized by inhibiting both at least one miRNA comprising 5'-AACACUG-3' as a seed sequence and at least one miRNA comprising 5'-AAUACUG-3' as a seed sequence, whereby tumor is suppressed. In this regard, suppression of tumor can be suppression of tumorigenicity of tumor cells, suppression of formation or growth of tumor, or regression of tumor. These can be measured, for example, by using tumor formation (e.g., frequency thereof), size, growth rate or the like in vivo when tumor cells are transplanted into an individual as an indicator. An miRNA binding sequence comprises 5'-CAGUGUU-3' and/or 5'-CAGUAUU-3'. This enables inhibition of at least one miRNA comprising 5'-AACACUG-3' as a seed sequence or at least one miRNA comprising 5'-AAUACUG-3' as a seed sequence. An miRNA inhibiting complex comprises two miRNA biding sequences, one of the miRNA binding sequences comprising 5'-CAGUGUU-3' and the other miRNA binding sequence comprising 5'-CAGUAUU-3'. This is advantageous in inhibiting both at least one miRNA comprising 5'-AACACUG-3' as a seed sequence and at least one miRNA comprising 5'-AAUACUG-3' as a seed sequence.

The tumor suppression according to the present invention is characterized by being capable of not only suppressing tumor by targeting cancer stem cells, but also preventing the generation of cancer stem cells from non-cancer cells at the same time. In other words, tumor suppression in the invention includes (i) suppression of tumor formation of cancer stem cells, and (ii) suppression of the generation of cancer stem cells from non-cancer stem cells. Specifically, tumor suppression according to the present invention not only suppresses tumor formation due to a subpopulation with a relatively elevated tumorigenicity among the tumor cell population, but also exerts an effect of converting cells belonging to the subpopulation with relatively elevated tumorigenicity to a cell of a subpopulation with a relatively low tumorigenicity, and suppresses cells belonging to a subpopulation with a relatively low tumorigenicity from converting to cells with relatively elevated tumorigenicity. This enables not only suppression of tumorigenicity in existing cancer cells with high tumorigenicity (e.g., cancer stem cells), but also conversion of such cancer cells into cancer cells with lower tumorigenicity (non-cancer stem cells) and suppression of conversion from cancer cells with low tumorigenicity into cancer cells with high tumorigenicity. Tumor suppression of the invention, which is not only capable of targeting cancer stem cells, but also preventing the generation of cancer stem cells from non-cancer stem cells at the same time in this manner is highly useful in clinical application. The tumor suppression of the invention is expected to prophylactically suppress tumor formation at the initial stage before and after onset of cancer. In other words, "suppression of tumor" in the present invention is, in a preferred embodiment, suppression achieving both suppression of tumor formation in a tumor cell subpopulation with elevated tumorigenicity in a tumor cell population and suppression of the generation of a tumor cell subpopulation with elevated tumorigenicity.

A tumor cell population can be divided into subpopulations using a desirable marker or the like. For example, a cell population can be divided into subpopulations using an epithelial marker as an indicator. For examples, any epithelial marker can be selected from, but is not limited to, ESA (epithelial specific antigen), CDH1 (Cadherin-1), CDH3 (Cadherin-3), ESRP1 (epithelial splicing regulatory protein 1), and the like, and is preferably ESA. These markers can also be combined and used. If an epithelial marker positive subpopulation has relatively higher tumorigenicity than a negative subpopulation, the positive subpopulation is a subpopulation with relatively elevated tumorigenicity (cell group with high tumorigenicity), and the negative subpopulation is a subpopulation with relatively low tumorigenicity (cell group with low tumorigenicity).

A seed sequence refers to a sequence from the 2nd to 8th base from the 5' end of an miRNA. miRNAs comprising 5'-AACACUG-3' as a seed sequence include miR-200a (5'-UAACACUGUCUGGUAACGAUGU-3', SEQ ID NO: 13) and miR-141 (5'-UAACACUGUCUG-GUAAAGAUGG-3', SEQ ID NO: 14). miRNAs including 5'-AAUACUG-3' as a seed sequence include miR-200b (5'-UAAUACUGCCUGGUAAUGAUGA-3', SEQ ID NO: 15), miR-200c (5'-UAAUACUGCCGG-GUAAUGAUGGA-3', SEQ ID NO: 16), and miR-429 (5'-UAAUACUGUCUGGUAAAACCGU-3', SEQ ID NO: 17).

Inhibition using only an inhibitor of miR-200c comprising 5'-AAUACUG-3' as a seed sequence can hardly suppress the activity of miR-141 comprising 5'-AACACUG-3' as a seed sequence. This indicates that an inhibitor for one miRNA cannot effectively inhibit another miRNA due to a difference in one base in the seed sequences thereof. The significant antitumor activity shown in the present invention can be exerted by combining two types of miRNAs that inhibit each miRNA.

Another embodiment of the invention is characterized by inhibiting at least one miRNA comprising 5'-AGCUUAU-3' as a seed sequence, whereby tumor is suppressed. Examples of such miRNAs include miR-21 (5'-UAGCUUAUCA-GACUGAUGUUGA-3', SEQ ID NO: 41).

The method of the invention preferably inhibits at least miR-200c and miR-141. Activity of each miRNA in inhibited cells is for example ⅓ or less, preferably ¼ or less, ⅕ or less, ⅙ or less, ⅐ or less, ⅛ or less, or ⅑ or less, and more preferably 10% or less, 8% or less, 5% or less, or 3% or less, compared to the activity of each miRNA with no inhibition. More preferably, the method of the invention inhibits all of miR-200a, miR-200b, miR-200c, miR-141, and miR-429. The activity of each miRNA is for example ⅓ or less, preferably ¼ or less, ⅕ or less, ⅙ or less, ⅐ or less, ⅛ or less, or ⅑ or less, and more preferably 10% or less, 8% or less, 5% or less, or 3% or less, compared to the activity of each miRNA with no inhibition. Preferably, the method of the invention inhibits all members of the miR-200 family. The activity can be measured using an assay known to those skilled in the art such as a reporter assay using luciferase (e.g., assay using Dual-Luciferase® Reporter Assay System (Promega).

An miRNA inhibiting complex that is especially useful for inhibition of miRNAs is disclosed elsewhere herein. In the present invention, S-TuD can be suitably used as an miRNA inhibitor. As used herein, S-TuD refers to an miRNA inhibitor consisting of a structure with a pair of strands, each comprising at least one miRNA binding sequence, wherein both ends of the pair of strands comprising an miRNA binding sequence are bound to one end of each of a pair of multi-strands (e.g., double strand and/or quadruple strand) so that they are sandwiched by the pair of multi-strands. The miRNA inhibitor can be comprised of an RNA, or other nucleic acids or nucleic acid analogs or a combination thereof.

Even if inhibition of at least one miRNA comprising 5'-AACACUG-3' as a seed sequence and inhibition of at least one miRNA comprising 5'-AAUACUG-3' as a seed sequence use different inhibitors or use one inhibitor for both inhibition, it is preferable to have a site for inhibiting at least one miRNA comprising 5'-AACACUG-3' as a seed sequence separately from a site for inhibiting at least one miRNA comprising 5'-AAUACUG-3' as a seed sequence for inhibition at two different inhibition sites. This is known in the present invention as inhibition by such an miRNA inhibitor of both at least one miRNA (first miRNA) comprising 5'-AACACUG-3' as a seed sequence and at least one miRNA (second miRNA) comprising 5'-AAUACUG-3' as a seed sequence using different inhibition sites. In such a case, the inhibition moiety of an miRNA inhibitor that inhibits the first miRNA is different from the inhibition moiety of the miRNA inhibitor that inhibits the second miRNA. Specifically, the inhibition moiety of the miRNA inhibitor that inhibits the first miRNA comprises a sequence complementary to a seed sequence of the first miRNA, and the inhibition moiety of the miRNA inhibitor that inhibits the second miRNA comprises a sequence complementary to a seed sequence of the second miRNA. Examples of such inhibition include miRNA inhibition using an miRNA inhibitor molecule comprising a sequence complementary to a seed sequence of the first miRNA and an miRNA inhibitor molecule comprising a sequence complementary to a seed sequence of the second miRNA. Another example includes miRNA inhibition using an miRNA inhibitor comprising an miRNA inhibition moiety comprising a sequence complementary to a seed sequence of the first miRNA and an miRNA inhibition moiety comprising a sequence complementary to a seed sequence of the second miRNA in the same molecule.

An miRNA inhibitor having two or more miRNA inhibition sites, each of which is designed to target different moieties of an miRNA (e.g., to target different miRNAs) in this manner is called a hybrid miRNA inhibitor in the present invention. The miRNA inhibitor of the invention is preferably a hybrid miRNA inhibitor having an inhibition site for at least one miRNA comprising 5'-AACACUG-3' as a seed sequence and an inhibition site for at least one miRNA comprising 5'-AAUACUG-3' as a seed sequence.

While cancer targeted for suppression in the present invention is not particularly limited, cancer derived from the epithelium or at least partially having an epithelial trait such as carcinoma is preferable. Cancer targeted for suppression in the present invention is preferably cancer comprising at least a population of cells expressing an epithelial marker, more preferably cancer comprising a population of cells expressing an epithelial marker as the main population of cells (i.e., cancer with less than half of the population of cells not expressing any epithelial marker). For example, any epithelial marker can be selected from, but is not limited to, ESA (epithelial specific antigen), CDH1 (Cadherin-1), CDH3 (Cadherin-3), ESRP1 (epithelial splicing regulatory protein 1), and the like, and more preferably ESA. These markers can also be combined and used. Such cancer comprises cells expressing any of the epithelial marker (e.g., ESA) (e.g., ESA+cells) at 0.3% or more, preferably 0.5% or more, 1% or more, 2% or more, 3% or more, 5% or more, 7% or more, 10% or more, 15% or more, 20% or more, 25% or more, 30% or more, 40% or more, 50% or more, 60% or more, 70% or more, 80% or more, or 90% or more. The present invention provides a method of examining cancer comprising checking that tumor cells comprise an epithelial marker positive cell. Preferably, epithelial-mesenchymal transition is promoted and/or mesenchymal-epithelial transition is suppressed in cancer targeted for suppression in the present invention by inhibiting both at least one miRNA comprising 5'-AACACUG-3' as a seed sequence and at least one miRNA comprising 5'-AAUACUG-3' as a seed sequence. Preferably, mesenchymal-epithelial transition is promoted and/or epithelial-mesenchymal transition is suppressed in cancer targeted for suppression in the present invention by allowing expressing of both at least one miRNA comprising 5'-AACACUG-3' as a seed sequence and at least one miRNA comprising 5'-AAUACUG-3' as a seed sequence. Preferably, epithelial-mesenchymal transition is promoted and/or mesenchymal-epithelial transition is suppressed in cancer targeted for suppression in the present invention by inhibiting miR-200c and miR-141. Preferably, mesenchymal-epithelial transition is promoted and/or epithelial-mesenchymal transition is suppressed in cancer targeted for suppression in the present invention by allowing expression of both miR-200c and miR-141.

Although not essential, tumor cells can be confirmed as at least comprising a population of cells expressing an epithelial cell prior to suppression of tumor. In other words, the method of the invention comprises, in one embodiment thereof, confirming that tumor cells comprise at least a population of cells expressing an epithelial marker prior to suppression of tumor. For example, the method of the invention comprises, in one embodiment thereof, confirming that tumor cells comprise at least a population of cells expressing an epithelial marker prior to suppression of tumor and suppressing the tumor confirmed to be promoted. Although not essential, epithelial-mesenchymal transition can be confirmed as being promoted by inhibition of the miRNA in tumor cells prior to suppression of tumor. In other words, the method of the invention comprises, in one embodiment thereof, confirming that epithelial-mesenchymal transition is promoted by inhibition of the miRNA in tumor cells. For example, the method of the invention comprises, in one embodiment thereof, confirming that epithelial-mesenchymal transition is promoted by inhibition of the miRNA in tumor cells prior to suppression of tumor, and suppressing the tumor confirmed to be promoted. However, the present invention is not limited to such methods in any manner. The present invention also provides a method of examining cancer comprising confirming that epithelial-mesenchymal transition is promoted by inhibition of the miRNA in tumor cells.

The cancer targeted for suppression in the present invention can also be, for example, cancer comprising a subpopulation ($sp^E$) having an epithelial trait and a subpopulation having a mesenchymal trait ($sp^M$). Such cancer comprises, for example, a subpopulation of epithelial marker positive cells and a subpopulation of epithelial marker negative (or low expression) or mesenchymal marker positive cells. Preferably, cancer targeted for suppression in the present invention comprises each of a subpopulation of cells expressing an epithelial marker and a subpopulation of epithelial marker negative or low expression (or mesenchymal marker positive) cells at 0.3% or more, preferably 0.5% or more, 1% or more, 2% or more, 3% or more, 5% or more, 7% or more, 10% or more, 15% or more, 20% or more, 25% or more, or 30% or more. The ratio of a subpopulation can be determined directly from collected cancer cells or by culturing cancer cells in a desirable medium. For example, a DMEM medium, Ham's F-12 medium, or the like can be used. An assay can be conducted by adding 5-10% fetal bovine serum (FBS) or the like when appropriate. The ratio of a subpopulation of cells expressing an epithelial marker in tumor cells to a subpopulation of epithelial marker negative or low expression (or mesenchymal marker positive) cells can be found prior to suppression of tumor, but the present invention is not limited thereto.

The cancer targeted for suppression in the present invention preferably comprises cancer stem cells in a subpopulation ($sp^E$) having an epithelial trait. Cancer stem cells refer to cells having the ability to form a tumorsphere in a tumorsphere formation assay, or cells having the ability to form tumor in a tumor formation experiment using an animal. Cancer stem cells belonging to a subpopulation ($sp^E$) having an epithelial trait are called epithelial trait cancer stem cells or epithelial cancer stem cells. A cell population can be confirmed as comprising cancer stem cells by confirming the population as being tumorigenic. For example, this can be confirmed by assaying formation of tumorsphere in accordance with procedures known to those skilled in the art or by testing oncogenesis after transplanting cells into mice or the like.

A test can be conducted to confirm whether target tumor comprises epithelial trait cancer stem cells prior to suppression of tumor. In other words, the method of the invention comprises, in one embodiment thereof, confirming that targeted cancer comprises epithelial trait cancer stem cells prior to suppression of tumor. For example, the method of the invention comprises, in one embodiment thereof, confirming that targeted cancer comprises epithelial trait cancer stem cells prior to suppression of tumor and suppressing the confirmed cancer in accordance with the method of the invention described above.

For cancer targeted for suppression in the present invention, cancer with tumorigenicity of a subpopulation ($sp^E$) having an epithelial trait higher than tumorigenicity of the rest of the population (e.g., subpopulation having a mesenchymal trait; $sp^M$) or the entire group of cancer cells is preferable. Such cancer is referred to as epithelial trait subpopulation tumorigenic tumor ($sp^E$ tumorigenic tumor) or epithelial trait tumorigenic tumor herein. Oncogenicity can be measured, for example, by assaying formation of tumorsphere in accordance with procedures known to those skilled in the art or by transplanting cells into mice or the like to measure the presence/absence of tumor formation or the tumor size. For example, a subpopulation ($sp^E$) having an epithelial trait is separated from tumor cells. The rest of the population (e.g., subpopulation having a mesenchymal trait; $sp^M$) or the entire group of cancer cells is used as a control group to conduct an assay of tumorigenicity with the same number of cell. If tumorigenicity of $sp^E$ is higher, the cancer is determined as epithelial trait tumorigenic tumor with higher tumorigenicity in a subpopulation ($sp^E$) having an epithelial trait than the rest of the population or the entire group of cancer cells. A subpopulation having an epithelial trait can be separated/identified using an epithelial marker as appropriate. Any epithelial marker can be selected from, for example, ESA, CDH1, CDH3, ESRP1, and the like as described above. The present invention also relates to a method of testing cancer and a method of classifying cancer comprising confirming that tumorigenicity in a subpopulation ($sp^E$) having an epithelial trait is higher than a subpopulation without an epithelial trait or the entire group of cancer cells in tumor.

In the present invention, tumorigenicity of a subpopulation ($sp^E$) having an epithelial trait can be confirmed to be higher than tumorigenicity in the rest of the population (e.g., subpopulation having a mesenchymal trait; $sp^M$) or the entire group of cancer cells in the target tumor prior to suppression of tumor. In other words, the method of the invention comprises, in one embodiment thereof, confirming that tumorigenicity of a subpopulation ($sp^E$) having an epithelial trait is higher than tumorigenicity in the rest of the population (e.g., subpopulation having a mesenchymal trait; $sp^M$) or the entire group of cancer cells in the target tumor prior to suppression of tumor. For example, the method of the invention comprises, in one embodiment thereof, confirming that tumorigenicity of a subpopulation ($sp^E$) having an epithelial trait is higher than tumorigenicity in the rest of the population (e.g., subpopulation having a mesenchymal trait; $sp^M$) or the entire group of cancer cells in the target tumor prior to suppression of tumor, and suppressing the tumor confirmed to be high in accordance with the method of the invention described above.

The cancer targeted for suppression in the present invention is preferably cancer with positive expression of at least one miRNA comprising 5'-AACACUG-3' as a seed sequence or at least one miRNA comprising 5'-AAUACUG-3' as a seed sequence. Targeted cancer can be cancer with positive expression of both at least one miRNA comprising 5'-AACACUG-3' as a seed sequence and at least one miRNA comprising 5'-AAUACUG-3' as a seed sequence (miR-200 two subfamily positive tumor). Specifically, such cancer can be cancer that is positive for at least one of miR-200a, miR-141, miR-200b, miR-200c, and miR-429. Furthermore, cancer can be cancer with at least one of miR-200a and miR-141 (more preferably miR-141) and at least one of miR-200b, miR-200c, and miR-429 (more preferably miR-200c) positive. The present invention can confirm that target tumor is miR-200 subfamily positive tumor, more preferably miR-200 two subfamily positive tumor prior to suppression of tumor. In other words, the method of the invention comprises, in one embodiment thereof, confirming that expression of at least one miRNA comprising 5'-AACACUG-3' as a seed sequence and/or at least one miRNA comprising 5'-AAUACUG-3' as a seed sequence is positive in target tumor prior to suppression of tumor. For example, the method of the invention comprises, in one embodiment thereof, confirming that expression of at least one miRNA comprising 5'-AACACUG-3' as a seed sequence and/or at least one miRNA comprising 5'-AAUACUG-3' as a seed sequence is positive in target tumor prior to suppression of tumor and suppressing the confirmed tumor in accordance with the method of the invention described above.

Preferably, cancer targeted for suppression in the present invention can be cancer with positive expression of at least one miRNA comprising 5'-AGCUUAU-3' as a seed sequence. Specifically, such cancer can be cancer that is at least miR-21 positive. In the present invention, target tumor can be confirmed to be miR-21 subfamily positive tumor prior to suppression of tumor. In other words, the method of the invention comprises, as one embodiment thereof, confirming that expression of at least one miRNA comprising 5'-AGCUUAU-3' as a seed sequence is positive in target tumor prior to suppression of the tumor. For example, the method of the present invention comprises, as one embodiment thereof, confirming that expression of at least one miRNA comprising 5'-AGCUUAU-3' as a seed sequence is positive in target tumor prior to suppression of the tumor and suppressing the confirmed tumor in accordance with the method of the invention described above.

Cancer targeted for suppression in the present invention is preferably cancer expressing at least one miR-200 family member (miR-200 gene locus positive tumor, more preferably miR-200 two gene locus positive tumor) from two chromosomal loci of the miR-200 family, preferably each of the two chromosomal loci of the miR-200 family. Specifically, such cancer is cancer with positive expression of at least one of miR-200a, miR-200b, miR-429, miR-200c, and miR-141. Such cancer can be cancer with positive expression of at least one of miR-200a, miR-200b, and miR-429 and at least one of miR-200c and miR-141. In the present invention, target tumor can be confirmed to be miR-200 subfamily positive tumor, more preferably miR-200 two gene locus positive tumor prior to suppression of tumor. In other words, the method of the invention comprises, as one embodiment thereof, confirming that at least one of miR-200a, miR-200b and miR-429 and/or at least one of miR-200c and miR-141 are positive in the target tumor prior to suppression of the tumor. For example, the method of the invention comprises, in one embodiment thereof, confirming that expression of at least one of miR-200a, miR-200b and miR-429 and/or at least one of miR-200c and miR-141 are positive in the target tumor prior to suppression of the tumor, and suppressing the confirmed tumor in accordance with the method of the invention described above.

Cancer targeted for suppression in the present invention specifically includes colon cancer, lung cancer, and breast cancer. Examples of cancer targeted for suppression in the present invention include in particular progesterone receptor (PR), estrogen receptor (ER), or HER2 negative tumor (e.g., breast cancer), more preferably at least progesterone receptor (PR) negative tumor (e.g., breast cancer), and most preferably estrogen receptor, progesterone receptor, and HER2 negative triple negative breast cancer. Cancer targeted for suppression in the present invention includes, but is not limited to, prostate cancer, non-small cell lung cancer (NSCLC), and renal cancer. Cancer targeted for suppression in the present invention is preferably human cancer.

The suppression of tumor in the present invention is especially useful, for example, in suppressing generation of tumor, or suppressing increasing tumor, or the like, and particularly exerts a high effect in suppressing primary tumor. In this regard, primary tumor refers to an organ or tissue from which the tumor originates matches the organ or tissue where the tumor is present. For example, the present invention is especially useful in suppressing growth of breast cancer in breast for breast cancer, growth of colon cancer in the colon for colon cancer, and growth of cancer in the prostate, lung, and kidney for prostate cancer, non-small cell lung cancer, and renal cancer, respectively.

For example, growth/progression of primary tumor is known to have a different mechanism from tumor metastasis. Metastasis requires processes such as separation of cancer cells from the primary lesion and infiltration into vascular system (blood vessel or lymph duct), movement in the vascular system, adhesion to vascular endothelium of the metastasized organ, and infiltration into the metastasized organ. For metastasis to materialize, cancer cells are required to be able to evade and survive from the immune rejection mechanism in all of the processes. Therefore, suppression of metastasis can be achieved if one of the processes can be inhibited, while suppression of primary tumor cannot be achieved unless growth, survival, anti-apoptosis activity, and the like of the primary tumor are inhibited.

The present invention also relates to use of the miRNA inhibitor of the invention for suppressing tumor, and use thereof in the manufacture of an agent for suppressing tumor. In other words, the present invention relates to use of one or more inhibitors that inhibit at least one miRNA comprising 5'-AACACUG-3' as a seed sequence and at least one miRNA comprising 5'-AAUACUG-3' as a seed sequence alone or in combination for suppressing tumor, and use thereof in the manufacture of an agent for suppressing tumor. The present invention also relates to said miRNA inhibitor used for suppressing tumor.

More specifically, the present invention relates to use of one or more miRNA inhibitors for inhibiting at least one miRNA comprising 5'-AACACUG-3' as a seed sequence and at least one miRNA comprising 5'-AAUACUG-3' as a seed sequence alone or in combination in the manufacture of an agent for administering the miRNA inhibitor to suppress tumor. The present invention also relates to use of one or more miRNA inhibitors for inhibiting at least one miRNA comprising 5'-AACACUG-3' as a seed sequence and at least one miRNA comprising 5'-AAUACUG-3' as a seed sequence alone or in combination in the manufacture of an agent for administering the miRNA inhibitor to promote epithelial-mesenchymal transition and/or suppress mesenchymal-epithelial transition of tumor cells. It is preferably to inhibit at least miR-200c and miR-141, more preferably to inhibit all of the miR-200 family members consisting of miR-200a, miR-200b, miR-200c, miR-141, and miR-429 for the alone or in combination. In this regard, inhibition of an miRNA refers to direct inhibition, preferably by an inhibitor binding to (interacting with) a target miRNA. In other words, direct inhibition by an miRNA inhibitor binding to (interacting with) miR-200c and miR-141 is preferred in the present invention, more preferably direct inhibition by an miRNA inhibitor interacting with all of the miR-200 family members consisting of miR-200a, miR-200b, miR-200c, miR-141, and miR-429.

(Medicament)

In another aspect, the present invention provides a medicament comprising the complex of the present invention.

In one embodiment, the miRNA inhibiting complex used herein or RNA constituting the complex (where RNA includes naturally-occurring RNAs and analogs) can be prepared into a composition for inhibiting an miRNA. The composition of the invention can specifically and effectively inhibit a target miRNA, so that the composition is useful in controlling the function of a gene via inhibition of an miRNA. The composition of the invention can be combined with a desirable pharmacologically acceptable carrier or medium as needed. Examples thereof include desired solutions that are generally used in suspension of a nucleic acid, such as distilled water, phosphate-buffered saline (PBS), sodium chloride solution, Ringer's solution, and culture solution. Vegetable oil, suspension, surfactant, stabilizer, biocide or the like may also be comprised. A preservative or another additive may also be added. The composition of the invention can also combine an organic matter such as a biopolymer, inorganic matter such as hydroxyapatite, specifically, a collagen matrix, polylactic acid polymer or copolymer, polyethylene glycol polymer or copolymer, a chemical derivative thereof or the like as a carrier. The composition of the invention can be used as a desired reagent or a pharmaceutical composition. The present invention also provides use of the composition of the invention, miRNA inhibiting complex used herein, or RNA constituting the complex or an analog thereof for inhibiting an miRNA. The present invention also provides an miRNA inhibitor comprising any one of the above.

In still another aspect, the present invention provides a method of treating a disease or a disorder, comprising administering an effective amount of the complex of the invention or a medicament comprising the same to a subject in need thereof. The present invention can be applied in, for example, but not limited to, use as a therapeutic agent for HCV or renal fibrosis, whose clinical development is already in progress.

The medicament of the invention may be administered on its own or as a suitable pharmaceutical composition. A pharmaceutical composition used in administration may comprise the medicament of the invention and a pharmaceutically acceptable carrier, diluent, or excipient. Such a pharmaceutical composition is provided as a dosage form that is suitable for oral or parenteral administration.

A composition for parenteral administration may be used as, for example, an injection, suppository, or the like, and injections may encompass dosage forms such as intravenous injection, subcutaneous injection, intradermal injection, intramuscular injection, and intravenous drip injection. Such injections can be prepared in accordance with known methods. Examples of preparation methods of an injection include preparation by dissolving, suspending, or emulsifying the nucleic acid of the invention in an aseptic aqueous solution or oily solution that is generally used in injections. Examples of aqueous solutions for injection that are used include saline, isotonic solution comprising glucose or other adjuvants and the like, which may be concomitantly used with a suitable solubilizer, such as alcohol (e.g., ethanol), polyalcohol (e.g., propylene glycol or polyethylene glycol), anionic surfactant (e.g., polysorbate 80, HCO-50 (polyoxyethylene (50 mol) adduct of hydrogenated castor oil)] or the like. For example, sesame oil, soybean oil or the like is used as an oily solution, which may be used concomitantly with benzyl benzoate, benzyl alcohol, or the like as a solubilizing agent. A prepared injection is preferably filled in a suitable ampule. Suppositories used in rectal administration may be prepared by mixing the aforementioned nucleic acid with a common base agent for suppositories.

Examples of compositions for oral administration include solid or liquid dosage forms, specifically tablets (including sugar-coated tablets and film-coated tablets), pills, granules, powder, capsules (including soft capsules), syrup, emulsion, suspension, and the like. Such a composition is manufactured by a known method and may contain a carrier, diluent, or excipient that is commonly used in the field of drug development. Examples of carriers and excipients for tablets that are used include lactose, starch, sucrose, and magnesium stearate.

The aforementioned parenteral or oral pharmaceutical composition is suitably prepared in a dosage form in a dosing unit that would match the dosage of an active ingredient. Examples of such a dosage form of a dosing unit include tablets, pills, capsules, injections (ampule) and suppositories.

The medicament of the invention has low toxicity, which can be administered orally or parenterally (e.g., intravascular administration, subcutaneous administration, or the like) to humans or mammals (e.g., rats, rabbits, sheep, pigs, cows, cats, dogs, monkeys, or the like) directly as a liquid agent or as a pharmaceutical composition in a suitable dosage form.

The medicament can be introduced into cells in vitro, ex vivo, or in vivo. When administered via cells, the medicament is introduced to the cells collected from suitable cultured cells or animal subjected to inoculation. Examples of introduction of nucleic acids include calcium phosphate coprecipitation, lipofection, DEAE dextran method, a method of direct injection of DNA solution into the tissue by an injection needle or the like, introduction by a gene gun, and the like. The dosage varies depending on the disease, patient weight, age, sex, symptom, objective of administration, form of administered composition, administration method, introduced gene, or the like. The dosage may be appropriately adjusted in accordance with the animal subjected to administration, administered site, number of administrations, or the like. Those skilled in the art can appropriately determine the dosage. The route of administration can be appropriately selected. The subject of administration is preferably a mammal (including humans and non-human mammals). Specifically, the subject includes humans, non-human primates such as monkeys, rodents such as mice and rats, rabbits, goats, sheep, pigs, cows, dogs, cats, and other mammals.

(DDS)

One aspect of the invention provides a composition comprising the miRNA inhibiting complex used herein or an RNA constituting the complex in combination with a carrier for nucleic acid delivery. A carrier for nucleic acid delivery is also called a drug delivery system (DDS) for nucleic acid delivery. Use of a suitable carrier promotes serum stability of an miRNA inhibiting complex or delivery to a target tissue, and is especially useful for therapeutic or prophylactic use.

One embodiment provides a composition comprising an miRNA inhibiting complex comprising an RNA or an analog thereof and a carrier for nucleic acid delivery. Such a composition can be a pharmaceutical composition. Such a composition is suitable for delivering an miRNA inhibiting complex to a desired site and can be used for such an application.

Examples of suitable carriers include lipid nanoparticles (LNP), cationic liposome, noncationic liposomes, cationic polymers, noncationic polymers, β-glucan, atelocollagens, PLGA nanoparticles, surfactant peptides, super apatites, and the like.

Lipid nanoparticles (LNP) are generally comprised of an ionized aminolipid, helper lipid, or PEGylated lipid, and can be formed by mixing an ethanol solution comprising a lipid and an acidic buffer comprising a nucleic acid molecule. The lipid core inside lipid nanoparticles can be filled with a nucleic acid molecule such as siRNA.

A liposome has a lipid bilayer and retains an aqueous phase inside. A nucleic acid molecule such as siRNA can be filled in an internal aqueous phase. A cationic liposome is preferred for stabilization of a nucleic acid molecule because a cationic liposome electrostatically interacts with a negative charge of a phosphoric acid group of the nucleic acid molecule. Meanwhile, non-cationic liposomes can be advantageous in that non-specific adsorption can be prevented in pharmacokinetics.

A cationic polymer is, for example, polymer or copolymer of acrylate, methacrylate, acrylamide, or the like having a quaternary ammonium base, polymer or copolymer of diallyldimethylammonium chloride, poly(vinylbenzyltrimethylammonium chloride), polyamide polyamine/epichlorohydrin condensate, condensate of amine and epichlorohydrin, polyallylamine hydrochloride, polyethyleneimine, polyamidine, cationized starch or cellulose, or the like. A biocompatible cationic polymer can be used to form nanoparticles or vesicles for use in delivery of a nucleic acid molecule.

The triple helix structure of β-glucan can be used as a carrier for delivery of a nucleic acid molecule. When the triple helix of β-1,3-glucan is dissolved in a polar organic solvent such as DMSO, the helix dissolves to be a single strand in a random coil form. When the solvent is returned to water, the triple helix structure is renatured. If there is a nucleic acid in the process of such "Renature", a polymer chain of the triple helix is replaced with a nucleic acid. The complexed nucleic acid is protected from hydrolysis due to an enzyme or nonspecific adsorption with a protein in the serum (M. Mizu, K. Koumoto, T. Kimura, K. Sakurai, and S. Shinkai, Biomaterials, 25, 3109 (2004)).

An atelocollagen is prepared by removing the primary antigen site of collagen, telopeptide, to lower the antigenicity of the collagen. An atelocollagen can form a complex with a nucleic acid molecule such as a siRNA to be stabilized (Drug Delivery System 25-6, 2010 607-614).

PLGA (polylactic acid) can prepare matrix type microparticles (nanospheres) by various methods and can be used by encapsulating a water-soluble drug such as a nucleic acid.

A surfactant peptide is a self-assembled peptide comprised of about 6 to 10 residues of amino acids, forming nanomicelles or nanotubes with a particle diameter of about 50 to 100 nm in an aqueous solution. Since surfactant-like peptides can control the surface charge or particle size of a substance sequence dependently, such peptides are being developed as a gene delivery carrier for an siRNA or the like.

A super apatite (Wu X, Yamamoto H, Nakanishi H, Yamamoto Y, Inoue A, Tei M, et al. (2015) Innovative Delivery of siRNA to Solid Tumors by Super Carbonate Apatite. PLoS ONE 10(3): e0116022. doi:10.1371/journal.pone.0116022) is also being studied as a preferred carrier for delivery of a nucleic acid such as siRNA. Ultrafine particles prepared by finely grinding "carbonate apatite", a compound for transduction, to a diameter of about 10 nm with ultrasound waves are called "super apatite". It is reported that a super apatite bound to an agent, when intravenously injected into a cancer bearing mouse, exhibited a higher anticancer effect compared to conventional microparticles. It is understood that microparticles are incorporated only into cancer cells through a gap in the blood vessel wall because blood vessels in a cancer tissue are brittle. It is understood that microparticles such as super apatite have few side effects because the microparticles are decomposed in cancer cells.

Examples of other carriers include dendrimers (e.g., dendritic polylysine (KG6), which is a dendrimer having lysine as a constituent unit) and PEG-P [Asp(DET)], which is a cationic polyamino acid derivative.

In one preferred embodiment of the invention, a carrier is LNP, and the LNP preferably comprises a cationic lipid. For example, LNP can comprise a cationic lipid, a helper lipid, and/or a PEGylated lipid.

Examples of particularly preferred carriers in nucleic acid delivery of the invention include those using a lipid membrane complex comprising a cationic lipid described below.

In a preferred embodiment, a cationic lipid used in a carrier comprises a tertiary amine and/or disulfide bond in a molecule. By employing such a structure, after the disulfide bond is cleaved, a structure having two lipid sites is destructed and a lipid membrane structure is destroyed in the cell to efficiently release the enclosed compound such as a nucleic acid into the cytoplasm. When used for introducing a nucleic acid, the nucleic acid is released in the cell without interacting with an amine site, so that access to or bond with the nucleic acid of a transcription factor is not obstructed. When a disulfide bond is cleaved in a cell, generated residues are not separated into polar group, i.e., amine site, and a non-polar group, i.e., lipid site, so that the residues retain the surfactant capability. This is expected to have an effect of destabilizing an endosome membrane and promoting endosomal escape associated therewith.

Examples of preferred cationic lipids include a composition represented by formula (1')

[Chemical Formula 26]

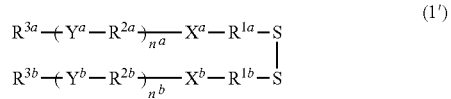

(1')

wherein $X^a$ and $X^b$ are independently a substituent comprising a tertiary amine, s is 1 or 2, $R^4$ represents an alkyl group with 1 to 6 carbons, $n^a$ and $n^b$ are independently 0 or 1, $R^{1a}$ and $R^{1b}$ independently represent an alkylene group with 1 to 6 carbons, $R^{2a}$ and $R^{2b}$ independently represent an alkylene group with 1 to 6 carbons, $Y^a$ and $Y^b$ independently represent an ester bond, an amide bond, a carbamate bond, an ether bond, or a urea bond, $R^{3a}$ and $R^{3b}$ independently represent a sterol residue, a lipophilic vitamin derivative residue, or an aliphatic hydrocarbon group with 12 to 22 carbons, a sterol residue is a cholesteryl group, a cholestaryl group, stigmasteryl group, a p-sitosteryl group, a lanosteryl group, or an ergosteryl group, and a lipophilic vitamin is retinoic acid, retinol, retinal, ergosterol, 7-dehydrocholesterol, calciferol, cholecalciferol, dihydroergocalciferol, dihydrotachysterol, tocopherol, or tocotrienol In formula (1'), $X^a$ and $X^b$ are preferably independently $X^1$, $X^2$, or $X^3$:

[Chemical Formula 27]

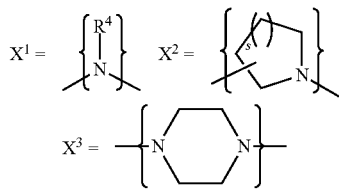

Preferably, $R^{3a}$ and $R^{3b}$ in formula (1') are independently a lipophilic vitamin derivative residue. Preferably, $Y^a$ and $Y^b$ in formula (1') are independently an ester bond. Preferably, $n^a$ and $n^b$ in formula (1') are 1.

Preferably, $R^{3a}$ and $R^{3b}$, $Y^a$ and $Y^b$, and $X^a$ and $X^b$ in formula (1') are identical.

Examples of preferred cationic lipids include compounds represented by formula (1)

[Chemical Formula 28]

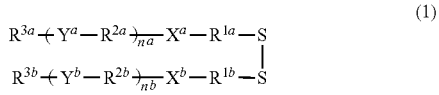

$X^a$ and $X^b$ in formula (1) are independently $X^1$, $X^2$, or $X^3$

[Chemical Formula 29]

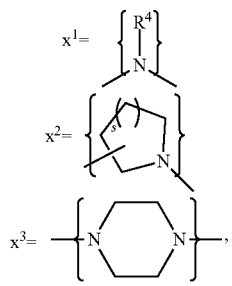

$X^a$ and $X^b$ in formula (1) are independently $X^1$ or $X^2$:

[Chemical Formula 30]

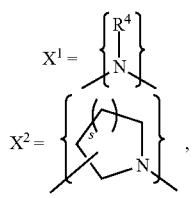

$R^4$ in $X^1$ represents an alkyl group with 1 to 6 carbons, which can be straight, branched, or cyclic. The number of carbons of the alkyl group is preferably 1 to 3. Specific examples of alkyl group with 1 to 6 carbons include a methyl group, ethyl group, propyl group, isopropyl group, n-butyl group, sec-butyl group, isobutyl group, tert-butyl group, pentyl group, isopentyl group, neopentyl group, t-pentyl group, 1,2-dimethylpropyl group, 2-methylbutyl group, 2-methylpentyl group, 3-methylpentyl group, 2,2-dimethylbutyl group, 2,3-dimethylbutyl group, cyclohexyl group, and the like. $R^4$ is preferably a methyl group, ethyl group, propyl group, or isopropyl group, and most preferably a methyl group.

s in $X^2$ is 1 or 2. If s is 1, $X^2$ is preferably a pyrrolidinium group. If s is 2, $x^2$ is preferably a piperidinium group.

$X^a$ and $X^b$ can be the same or different, but $X^a$ and $X^b$ are preferably the same group.

$n^a$ and $n^b$ are independently an integer from 0 to 2. If $n^a$ is 1, $R^{3a}$ binds to $X^a$ via $Y^a$ and $R^{2a}$, and if $n^a$ is 0, the structure of $R^{3a}$—$X^a$—$R^{1a}$—S— is exhibited. Likewise, if $n^b$ is 1, $R^{3b}$ binds to $X^b$ via $Y^b$ and $R^{2b}$, and if $n^b$ is 0, the structure of $R^{3b}$—$X^b$—$R^{1b}$—S— is exhibited.

$n^a$ and $n^b$ can be the same or different, but $n^a$ and $n^b$ are preferably the same.

$R^{1a}$ and $R^{1b}$ independently represent an alkylene group with 1 to 6 carbon, which can be straight or branched, but is preferably straight. Specific examples of alkylene group with 1 to 6 carbons include a methylene group, ethylene group, trimethylene group, isopropylene group, tetramethylene group, isobutylene group, pentamethylene group, neopentylene group, and the like. $R^{1a}$ and $R^{1b}$ are preferably a methylene group, ethylene group, trimethylene group, isopropylene group, or tetramethylene group, but is most preferably an ethylene group.

$R^{1a}$ and $R^{1b}$ can be the same or different, but $R^{1a}$ and $R^{1b}$ are preferably the same.

$R^{2a}$ and $R^{2b}$ independently represent an alkylene group with 1 to 6 carbons, which can be straight or branched, but is preferably straight. Examples of alkylene groups with 1 to 6 carbons include those listed as examples of alkylene groups with 1 to 6 carbons of $R^{1a}$ and $R^{1b}$. $R^{2a}$ and $R^{2b}$ are preferably a methylene group, ethylene group, trimethylene group, isopropylene group, or tetramethylene group and are most preferably a trimethylene group.

$R^{2a}$ and $R^{2b}$ can be the same or different, but $R^{2a}$ and $R^{2b}$ are preferably the same group.

$Y^a$ and $Y^b$ are independently an ester bond, an amide bond, a carbamate bond, an ether bond, or a urea bond, preferably an ester bond, amide bond, or carbamate bond, and most preferably an ester bond. While the orientation of the $Y^a$ and $Y^b$ bond is not limited, if $Y^a$ is an ester bond, the structure of $R^{3a}$—CO—O—$R^{2a}$— is preferably exhibited, and if $Y^b$ is an ester bond, the structure of $R^{3b}$—CO—O—$R^{2b}$— is preferably exhibited.

$Y^a$ and $Y^b$ can be the same or different, but $Y^a$ and $Y^b$ are preferably the same group.

$R^{3a}$ and $R^{3b}$ independently represent a sterol residue, a lipophilic vitamin derivative residue, or an aliphatic hydrocarbon group with 12 to 22 carbons, preferably a lipophilic vitamin derivative residue or an aliphatic hydrocarbon group with 12 to 22 carbons, and most preferably a lipophilic vitamin derivative residue.

Examples of sterol residues include a cholesteryl group (cholesterol residue), a cholestaryl group (cholestanol residue), stigmasteryl group (stigmasterol residue), a β-sitosteryl group (β-sitosterol residue), a lanosteryl group (lanosterol residue), an ergosteryl group (ergosterol residue), and the like. A sterol residue is preferably a cholesteryl group or cholestaryl group.

A lipophilic vitamin derivative residue is a residue derived from a lipophilic vitamin as well as residue derived from a derivative produced by reacting a hydroxyl group, aldehyde group, or carboxyl group, which is a functional group in a lipophilic vitamin, with a carboxyl group, amino group, or hydroxyl group of another difunctional compound to appropriately convert the functional group to another reactive functional group. For example, lipophilic vitamin having a hydroxyl group can be reacted with a dicarboxylic acid of succinic acid anhydride, glutaric acid anhydride, or the like to convert a hydroxyl group to a carboxylic acid. Examples of lipophilic vitamin include retinoic acid, retinol, retinal, ergosterol, 7-dihydrocholesterol, calciferol, cholecalciferol, dihydroergocalciferol, dihydrotachysterol, tocopherol, tocotrienol, and the like. Lipophilic vitamin is preferably a retinoic acid or tocopherol. Examples of difunctional compound include, but are not limited to, multivalent carboxylic acid, dicarboxylic acid, amino acid, hydroxy acid, amino alcohol, multivalent alcohol, divalent alcohol, and the like.

An aliphatic hydrocarbon group with 12 to 22 carbons can be straight or branched, but is preferably straight. The aliphatic hydrocarbon group can be saturated or unsaturated. For an unsaturated aliphatic hydrocarbon group, the number of unsaturated bonds contained in the aliphatic hydrocarbon group is generally 1 to 6, preferably 1 to 3, and more preferably 1 to 2. Unsaturated bonds include carbon-carbon double bonds and carbon-carbon triple bonds, but are preferably carbon-carbon double bonds. The number of carbons contained in the aliphatic hydrocarbon group is preferably 12 to 18 and most preferably 13 to 17. Aliphatic hydrocarbon groups include alkyl groups, alkenyl groups, alkynyl groups, and the like, but are preferably an alkyl group or an alkenyl group. Specific examples of aliphatic hydrocarbon groups with 12 to 22 carbons include dodecyl group, tridecyl group, tetradecyl group, pentadecyl group, hexadecyl group, heptadecyl group, octadecyl group, nonadecyl group, icosyl group, henicosyl group, docosyl group, dodecenyl group, tridecenyl group, tetradecenyl group, pentadecenyl group, hexadecenyl group, heptadecenyl group, octadecenyl group, nonadecenyl group, icocenyl group, henicocenyl group, dococenyl group, decadienyl group, tridecadienyl group, tetradecadienyl group, pentadecadienyl group, hexadecadienyl group, heptadecadienyl group, octadecadienyl group, nonadecadienyl group, icosadienyl group, henicosadienyl group, docosadienyl group, octadecatrienyl group, icosatrienyl group, icosatetraenyl group, icosapentaenyl group, docosahexaenyl group, isostearyl group, and the like. An aliphatic hydrocarbon group with 12 to 22 carbons is preferably a tridecyl group, tetradecyl group, heptadecyl group, octadecyl group, heptadecadienyl group, or octadecadienyl group, and especially preferably a tridecyl group, heptadecyl group, or heptadecadienyl group.

In one embodiment, an aliphatic hydrocarbon group with 12 to 22 carbons derived from fatty acid, aliphatic alcohol, or aliphatic amine is used. If $R^{3a}$ (or $R^{3b}$) is derived from a fatty acid, $Y^a$ (or $Y^b$) is an ester bond or amide bond, and $Y^a$ (or $Y^b$) comprises fatty acid derived carbonyl carbon. If for example linoleic acid is used, $R^{3a}$ (or $R^{3b}$) is a heptadecadienyl group.

$R^{3a}$ and $R^{3b}$ can be the same or different, but $R^{3a}$ and $R^{3b}$ are preferably the same group.

In one embodiment, $X^a$ and $X^b$ are the same, $n^a$ and $n^b$ are same, $R^{1a}$ and $R^{1b}$ are the same, $R^{2a}$ and $R^{2b}$ are the same, $R^{3a}$ and $R^{3b}$ are the same, and $Y^a$ and $Y^b$ are the same.

In one embodiment,
$X^a$ and $X^b$ are independently $X^1$,
$R^4$ represents an alkyl group with 1 to 3 carbons and $n^a$ and $n^b$ are 1,
$R^{a1}$ and $R^{1b}$ independently represent an alkylene group with 1 to 6 carbons,
$R^{2a}$ and $R^{2b}$ independently represent an alkylene group with 1 to 6 carbons,
$Y^a$ and $Y^b$ independently represent an ester bond, and
$R^{3a}$ and $R^{3b}$ independently represent an aliphatic hydrocarbon group with 12 to 22 carbons.

In one embodiment,
$X^a$ and $X^b$ are $X^1$,
$R^4$ represents an alkyl group with 1 to 3 carbons and $n^a$ and $n^b$ are 1,
$R^{1a}$ and $R^{1b}$ represent an alkylene group with 1 to 6 carbons,
$R^{2a}$ and $R^{2b}$ represent an alkylene group with 1 to 6 carbons,
$Y^a$ and $Y^b$ represent an ester bond,
$R^{3a}$ and $R^{3b}$ represent an aliphatic hydrocarbon group with 12 to 22 carbons,
$X^a$ and $X^b$ are the same,
$R^{1a}$ and $R^{1b}$ are the same,
$R^{2a}$ and $R^{2b}$ are the same, and
$R^{3a}$ and $R^{3b}$ are the same.

In one embodiment,
$X^a$ and $X^b$ are $X^1$,
$R^4$ represents a methyl group and $n^a$ and $n^b$ are 1,
$R^{1a}$ and $R^{1b}$ represent an ethylene group,
$R^{2a}$ and $R^{2b}$ represent a trimethylene group,
$Y^a$ and $Y^b$ represent —CO—O—, and
$R^{3a}$ and $R^{3b}$ independently represent an alkyl group or alkenyl group with 13 to 17 carbons.

In one embodiment,
$X^a$ and $X^b$ are $X^1$,
$R^4$ represents a methyl group and $n^a$ and $n^b$ are 1,
$R^{1a}$ and $R^{1b}$ represent an ethylene group,
$R^{2a}$ and $R^{2b}$ represent a trimethylene group,
$Y^a$ and $Y^b$ represent —CO—O—, and
$R^{3a}$ and $R^{3b}$ represent an alkyl group or alkenyl group with 13 to 17 carbons, and
$R^{3a}$ and $R^{3b}$ are the same.

In one embodiment,
$X^a$ and $X^b$ are independently $X^1$,
$R^4$ represents an alkyl group with 1 to 3 carbons and $n^a$ and $n^b$ are 1,
$R^{1a}$ and $R^{1b}$ independently represent an alkylene group with 1 to 6 carbons,
$R^{2a}$ and $R^{2b}$ independently represent an alkylene group with 1 to 6 carbons,
$Y^a$ and $Y^b$ represent an ester bond, and
$R^{3a}$ and $R^{3b}$ independently represent a lipophilic vitamin derivative residue (e.g., retinoic acid residue or tocopherol residue).

In one embodiment,
$X^a$ and $X^b$ are $X^1$,
$R^4$ represents an alkyl group with 1 to 3 carbons and $n^a$ and $n^b$ are 1,
$R^{10}$ and $R^{1b}$ represent an alkylene group with 1 to 6 carbons,
$R^{2a}$ and $R^{2b}$ represent an alkylene group with 1 to 6 carbons,
$Y^a$ and $Y^b$ represent an ester bond,
$R^{3a}$ and $R^{3b}$ represent a lipophilic vitamin derivative residue (e.g., retinoic acid residue or tocopherol residue),
$X^a$ and $X^b$ are the same,
$R^{1a}$ and $R^{1b}$ are the same,
$R^{2a}$ and $R^{2b}$ are the same, and
$R^{3a}$ and $R^{3b}$ are the same.

In one embodiment,
$X^a$ and $X^b$ are $X^1$,
$R^4$ represents a methyl group and $n^a$ and $n^b$ are 1,
$R^{1a}$ and $R^{1b}$ represent an ethylene group,
$R^{2a}$ and $R^{2b}$ represent a trimethylene group,
$Y^a$ and $Y^b$ represent —CO—O—, and $R^{3a}$ and $R^{3b}$ independently represent a lipophilic vitamin derivative residue (e.g., retinoic acid residue or tocopherol residue).

In one embodiment,
$X^a$ and $X^b$ are X1,
$R^4$ represents a methyl group and $n^a$ and $n^b$ are 1,
$R^{1a}$ and $R^{1b}$ represent an ethylene group,
$R^{2a}$ and $R^{2b}$ represent a trimethylene group,
$Y^a$ and $Y^b$ represent —CO—O—,
$R^{3a}$ and $R^{3b}$ represent a lipophilic vitamin derivative residue (e.g., retinoic acid residue or tocopherol residue), and $R^{3a}$ and $R^{3b}$ are the same.

In one embodiment,
$X^a$ and $X^b$ are $X^2$,
S is 2,
$n^a$ and $n^b$ are 1,
$R^{1a}$ and $R^{1b}$ represent an ethylene group,
$R^{2a}$ and $R^{2b}$ represent an ethylene group,
$Y^a$ and $Y^b$ represent —CO—O—,
$R^{3a}$ and $R^{3b}$ represent a lipophilic vitamin derivative residue from a reaction between tocopherol and succinic acid, and $R^{3a}$ and $R^{3b}$ are the same.

Specific examples of cationic lipids of the invention include the following compounds of B-2, B-2-2, B-2-3, B-2-4, and B-2-5.

TABLE 1

| Name of compound | Structure |
|---|---|
| B-2 | 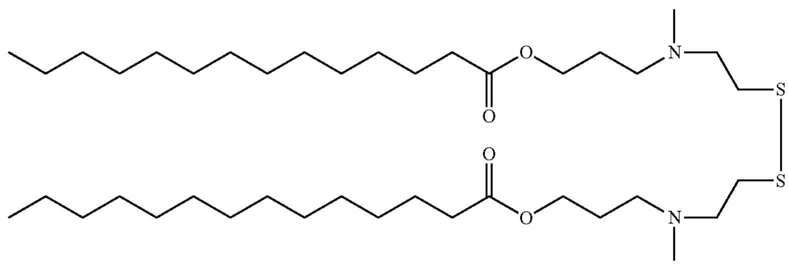 [SMILES: CCCCCCCCCCCCCC(=O)OCCCN(C)CCSSCCN(C)CCCOC(=O)CCCCCCCCCCCCC] |
| B-2-2 | 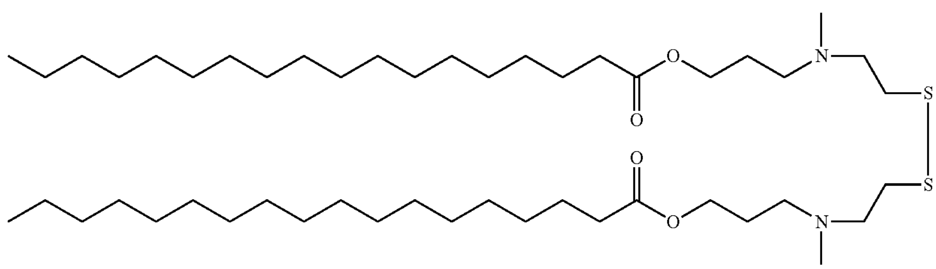 [SMILES: CCCCCCCCCCCCCCCCCC(=O)OCCCN(C)CCSSCCN(C)CCCOC(=O)CCCCCCCCCCCCCCCCC] |
| B-2-3 | 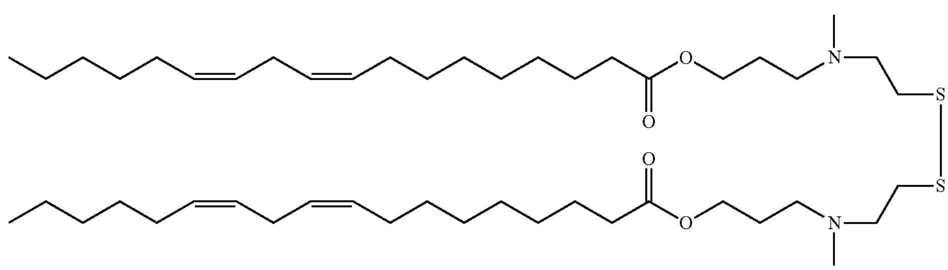 [SMILES: CCCCC/C=C\C/C=C\CCCCCCCC(=O)OCCCN(C)CCSSCCN(C)CCCOC(=O)CCCCCCC/C=C\C/C=C\CCCCC] |
| B-2-4 | 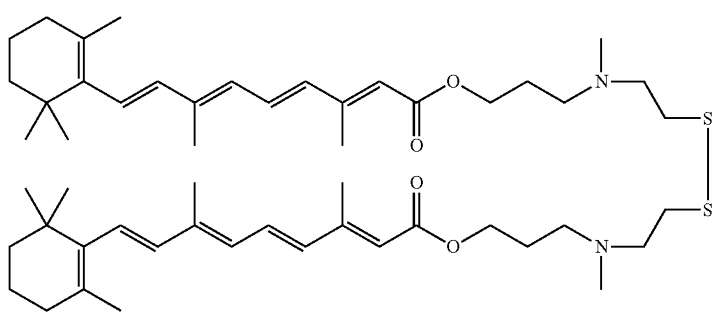 [SMILES: CC1=C(/C=C/C(C)=C/C=C/C(C)=C/C(=O)OCCCN(C)CCSSCCN(C)CCCOC(=O)/C=C(C)/C=C/C=C(C)/C=C/C2=C(C)CCCC2(C)C)C(C)(C)CCC1] |

TABLE 1-continued

| Name of compound | Structure |
|---|---|
| B-2-5 | 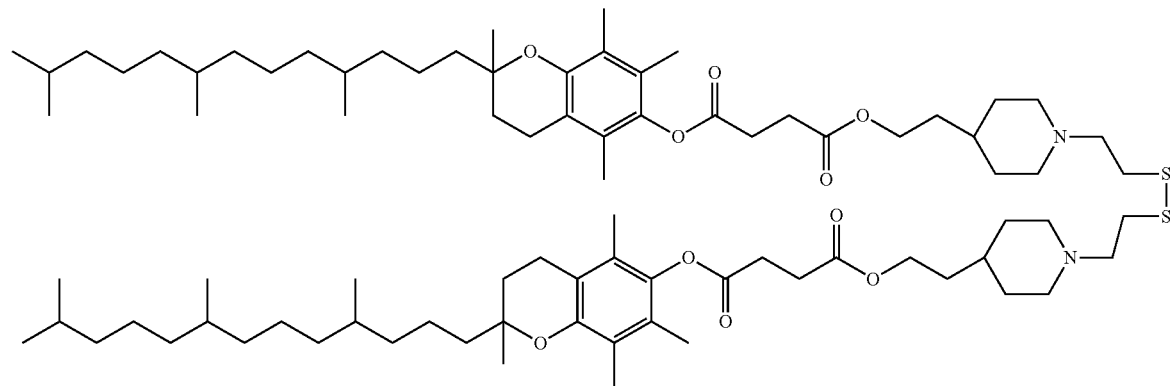 |

Examples of particularly preferred cationic lipids include

[Chemical Formula 31]

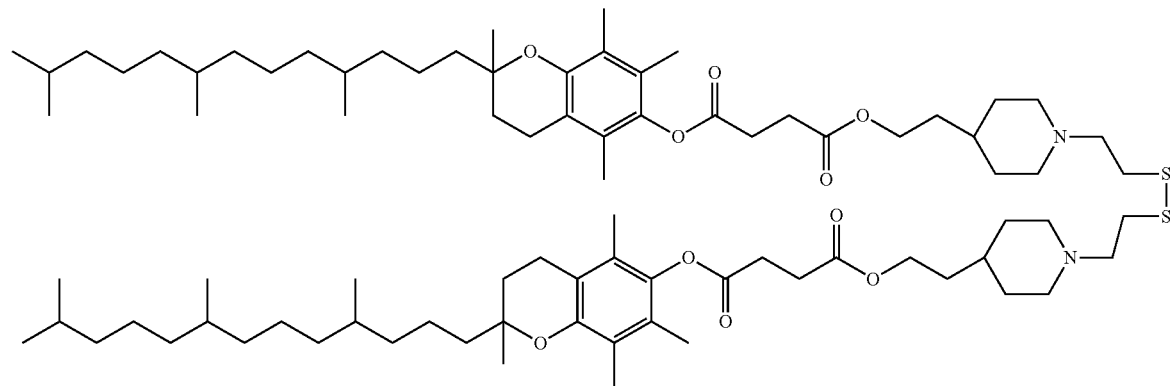

Said cationic lipid is commercially available as COATSOME SS-33/4PE-15® (NOF Corporation).

Examples of preferred cationic lipids include compounds represented by formula (4):

[Chemical Formula 32]

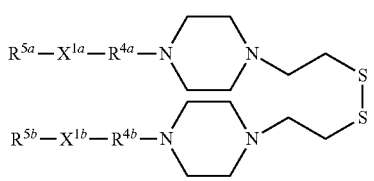 (4)

$R^{4a}$ and $R^{4b}$ independently represent an alkylene group or an oxydialkylene group with 8 carbons or less, preferably an alkylene group with 8 carbons or less.

An alkylene group with 8 carbons or less can be straight or branched, but is preferably straight. The number of carbons comprised in the alkylene group is preferably 6 or less, and most preferably 4 or less. Specific examples of alkylene groups with 8 carbons or less include a methylene group, ethylene group, propylene group, isopropylene group, tetramethylene group, isobutylene group, pentamethylene group, hexamethylene group, heptamethylene group, octamethylene group, and the like. An alkylene group with 8 carbons or less is preferably a methylene group, ethylene group, propylene group, or tetramethylene group, and most preferably an ethylene group.

An oxydialkylene group with 8 carbons or less indicates an alkylene group mediated by an ether group (alkylene-O-alkylene), and the total number of carbons of the two alkylene groups is 8 or less. In this regard, the two alkylenes can be the same or different, but are preferably the same. Specific examples of oxydialkylene groups with 8 carbons or less include an oxydimethylene group, oxydiethylene group, oxydipropylene group, oxydibutylene group, and the like. An oxydialkylene group with 8 carbons or less is preferably an oxydimethylene group, oxydiethylene group, or oxydipropylene group, and is most preferably an oxydiethylene group.

$R^{4a}$ and $R^{4b}$ can be the same or different, but $R^{4a}$ and $R^{4b}$ are preferably the same group.

$X^{1a}$ and $X^{1b}$ are independently an ester bond, amide bond, carbamate bond, or ether bond, preferably an ester bond or amide bond, and most preferably an ester bond. While the direction of the $X^{1a}$ and $X^{1b}$ bond is not limited, if $X^{1a}$ and $X^{1b}$ are ester bonds, they preferably exhibit the structures $R^{5a}$—CO—O—$R^{4a}$— and $R^{5b}$—CO—O—$R^{4b}$—.

$X^{1a}$ and $X^{1b}$ can be the same or different, but $X^{1a}$ and $X^{1b}$ are preferably the same group.

$R^{5a}$ and $R^{5b}$ independently represent a sterol residue, a lipophilic vitamin derivative residue, or an aliphatic hydrocarbon group with 13 to 23 carbons, and are preferably a lipophilic vitamin derivative residue or an aliphatic hydrocarbon group with 13 to 23 carbons and most preferably an aliphatic hydrocarbon group. $R^{5a}$ and $R^{5b}$ are also preferably a lipophilic vitamin derivative residue from the viewpoint of organ (especially liver) specificity.

Examples of "sterol residue" include sterol without a reactive functional group (e.g., hydroxyl group) involved in a bond with $X^a$ or $X^b$, and sterol derivative derived residues, but a sterol residue is preferably a sterol derivative derived residue. Examples of sterol derivatives include sterol hemiesters prepared from reacting a hydroxyl group of sterol with one of the carboxylic acid of dicarboxylic acid (in such a case, the other carboxylic acid would be a reactive functional group). Examples of sterol include cholesterol, cholestanol, stigmasterol, R-sitosterol, lanosterol, ergosterol, and the like. Preferably, sterol is cholesterol or cholestanol. Examples of dicarboxylic acid include malonic acid, succinic acid, glutaric acid, adipic acid, and the like. Dicarboxylic acid is preferably succinic acid or glutaric acid. Specific examples of sterol derivatives include cholesterol hemisuccinate ester, cholesterol hemiglutarate ester, and the like.

Examples of "lipophilic vitamin residue" include lipophilic vitamin without a reactive functional group (e.g., hydroxyl group) involved in a bond with $X^{1a}$ or $X^{1b}$, and lipophilic vitamin derivative derived residues, but a lipophilic vitamin residue is preferably a lipophilic vitamin derivative derived residue. Examples of lipophilic vitamin derivatives include lipophilic vitamin hemiesters prepared from reacting a hydroxyl group of lipophilic vitamin, whose reactive functional group is a hydroxyl group, with one of the carboxylic acid of dicarboxylic acid (in such a case, the other carboxylic acid would be a reactive functional group). Examples of lipophilic vitamin include retinoic acid, retinol, retinal, ergosterol, 7-dihydrocholesterol, calciferol, cholecalciferol, dihydroergocalciferol, dihydrotachysterol, tocopherol, tocotrienol, and the like. Lipophilic vitamin is preferably retinoic acid or tocopherol, and most preferably tocopherol. Examples of dicarboxylic acid include malonic acid, succinic acid, glutaric acid, adipic acid, and the like. Dicarboxylic acid is preferably succinic acid or glutaric acid. Specific examples of lipophilic vitamin derivatives include tocopherol hemisuccinate ester, tocopherol hemiglutarate ester, and the like.

An aliphatic hydrocarbon group with 13 to 23 carbons can be straight or branched, but is preferably straight. The aliphatic hydrocarbon group can be saturated or unsaturated. For an unsaturated aliphatic hydrocarbon group, the number of unsaturated bonds contained in the aliphatic hydrocarbon group is generally 1 to 6, preferably 1 to 3, and most preferably 1 to 2. Unsaturated bonds include carbon-carbon double bonds and carbon-carbon triple bonds, but are preferably carbon-carbon double bonds. The number of carbons contained in the aliphatic hydrocarbon group, when straight, is preferably 13 to 21 and most preferably 13 to 17. Examples of aliphatic hydrocarbon groups with 13 to 23 carbons include tridecyl group, tetradecyl group, pentadecyl group, hexadecyl group, heptadecyl group, octadecyl group, nonadecyl group, icosyl group, henicosyl group, docosyl group, tricosyl group, tridecenyl group, tetradecenyl group, pentadecenyl group, hexadecenyl group, heptadecenyl group, octadecenyl group, nonadecenyl group, icocenyl group, henicocenyl group, dococenyl group, tricocenyl group, tridecadienyl group, tetradecadienyl group, pentadecadienyl group, hexadecadienyl group, heptadecadienyl group, octadecadienyl group, nonadecadienyl group, icosadienyl group, henicosadienyl group, docosadienyl group, octadecatrienyl group, icosatrienyl group, icosatetraenyl group, icosapentaenyl group, docosahexaenyl group, methyl dodecyl group, methyl tridecyl group, methyl tetradecyl group, methyl pentadecyl group, methyl heptadecyl group, methyl octadecyl group, methyl nonadecyl group, methyl icosyl group, methyl henicosyl group, methyl docosyl group, ethyl undecyl group, ethyl dodecyl group, ethyl tridecyl group, ethyl tetradecyl group, ethyl pentadecyl group, ethyl heptadecyl group, ethyl octadecyl group, ethyl nonadecyl group, ethyl icosyl group, ethyl henicosyl group, hexyl heptyl group, hexyl nonyl group, heptyl octyl group, heptyl decyl group, octyl nonyl group, octyl undecyl group, nonyl decyl group, decyl undecyl group, undecyl dodecyl group, hexamethyl undecyl group, and the like. A straight aliphatic hydrocarbon groups with 12 to 23 carbons is preferably a tridecyl group, pentadecyl group, heptadecyl group, nonadecyl group, henicosyl group, heptadecenyl group, or heptadecadienyl group, especially preferably a tridecyl group, heptadecyl group, heptadecenyl group, or heptadecadienyl group. A branched aliphatic hydrocarbon group with 12 to 23 carbons is preferably a methyl pentadecyl group, hexyl nonyl group, heptyl decyl group, octyl undecyl group, or hexamethyl undecyl group, and especially preferably a methyl pentadecyl group, hexyl nonyl group, or heptyl decyl group.

In one embodiment, an aliphatic hydrocarbon group with 13 to 23 carbons derived from fatty acid, aliphatic alcohol, or aliphatic amine is used. If $R^{5a}$ is derived from fatty acid, $X^{1a}$ is an ester bond or amide bond, and aliphatic carbonyl carbon is included in $X^{1a}$. If $R^{5b}$ is derived from fatty acid, $X^{1b}$ is an ester bond or amide bond, and aliphatic carbonyl carbon is included in $X^{1b}$. A specific example of an aliphatic hydrocarbon group would be a heptadecadienyl group when linoleic acid is used as fatty acid, and a heptadecenyl group when oleic acid is used as fatty acid.

$R^{5a}$ and $R^{5b}$ can be the same or different, but $R^{5a}$ and $R^{5b}$ are preferably the same group.

In one embodiment, $R^{4a}$ and $R^{4b}$ are the same, $X^{1a}$ and $X^{1b}$ are the same, and $R^{5a}$ and $R^{5b}$ are the same.

In one embodiment,
$R^{4a}$ and $R^{4b}$ independently represent an alkylene group with 8 carbons or less (1 to 8 carbons),
$X^{1a}$ and $X^{1b}$ represent an ester bond, and
$R^{5a}$ and $R^{5b}$ independently represent a lipophilic vitamin derivative residue (e.g., tocopherol hemisuccinate ester derived group).

In one embodiment,
$R^{4a}$ and $R^{4b}$ independently represent an alkylene group with 8 carbons or less (1 to 8 carbons),
$X^{1a}$ and $X^{1b}$ represent an ester bond, and
$R^{5a}$ and $R^{5b}$ independently represent an aliphatic hydrocarbon group with 13 to 23 carbons (e.g., heptadecadienyl group or heptadecenyl group).

In one embodiment,
$R^{4a}$ and $R^{4b}$ independently represent an alkylene group with 8 carbons or less (1 to 8 carbons),
$X^{1a}$ and $X^{1b}$ represent an ester bond,
$R^{5a}$ and $R^{5b}$ independently represent a lipophilic vitamin derivative residue (e.g., tocopherol hemisuccinate ester derived group),
$R^{4a}$ and $R^{4b}$ are the same, and
$R^{5a}$ and $R^{5b}$ are the same.

In one embodiment,
$R^{4a}$ and $R^{4b}$ represent an alkylene group with 8 carbons or less (1 to 8 carbons),
$X^{1a}$ and $X^{1b}$ represent an ester bond,
$R^{5a}$ and $R^{5b}$ represent an aliphatic hydrocarbon group with 13 to 23 carbons (e.g., heptadecadienyl group or heptadecenyl group),
$R^{4a}$ and $R^{4b}$ are the same, and
$R^{5a}$ and $R^{5b}$ are the same.

In one embodiment,
$R^{4a}$ and $R^{4b}$ independently represent an ethylene group,
$X^{1a}$ and $X^{1b}$ represent —CO—O—, and $R^{5a}$ and $R^{5b}$ independently represent a lipophilic vitamin derivative residue (e.g., tocopherol hemisuccinate ester derived group).

In one embodiment,
$R^{4a}$ and $R^{4b}$ represent an ethylene group,
$X^{1a}$ and $X^{1b}$ represent —CO—O—, and
$R^{5a}$ and $R^{5b}$ independently represent an aliphatic hydrocarbon group with 13 to 23 carbons (e.g., heptadecadienyl group or heptadecenyl group).

In one embodiment,
$R^{4a}$ and $R^{4b}$ represent an ethylene group,
$X^{1a}$ and $X^{1b}$ represent —CO—O—,
$R^{5a}$ and $R^{5b}$ represent a lipophilic vitamin residue (e.g., tocopherol hemisuccinate ester derived group), and
$R^{5a}$ and $R^{5b}$ are the same.

In one embodiment,
$R^{4a}$ and $R^{4b}$ represent an ethylene group,
$X^{1a}$ and $X^{1b}$ represent —CO—O—,
$R^{5a}$ and $R^{5b}$ independently represent an aliphatic hydrocarbon group with 13 to 23 carbons (e.g., heptadecadienyl group or heptadecenyl group), and
$R^{5a}$ and $R^{5b}$ are the same.

Specific examples of the cationic lipids of the invention include the following TS-PZ4C2, L-PZ4C2, and O-PZ4C2.

TABLE 2

| Name of cationic lipid | Structure |
|---|---|
| TS-PZ4C2 | 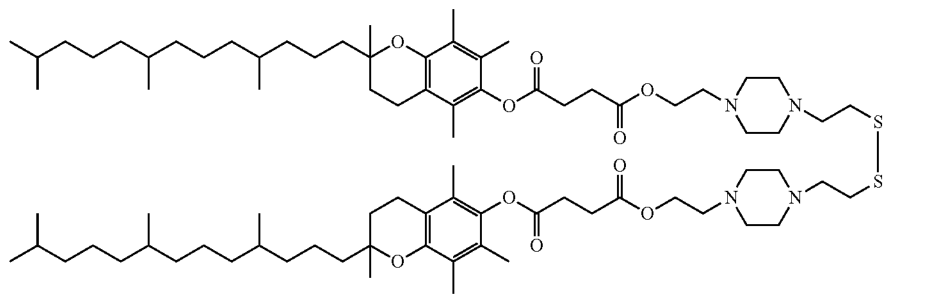 [SMILES: Cc1c(C)c2c(c(C)c1OC(=O)CCC(=O)OCCN1CCN(CCSSCCN3CCN(CCOC(=O)CCC(=O)Oc4c(C)c(C)c5c(c4C)CCC(C)(CCCC(C)CCCC(C)CCCC(C)C)O5)CC3)CC1)CCC(C)(CCCC(C)CCCC(C)CCCC(C)C)O2] |
| L-PZ4C2 | 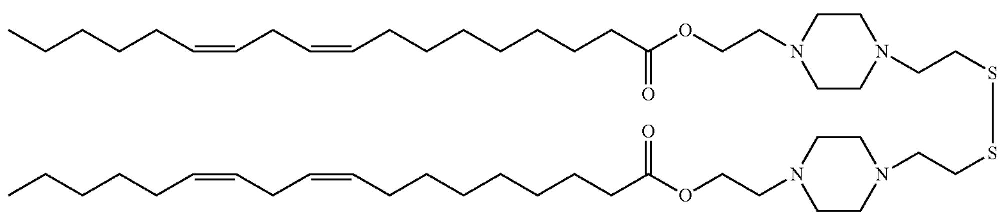 [SMILES: CCCCC/C=C\C/C=C\CCCCCCCC(=O)OCCN1CCN(CCSSCCN2CCN(CCOC(=O)CCCCCCC/C=C\C/C=C\CCCCC)CC2)CC1] |
| O-PZ4C2 | 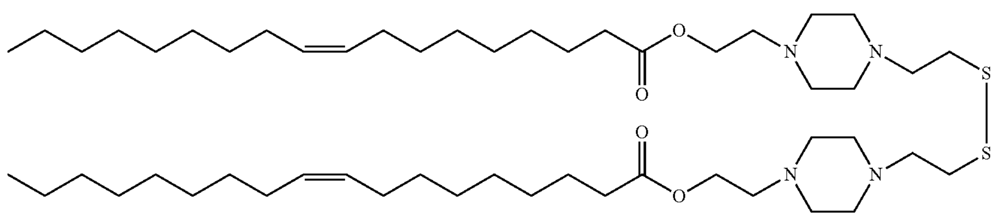 [SMILES: CCCCCCCC/C=C\CCCCCCCC(=O)OCCN1CCN(CCSSCCN2CCN(CCOC(=O)CCCCCCC/C=C\CCCCCCCC)CC2)CC1] |

Examples of particularly preferred cationic lipids include

[Chemical Formula 33]

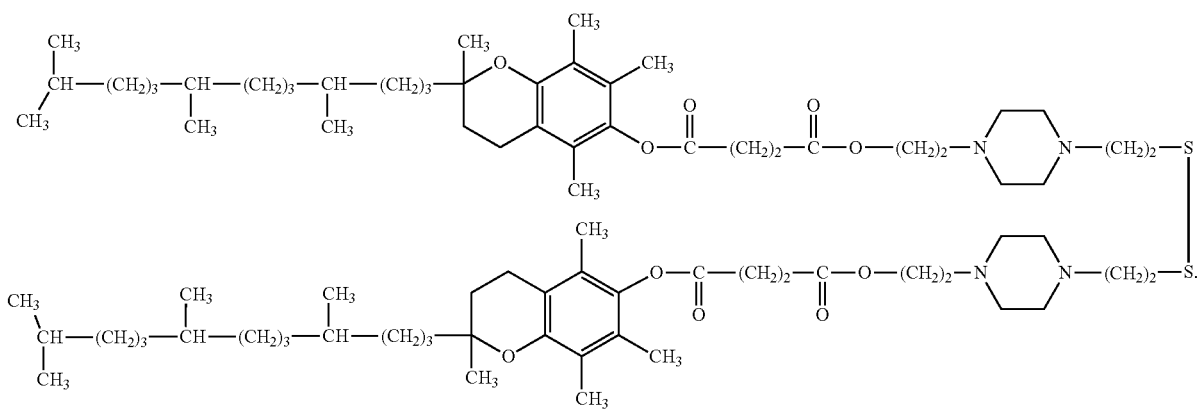

Said cationic lipid is commercially available as COATSOME SS-33/1PZ-21® (NOF Corporation).

A lipid membrane structure comprising said compound as a constituent lipid of a membrane can be used as a carrier. One embodiment of the invention provides a composition comprising a lipid membrane structure and a nucleic acid complex enclosed by the lipid membrane structure.

Lipid nanoparticles are preferably modified with PEG in some cases because this can increase retention in blood. Such lipid nanoparticles can accumulate in tumor tissues due to an EPR effect (Enhanced permeation and retention effect).

The diameter of a lipid nanoparticle can be for example about 110 nm to about 130 nm, such as about 120 nm. In one embodiment, the diameter of a lipid nanoparticle is about 125 nm. A suitable nanoparticle diameter can promote suitable delivery of the miRNA inhibiting complex used herein.

Preferred Embodiments

The preferred embodiments of the invention are described hereinafter. It is understood that the embodiments provided hereinafter are provided to better facilitate the understanding of the present invention, so that the scope of the present invention should not be limited by the following description. Thus, it is apparent that those skilled in the art can refer to the descriptions herein to make appropriate modifications within the scope of the present invention. It is also understood that the following embodiments of the invention can be used individually or as a combination.

(miRNA Inhibiting Complex)

In one aspect, the present invention provides an miRNA inhibiting complex comprising an RNA or an analog thereof, wherein the miRNA inhibiting complex comprises at least one double-stranded structure and an miRNA binding sequence, wherein two strands of the miRNA binding sequence are each bound to one of two strands on at least one end of the double-stranded structure, and wherein the miRNA inhibiting complex comprises at least one bridged nucleic acid (BNA). It is understood that the miRNA inhibiting complex used herein is used as an ideal raw material for a nucleic acid medicament or as a medicament itself because such an improved S-TuD or modified S-TuD (miRNA inhibiting complex) improved stability, suppressed the generation of impurities during the purification process, and surprisingly elevated biological activity by comprising at least one bridged nucleic acid (BNA).

In one embodiment, the BNA comprises a BNA that is bridged via at least one atom selected from the group consisting of oxygen and carbon on a position 2' side and via at least one atom selected from the group consisting of carbon and nitrogen and carbon on a position 4' side. Although not wishing to be bound by any theory, this can be used as a preferred BNA because oligonucleotide can be readily synthesized and formation of an RNA double strand is promoted.

In a preferred embodiment, the BNA used in the present invention can be any BNA described in the section of (Bridged nucleic acid (BNA) used in the present invention). For example, BNA-1 is a representative example. In a preferred embodiment, the BNA used in the present invention can be BNA-2, and more preferably BNA-3. For example, cEt, BNA$^{NC}$(NMe), 2',4'-methano bridged nucleic acid (LNA), or the like can be embodiments that can be used. BNA$^{NC}$(NMe) is particularly preferable. Although not wishing to be bound by any theory, this is because stability increased, double strand formation was promoted, and improvement in biological activity was observed by using the specific nucleic acid.

In another embodiment, cEt can be used. Although not wishing to be bound by any theory, this is because BNA (cEt) has thermal stability and mismatch identification similar to conventional LNA, while improving stability against nuclease.

In one embodiment, BNA used in the present invention is comprised in at least one of the strands of the double-stranded structure moiety and at least one strand of the miRNA binding sequence.

In another embodiment, a BNA used in the present invention is comprised in at least one of the strands of the double-stranded structure moiety. In another embodiment, a BNA used in the present invention is comprised in both strands of the double-stranded structure moiety.

In one embodiment, the complex of the invention can comprise one or more "double-stranded structure", and may have the same S-TuD structure as Japanese Patent No. 4936343 or Examples. For example, 3 or 4 double-stranded structures can be included consecutively in series. It is understood that such an embodiment is also encompassed by the present invention.

In one embodiment, the complex of the invention comprises two or more of the double-stranded structures, wherein strands comprising the miRNA binding sequence are each bound to one of two strands on one end of a first double-stranded structure of the double-stranded structures, and the other ends of the strands are each bound to one of two strands of a second double-stranded structure of the two or more of the double-stranded structures, so that the strands are sandwiched between the two or more of the double-stranded structures.

In another embodiment, an end of two strands comprising the miRNA binding sequence is bound via a linker in the present invention. In a preferred embodiment, the length of the linker is 1 to 10 bases long, more preferably 1 to 9 bases long, still more preferably 1 to 8 bases long, still more preferably 1 to 7 bases long, still more preferably 1 to 5 bases long, and may be 4 bases long, 3 bases long, 2 bases long, or 1 base long.

The length of a double-stranded structure in the miRNA inhibiting complex used herein may be any length as disclosed above, but is preferably a length of 4 base pairs or greater. In particular, at least one of the double-stranded structures comprised in the RNA complex of the invention (i.e., first double-stranded structure) has an important function for nuclear export of RNA complexes. The length of the double strand may be, for example, 10 to 50 or 15 to 50 base pairs, preferably 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, or 45 bases, or any of them or greater, or 50, 49, 48, 47, 46, 45, 44, 43, 42, 41, 40, 39, 38, 37, 36, 35, 34, 33, 32, 31, 30, 29, 28, 27, 26, 25, 24, 23, 22, 21, 20, 19, or 18 bases, or any one of them or less. In a preferred embodiment, the length of a base pair of a double-stranded structure is, for example, 10 to 30, 15 to 30, preferably 16 to 28, preferably 17 to 25, preferably 17 to 24, such as 17, 18, 19, 20, 21, 22, 23, or 24. High activity is exhibited at over 20 bp, but dsRNA greater than 20 bp can be a potential target of cleavage by Dicer in the cytoplasm. In order to avoid this, the double-stranded structure comprised in the complex of the invention can be structured to be 20 bp or less, such as 19 bp or less or 18 bp or less. A double-stranded structure comprised in an miRNA inhibiting complex is further disclosed in the following preferred embodiments. For example, said double-stranded structure may be 5 bp to 15 bp, 5 bp to 12 bp, 5 bp to 10 bp, 6 bp to 9 bp, 7 bp to 8 bp, or 10 bp to 12 bp.

The lower limit length of a double-stranded structure in the complex used in the present invention is not particularly limited as long as the activity is retained, but the length may be at least 4 bases long, at least 5 bases long, at least 6 bases long, at least 7 bases long, at least 8 bases long, preferably at least 9 bases long, and still more preferably at least 10 bases long. When there are two or more double strands, the base length thereof may be the same or different. While sufficient double-strand formation is confirmed and sufficient effect is demonstrated at 10 bases long, the length may optionally be, for example, at least 11 bases long, at least 12 bases long, at least 13 bases long, at least 14 bases long, at least 15 bases long, at least 16 bases long, at least 17 bases long, or at least 18 bases long.

The upper limit length of a double-stranded structure in the complex of the invention is not particularly limited as long as the activity is retained, but the length can be, for example, 100 bases long or less, 90 bases long or less, 80 bases long or less, 70 bases long or less, 60 bases long or less, 50 bases long or less, or the like.

When the miRNA inhibiting complex used herein comprises a second or greater double-stranded structure, the sequence and length of the double-stranded structures are not particularly limited. For example, the double-stranded structures may be shorter than the length of a first double-stranded structure in order to maintain the compactness of the entire miRNA inhibiting complex. The length of each double strand may be appropriately adjusted, but is, for example, 4 bp to 20 bp, such as 5 bp to 15 bp, 5 bp to 12 bp, 5 bp to 10 bp, 6 bp to 9 bp, or 7 bp to 8 bp.

While the complex used in the present invention is expected to exert its effect if there is one BNA, the complex can preferably comprise 2 or more, 3 or more, 4 or more, 5 or more, 6 or more, 7 or more, 8 or more, 9 or more, or 10 or more BNAs. However, a sufficient effect is achieved with about 6 BNAs so that the effect is not increased by including more BNAs in some cases. Thus, inclusion of around 6 BNAs (e.g., 4 to 8, 4 to 6, or the like) can be sufficient.

Further, the complex used in the present invention has stronger activity (action at low concentration) than conventional complexes. Examples of the effect that can be achieved by the complex of the invention include, but are not limited to, about 2-fold or greater, about 3-fold or greater, about 4-fold or greater, about 5-fold or greater, about 6-fold or greater, about 7-fold or greater, about 8-fold or greater, about 9-fold or greater, about 10-fold or greater, about 15-fold or greater, about 20-fold or greater, about 25-fold or greater, about 30-fold or greater, about 40-fold or greater, about 50-fold or greater, about 75-fold or greater, and about 100-fold or greater relative to the effect of conventional complexes. Thus, the complex of the invention achieves a significant effect of acting at 10 nM or less, 5 nM or less, 3 nM or less, 1 nM or less, 500 pM or less, 300 pM or less, 100 pM or less, 50 pM or less, 30 pM or less, 10 pM or less, 5 pM or less, 3 pM or less, or 1 pM or less.

In another embodiment, the complex of the invention comprises 2 to 5 and preferably 2 miRNA binding sequences. In one embodiment, the complex used in the present invention comprises the structure represented by

[Chemical Formula 34]

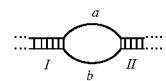

(C)

wherein I and II in the structure are double-stranded structures, and each of a and b of the structure comprises an miRNA binding sequence.

In another embodiment, the present invention provides each RNA constituting a complex comprising a BNA or an analog thereof (e.g., each single strand). Each of these RNAs or analogs thereof is within the scope of the present invention. A preferred embodiment for a single strand is substantially the same as that in a double-stranded structure, so that the same preferred embodiments can be employed.

In another aspect, the present invention provides a method of manufacturing the complex used in the present invention or a medicament comprising the same, comprising: A) synthesizing a protected entity of a single strand of an RNA of interest or an analog thereof and a protected entity of a complement thereof by chemical synthesis using a ribonucleic acid and a BNA; B) deprotecting each of the generated protected entity of the single strand and the complement thereof; C) placing each of the deprotected single strands under a double-strand forming condition to form a double strand; and optionally preparing a medicament with the resulting complex.

In still another embodiment, the present invention provides a method of manufacturing the RNA of the invention or an analog thereof, comprising: A) synthesizing a protected entity of a single strand of an RNA of interest or an analog thereof and a protected entity of a complement thereof by chemical synthesis using a ribonucleic acid and a BNA; B) deprotecting each of the generated protected entity of the single strand and the complement thereof; and optionally preparing a medicament with the resulting complex.

Such a method has been disclosed herein in detail in other sections. Examples also describe a demonstrative example. It is understood that those skilled in the art can manufacture various complexes, RNAs, or analogs thereof by referring to such descriptions.

(Nucleic Acid Molecule)

In another aspect, the present invention provides a nucleic acid molecule comprising: a sequence of 5'-CAGUGUU-3' and/or 5'-CAGUAUU-3'; and at least one bridged nucleic acid (BNA). Such a nucleic acid molecule can be utilized as a nucleic acid that can form an miRNA inhibiting complex to contribute to efficient materialization of miRNA inhibition. This can also be used to provide an anticancer agent or the like or a raw material thereof. In the sequence shown, a uracil base can be optionally a thymine base.

In another aspect, the present invention provides a nucleic acid molecule comprising: two miRNA binding sequences, one of the miRNA binding sequences comprising 5'-CAGUGUU-3' and the other miRNA binding sequence comprising 5'-CAGUAUU-3'; and at least one bridged nucleic acid (BNA). Such a nucleic acid molecule can be utilized as an miRNA inhibiting complex to contribute to efficient materialization of miRNA inhibition. This can also be used to provide an anticancer agent or the like or a raw material thereof. In the sequence shown, a uracil base can be optionally a thymine base.

In another aspect, the present invention provides a nucleic acid molecule comprising an miRNA binding sequence comprising the sequence of SEQ ID NO: 1 and an miRNA binding sequence comprising the sequence of SEQ ID NO: 2. In the sequence shown, a uracil base can be optionally a thymine base.

This nucleic acid molecule comprises a BNA, preferably an miRNA binding sequence comprising the sequence of SEQ ID NO: 3 and the sequence of SEQ ID NO: 4. In the sequence shown, a uracil base can be optionally a thymine base.

In one embodiment, the present invention provides a nucleic acid molecule comprising: the sequence of SEQ ID NO: 5 and the sequence of SEQ ID NO: 6, and at least one bridged nucleic acid (BNA). Preferably, the present invention provides a nucleic acid molecule comprising the sequence of SEQ ID NO: 9 and the sequence of SEQ ID NO: 10.

While the sequences are described as a sequence of an RNA molecule, both a uracil base and a thymine base complementarily bind to an adenine base, so that those skilled in the art understand that the base indicated as a uracil base in the sequence can be changed to a thymine base. Thus, the uracil base may be optionally a thymine base in the sequences described herein.

In one aspect, the present invention provides a composition comprising the nucleic acid molecule of the invention. The composition can be for preventing or treating tumor, wherein the tumor can be, for example, carcinoma.

In a specific embodiment, target tumor can be colon cancer, lung cancer, or breast cancer. Alternatively, the composition can be for promoting epithelial-mesenchymal transition of the tumor.

In one embodiment, an miRNA inhibiting complex or nucleic acid molecule is in a form contained in a carrier for nucleic acid delivery in the composition of the invention.

Such a carrier is selected from the group consisting of lipid nanoparticles (LNP), cationic liposome, noncationic liposome, cationic polymer, noncationic polymer, β-glucan, atelocollagen, PLGA nanoparticles, surfactant peptide, and super apatite. Although not wishing to be bound by any theory, decomposition of a nucleic acid molecule can be reduced by being comprised in such a carrier. Advantageously, this can be targeted to a target to enhance the utility as a nucleic acid medicament.

In one embodiment, the carrier used is an LNP, and the LNP comprises a cationic lipid.

Such an LNP can comprise a cationic lipid, a helper lipid, and a PEGylated lipid. Preferably, the cationic lipid comprises a tertiary amine and/or disulfide bond in a molecule.

(Composition Comprising an miRNA Inhibiting Complex and a Carrier for Nucleic Acid Delivery)

In one aspect, the present invention provides a composition comprising an miRNA inhibiting complex comprising an RNA or an analog thereof and a carrier for nucleic acid delivery. In this regard, the comprised miRNA inhibiting complex comprises at least one double-stranded structure and an miRNA binding sequence, wherein two strands of the miRNA binding sequence are each bound to one of two strands on at least one end of the double-stranded structure, and wherein the miRNA inhibiting complex comprises at least one bridged nucleic acid (BNA). The BNA used in this regard can be any BNA described in (Bridged nucleic acid (BNA) used in the present invention) herein. The composition of the invention can utilize any embodiment described in the section of (miRNA inhibiting complex), (Inhibition of miRNA), (Nucleic acid molecule), (Medicament), or (DDS), and any form described elsewhere herein as an miRNA inhibiting complex that is comprised.

In one aspect, the present invention provides a pharmaceutical composition comprising a composition comprising an miRNA inhibiting complex comprising an RNA or an analog thereof and a carrier for nucleic acid delivery. The BNA used in this regard can be any BNA described in (Bridged nucleic acid (BNA) used in the present invention) herein. The composition of the invention can utilize any embodiment described in the section of (miRNA inhibiting complex), (Inhibition of miRNA), (Nucleic acid molecule), (Medicament), or (DDS), and any form described elsewhere herein as an miRNA inhibiting complex that is comprised.

In another aspect, the present invention provides a composition for delivering an miRNA inhibiting complex to a desirable site, comprising the miRNA inhibiting complex comprising an RNA or an analog thereof and a carrier for nucleic acid delivery. The BNA used in this regard can be any BNA described in (Bridged nucleic acid (BNA) used in the present invention) herein. The composition of the invention can utilize any embodiment described in the section of (miRNA inhibiting complex), (Inhibition of miRNA), (Nucleic acid molecule), (Medicament), or (DDS), and any form described elsewhere herein as an miRNA inhibiting complex that is comprised.

In one embodiment, the BNA comprises a BNA that is bridged via at least one atom selected from the group consisting of oxygen and carbon on the position 2' side and via at least one atom selected from the group consisting of carbon and nitrogen and carbon on the position 4' side in the composition comprising an miRNA inhibiting complex and a carrier for nucleic acid delivery of the invention.

In a preferred embodiment, the BNA used in the present invention can be any BNA described in the section of (Bridged nucleic acid (BNA) used in the present invention). For example, BNA-1 is a representative example. In a preferred embodiment, the BNA used in the present invention can be BNA-2, and more preferably BNA-3. For example, cEt, BNA$^{NC}$(NMe), 2',4'-methano bridged nucleic acid (LNA), or the like can also be embodiments that can be used. BNA$^{NC}$(NMe) is particularly preferable. Although not wishing to be bound by any theory, this is because stability increased, double strand formation was promoted, and improvement in biological activity was observed by using the specific nucleic acid. In another embodiment, cEt can be used. Although not wishing to be bound by any theory, this is because BNA (cEt) has thermal stability and mismatch identification similar to conventional LNA, while improving stability against nuclease.

In one embodiment, the complex of the invention comprises two or more of the double-stranded structures, wherein strands comprising the miRNA binding sequence are each bound to one of two strands on one end of a first double-stranded structure of the double-stranded structures, and the other ends of the strands are each bound to one of two strands of a second double-stranded structure of the two or more of the double-stranded structures, so that the strands are sandwiched between the two or more of the double-stranded structures.

The lower limit length of a double-stranded structure in the complex used in the present invention is not particularly limited as long as the activity is retained, but the length may be at least 4 bases long, at least 5 bases long, at least 6 bases long, at least 7 bases long, at least 8 bases long, preferably at least 9 bases long, and still more preferably at least 10 bases long. When there are two or more double strands, the base length thereof may be the same or different. While sufficient double-strand formation is confirmed and sufficient effect is demonstrated at 10 bases long, the length may optionally be, for example, at least 11 bases long, at least 12 bases long, at least 13 bases long, at least 14 bases long, at least 15 bases long, at least 16 bases long, at least 17 bases long, or at least 18 bases long.

The upper limit length of a double-stranded structure in the complex of the invention is not particularly limited as long as the activity is retained, but the length can be, for example, 100 bases long or less, 90 bases long or less, 80 bases long or less, 70 bases long or less, 60 bases long or less, 50 bases long or less, or the like.

In another embodiment, the complex of the invention comprises 2 to 5 miRNA binding sequences, and preferably comprises 2 miRNA binding sequences.

In one embodiment, the complex used in the present invention comprises the structure represented by

[Chemical Formula 35]

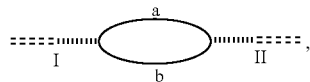

(C)

wherein I and II in the structure can have double-stranded structures, and each of a and b of the structure comprises an miRNA binding sequence.

In a preferred embodiment, the miRNA binding sequence comprises 5'-CAGUGUU-3' and/or 5'-CAGUAUU-3'. Preferably, the miRNA inhibiting complex comprises two miRNA binding sequences, one of the miRNA binding sequences comprising 5'-CAGUGUU-3' and the other miRNA binding sequence comprising 5'-CAGUAUU-3'. In the sequence shown, a uracil base can be optionally a thymine base.

In one specific embodiment, the composition comprising an miRNA inhibiting complex and a carrier for nucleic acid delivery of the invention comprises an miRNA binding sequence comprising the sequence of SEQ ID NO: 1, an miRNA binding sequence comprising the sequence of SEQ ID NO: 2, and a BNA, and preferably comprises an miRNA binding sequence comprising the sequence of SEQ ID NO: 3 and the sequence of SEQ ID NO: 4. In the sequence shown, a uracil base can be optionally a thymine base.

One embodiment provides a nucleic acid molecule wherein a complex comprises the sequence of SEQ ID NO: 5, the sequence of SEQ ID NO: 6, and at least one bridged nucleic acid (BNA) in the composition comprising an miRNA inhibiting complex and a carrier for nucleic acid delivery of the invention. Preferably, a complex comprises the sequence of SEQ ID NO: 9 and the sequence of SEQ ID NO: 10 in the composition comprising an miRNA inhibiting complex and a carrier for nucleic acid delivery of the invention. In the sequence shown, a uracil base can be optionally a thymine base.

In one embodiment, the carrier comprised in the composition comprising an miRNA inhibiting complex and a carrier for nucleic acid delivery of the invention is selected from the group consisting of lipid nanoparticles (LNP), a cationic liposome, a non-cationic liposome, a cationic polymer, a non-cationic polymer, β-glucan, an atelocollagen, PLGA nanoparticles, a surfactant peptide, and a super apatite. In addition, any embodiment described in the section of (DDS) and any form described elsewhere herein can also be used.

In a preferred embodiment, the carrier used in the present invention is an LNP, and the LNP comprises a cationic lipid. More preferably, an LNP can comprise a cationic lipid, a helper lipid, and a PEGylated lipid. Specifically, the cationic lipid can comprise a tertiary amine and/or disulfide bond in a molecule.

(Composite Cationic Lipid)

One embodiment focuses on the carrier used in the present invention. The present invention provides a composition comprising: a lipid membrane structure comprising, as a constituent lipid of a membrane, a compound represented by formula (1)

[Chemical Formula 36]

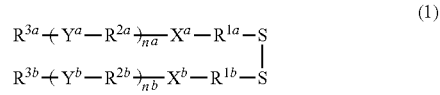

(1)

wherein
X$^a$ and X$^b$ are independently X$^1$ or X$^2$,

[Chemical Formula 37]

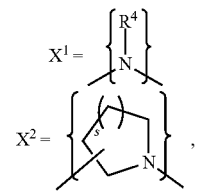

s is 1 or 2,
R$^4$ represents an alkyl group with 1 to 6 carbons,
n$^a$ and n$^b$ are independently 1,
R$^{1a}$ and R$^{1b}$ independently represent an alkylene group with 1 to 6 carbons,
R$^{2a}$ and R$^{2b}$ independently represent an alkylene group with 1 to 6 carbons,
Y$^a$ and Y$^b$ independently represent an ester bond, an amide bond, a carbamate bond, an ether bond, or a urea bond,
R$^{3a}$ and R$^{3b}$ independently represent a sterol residue, a lipophilic vitamin derivative residue, or an aliphatic hydrocarbon group with 12 to 22 carbons, a sterol residue is a cholesteryl group, a cholestaryl group, stigmasteryl group, a β-sitosteryl group, a lanosteryl group, or an ergosteryl group, and
a lipophilic vitamin is retinoic acid, retinol, retinal, ergosterol, 7-dehydrocholesterol, calciferol, cholecalciferol, dihydroergocalciferol, dihydrotachysterol, tocopherol, or tocotrienol, or formula (4)

[Chemical 38]

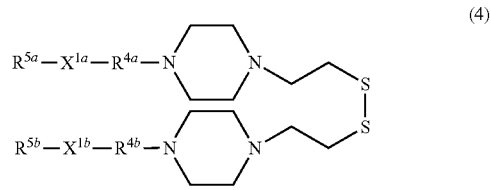

(4)

wherein $R^{4a}$ and $R^{4b}$ are independently an alkylene group or oxydialkylene group with 8 carbons or less, $X^{1a}$ and $X^{1b}$ are independently an ester bond, an amide bond, a carbamate bond, or an ether bond, and $R^{5a}$ and $R^{5b}$ independently represent a sterol residue, a lipophilic vitamin derivative residue, or an aliphatic hydrocarbon group with 13 to 23 carbons; and a nucleic acid complex encapsulated by the lipid membrane structure;

wherein the nucleic acid complex is an miRNA inhibiting complex comprising an RNA or an analog thereof, wherein the miRNA inhibiting complex comprises at least one double-stranded structure and an miRNA binding sequence, wherein two strands of the miRNA binding sequence are each bound to one of two strands on at least one end of the double-stranded structure, and the miRNA inhibiting complex comprises at least one bridged nucleic acid (BNA). The BNA used in this regard can be any BNA described in (Bridged nucleic acid (BNA) used in the present invention) herein. The composition of the invention can utilize any embodiment described in the section of (miRNA inhibiting complex), (Inhibition of miRNA), (Nucleic acid molecule), (Medicament), or (DDS), and any form described elsewhere herein as an miRNA inhibiting complex that is comprised.

In this regard, in a preferred embodiment, $X^a$ and $X^b$ are independently $X^2$.

In a preferred embodiment, $R^{3a}$ and $R^{3b}$ are independently a lipophilic vitamin derivative residue or an aliphatic hydrocarbon group with 12 to 22 carbons.

In a preferred embodiment, $R^{3a}$ and $R^{3b}$ are independently a lipophilic vitamin derivative residue.

In a more preferred embodiment, the lipophilic vitamin derivative residue is a residue derived from a reactant of a lipophilic vitamin having a hydroxyl group and succinic acid anhydride or a glutaric acid anhydride.

In a preferred embodiment, $R^{3a}$ and $R^{3b}$ are independently an aliphatic hydrocarbon group with 12 to 22 carbons.

In this regard, in a preferred embodiment, $R^{4a}$ and $R^{4b}$ in formula (4) are independently an alkylene group with 8 carbons or less.

In a preferred embodiment, $X^{1a}$ and $X^{1b}$ in formula (4) are ester bonds.

In a preferred embodiment, $R^{5a}$ and $R^{5b}$ in formula (4) are independently a lipophilic vitamin residue or an aliphatic hydrocarbon group with 13 to 23 carbons.

In a more preferred embodiment, $R^{5a}$ and $R^{5b}$ in formula (4) are independently a lipophilic vitamin residue.

In a preferred embodiment, $R^{5a}$ and $R^{5b}$ in formula (4) are independently an aliphatic hydrocarbon group with 13 to 23 carbons.

Examples of particularly preferred cationic lipids used in the present invention include [Chemical Formula 39]

[Chemical Formula 39]

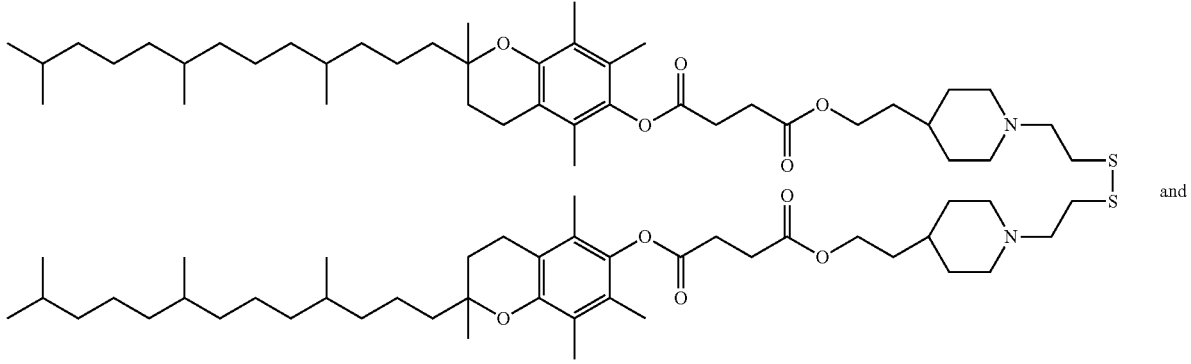

and

[Chemical Formula 40]

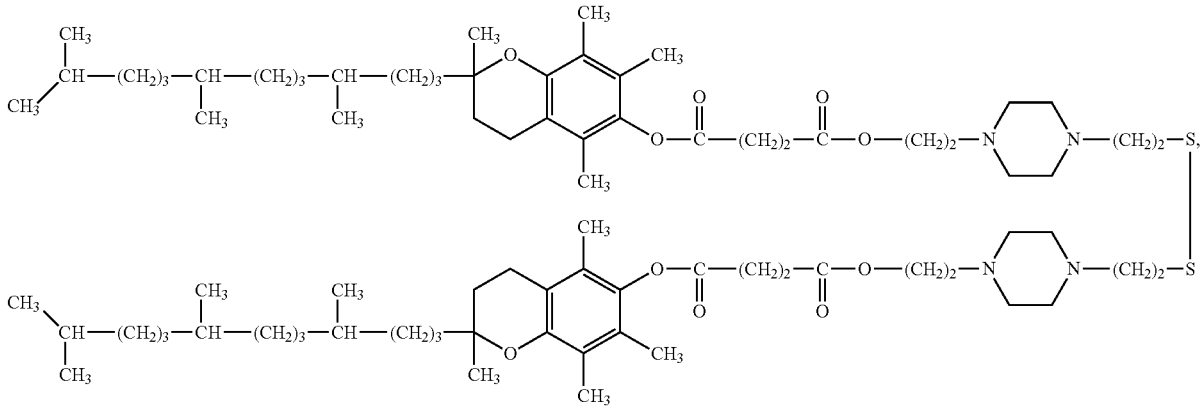

which are commercially available as COATSOME SS-33/4PE-15® (NOF Corporation) and COATSOME SS-33/1PZ-21@ (NOF Corporation), respectively.

In a preferred embodiment, the BNA is $BNA^{NC}(NMe)$

In another preferred embodiment, the miRNA inhibiting complex used in the present invention comprises two or more of the double-stranded structures, wherein strands comprising the miRNA binding sequence are each bound to one of two strands on one end of a first double-stranded structure of the double-stranded structures, and the other ends of the strands are each bound to one of two strands of a second double-stranded structure of the two or more of the double-stranded structures, so that the strands are sandwiched between the two or more of the double-stranded structures.

In one embodiment, the miRNA inhibiting complex comprises two miRNA binding sequences. In this regard, the miRNA inhibiting complex preferably comprises the structure depicted in FIG. 2, and I and II in the structure are double-stranded structures, and each of a and b of the structure comprises an miRNA binding sequence.

In a preferred embodiment, the miRNA binding sequence used in the present invention comprises 5'-CAGUGUU-3' and/or 5'-CAGUAUU-3'. Preferably, the miRNA inhibiting complex comprises two miRNA binding sequences, one of the miRNA binding sequences comprising 5'-CAGUGUU-3' and the other miRNA binding sequence comprising 5'-CAGUAUU-3'

In a preferred embodiment, the miRNA inhibiting complex used in the present invention comprises an miRNA binding sequence comprising the sequence of SEQ ID NO: 1, an miRNA binding sequence comprising the sequence of SEQ ID NO: 2, and a BNA, preferably an miRNA binding sequence comprising the sequence of SEQ ID NO: 3 and the sequence of SEQ ID NO: 4. In the sequence shown, a uracil base can be optionally a thymine base.

In one embodiment, the present invention provides a nucleic acid molecule, wherein a complex comprises the sequence of SEQ ID NO: 5, the sequence of SEQ ID NO: 6, and at least one bridged nucleic acid (BNA). Preferably, the complex comprises the sequence of SEQ ID NO: 9 and the sequence of SEQ ID NO: 10 in the present invention. In the sequence shown, a uracil base can be optionally a thymine base.

As used herein, "or" is used when "at least one or more" of the listed matters in the sentence can be employed. When explicitly described herein as "within the range of two values", the range also includes the two values themselves.

Reference literatures such as scientific literatures, patents, and patent applications cited herein are incorporated herein by reference to the same extent that the entirety of each document is specifically described.

The present invention has been described while showing preferred embodiments to facilitate understanding. The present invention is described hereinafter based on Examples. The aforementioned description and the following Examples are not provided to limit the present invention, but for the sole purpose of exemplification. Thus, the scope of the present invention is not limited to the embodiments and Examples that are specifically described herein and is limited only by the scope of claims. It should be noted that the documents cited herein are all incorporated as a part of the present specification.

EXAMPLES

The Examples of the invention are described hereinafter. A synthesis example is first provided, and then Examples such as animal model experiments and the like demonstrating biological activity thereof are provided. Animal experiments and the like were conducted in compliance with the code of ethical of Chiba University, animal protection laws and associated regulations, government regulation stipulated for experimental animals, and the like.

The nucleoside analogs and oligonucleotide analogs of the invention were synthesized in accordance with the following synthesis schemes.

(Synthesis of Oligonucleotides)

Oligonucleotides were synthesized using an nS-8II synthesizer or AKTA oligopilot synthesizer. A commercially available controlled pore glass solid phase carrier (e.g., 2'-O-methyl-RNA CPG Link Technologies), 2'-O-methyl-RNA phosphoramidite having a standard protecting group, i.e., 5'-O-dimethoxytrityl-N6-benzoyladenosine-2'-O-methyl-3'-O—N,N'-diisopropylphosphoramidite, 5'-O-dimethoxytrityl-N4-acetylcytidine-2'-O-methyl-3'-O—N,N'-diisopropylphosphoramidite, 5'-O-dimethoxytrityl-N2-isobutylguanosine-2'-O-methyl-3'-O—N,N'-diisopropylphosphoramidite, and 5'-O-dimethoxytrityluridine-2'-O-methyl-3'-O—N,N'-diisopropylphosphoramidite (which are manufactured by Sigma-Aldrich), and 2',4'-BNA$^N$c (2'-O,4'-C-aminomethylene bridged nucleic acid) thymidine phosphoramidite, i.e., 2'-O,4'-C-aminomethylene-5'-O-dimethoxytrityl-thymidine-N,N'-diisopropylphosphoramidite, 2',4'-BNA$^N$c adenosine phosphoramidite, i.e., 2'-O,4'-C-aminomethylene-5'-O-dimethoxytrityl-N6-benzoyladenosine-N,N'-diisopropylphosphoramidite (which are manufactured by BNA), and LNA (Locked nucleic acid) (2'-O,4'-C-methyleneribonucleic acid) thymidine phosphoramidite, i.e., 2'-O,4'-C-methylene-5'-O-dimethoxytritylthymidine-N,N'-diisopropylphosphoramidite (manufactured by Exiqon) were used in oligonucleotide synthesis. All phosphoramidites were used in acetonitrile ($CH_3CN$) at a concentration of 0.1 M. For 2'-O-methyl RNA, BNA and LNA, linking/reuse time of 15 minutes was used. The activating agent was 5-benzylmercapto-tetrazole (0.25 M, Wako Pure Chemical Industries), and PO-oxidation used iodine/water/pyridine. For PS-phosphorothioation, commercially available sulfuration reagents for automated oligonucleotide synthesizers (i.e., EIDTH, DDTT, PADS, Beucage reagents, and the like) were used with pyridine.

Deprotection I (Nucleobase Deprotection)

After the completion of synthesis, the synthesized carrier was transferred to a glass bottle. Oligonucleotides were cleaved from the carrier while simultaneously deprotecting a base and a phosphoric acid group at 45° C. for 13 hours using 15 mL of a mixture of equal parts aqueous 40% methylamine solution and 33% methylamine ethanol solution for 1 g of carrier. An ethanol ammonium mixture was then filtered and placed in a new 250 mL bottle. The carrier was washed with 2×40 mL of ethanol/water (1:1 v/v). The solvent was then distilled away for exsiccation with a rotary evaporator (roto-vap).

(HPLC Purification)

Oligonucleotides were purified by reverse phase ion pair HPLC with a Source 15 RPC gel column. The buffer was 5% $CH_3CN$, 0.1 M triethylamine acetic acid buffer (pH 7.0) (buffer A) and 90% $CH_3CN$, 0.1 M triethylamine acetic acid buffer (pH 7.0) (buffer B). Fractions comprising a full-length oligonucleotide were pooled while retaining a dimethoxytrityl group at the 5' end, and were subjected to the next purification. The oligonucleotide pool was then purified by Source 30Q anion pair HPLC. The solution and buffer were 0.6% trifluoroacetate (solution A), 20 mM sodium phosphate buffer (pH 7.5) (buffer C), and 2 M sodium chloride (buffer D) in 20 mM sodium phosphate buffer. After having a dimethoxytrityl group leave using solution A, fractions comprising a full-length oligonucleotide were pooled, desalinated, and then lyophilized. The compound was ultimately analyzed with MALDI-TOF/MS and reverse phase HPLC.

(Double-Strand Formation)

After a purified single-stranded oligonucleotide was dissolved into distilled water, the oligonucleotide concentration was determined by measuring absorbance using a UV spectrophotometer. Each complementary strand was mixed to be at an equimolar concentration by using the determined concentration and was heated at 95° C. for 10 minutes then gradually cooled to allow the formation of a double strand. Double-strand formation was confirmed by non-denaturing gel electrophoresis.

Example 1: Suppression of Tumor In Vivo with Improved S-TuD

<Materials and Methods>
Cell Culture

Triple negative breast cancer cell strain SUM149PT (also known as SUM149) was obtained from Asterand and cultured in Ham's F-12 medium (SUM149PT medium) comprising 5% foetal bovine serum (FBS), 10 mM HEPES, 5 µg/ml Insulin, 1 µg/ml Hydrocortisone, and 5 µg/ml Gentamicin at 37° C.

Animal Experiment

Female BALB/c nude mice were purchased from Japan SLC. 6 week old mice were used in all experiments. Cells were suspended in a SUM149PT medium, and equal amount of Matrigel (BD) was mixed in and then injected into mammary fat pad. The tumor volume was measured with a digital caliper.

miRNA Inhibiting Complex

An miRNA inhibiting complex was prepared in accordance with the protocol described above. FIG. 4 depicts the structures of (1) S-TuD-141/200c-1_17-pf-S10-BT6-MBSB1 (having an MBS for miR-141 and miR-200c) and (2) S-TuD-NCs-S10-BT6-MBSB1-s (MBS does not have a complementary sequence to miR) used in this Example. Lower case letters in the sequence indicate the location substituted with BNA$^{NC}$(NMe)

The day on which 5×10$^5$ SUM149PT cells were injected into mouse mammary fat pad was considered day 0. On days 69, 76, 83, 90, 97, 104, and 111, (1) S-TuD-141/200c-1_17-pf-S10-BT6-MBSB1 and (2) S-TuD-NCs-S10-BT6-MBSB1-s (Naked, 3 mg/kg) were administered into the tail vein and tumor.

After administration, the mouse body weight and tumor volume were measured over time.

<Results>

Figure 5:
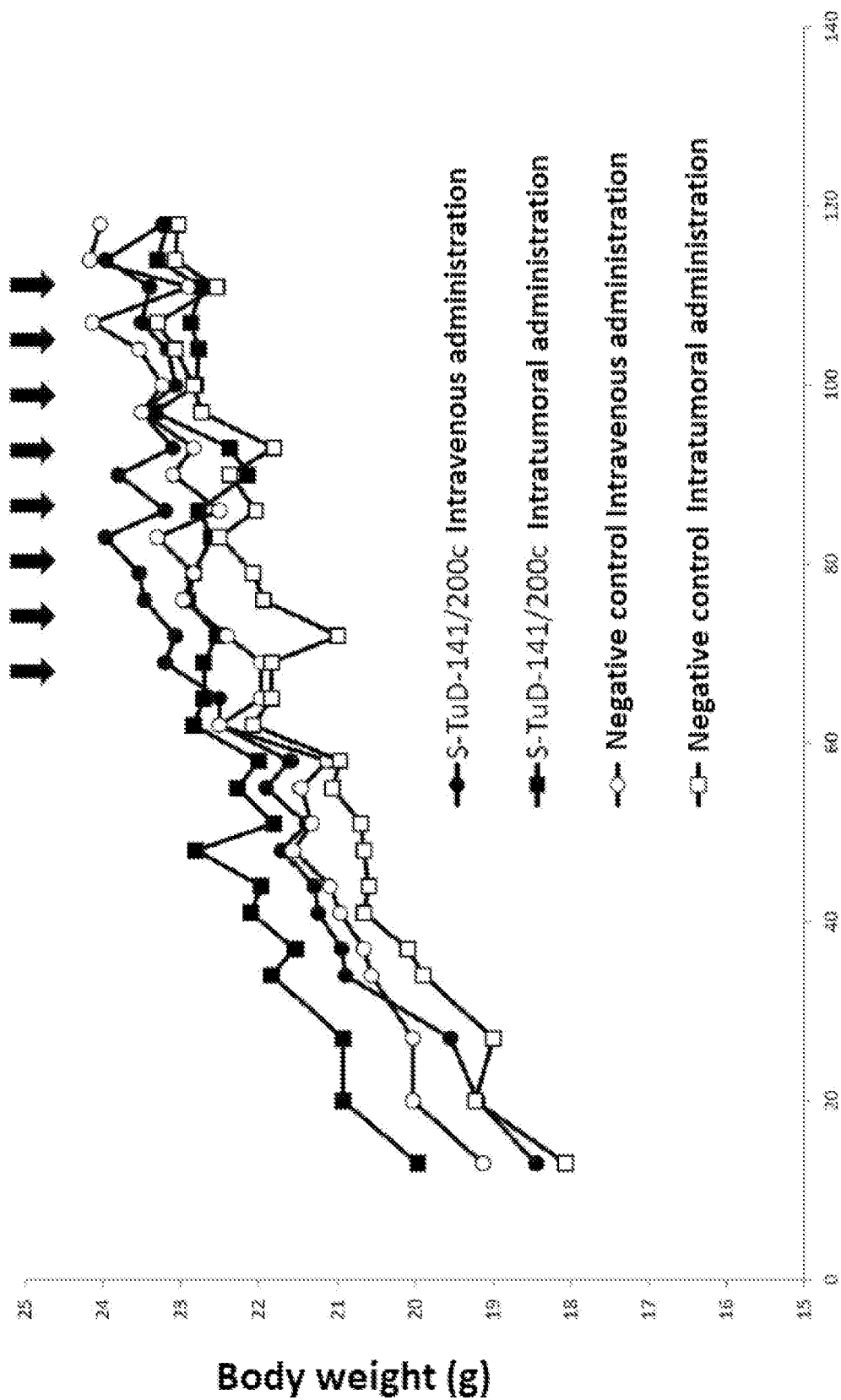
FIG. 5 is a diagram showing the change in the body weight (g) over time of tumor transplanted mice administered with (1) S-TuD-141/200c-1_17-pf-S10-BT6-MBSB1 (S-TuD-141/200c) or (2) S-TuD-NCs-S10-BT6-MBSB1-s (S-TuDNCs) intravenously to the tail or intratumorally. The arrows indicate the timing of administration.
Figure 6:
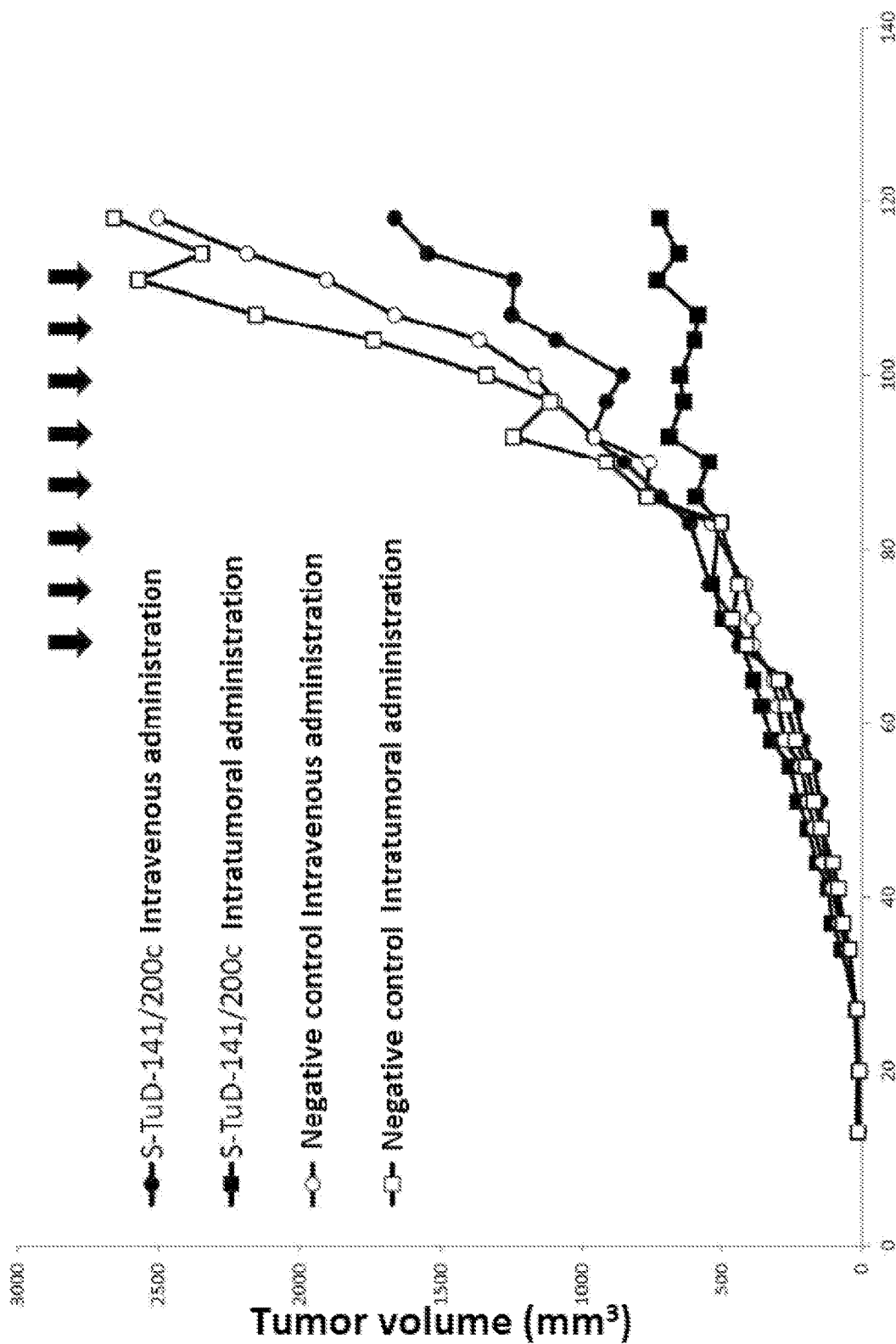
FIG. 6 is a diagram showing the change in the tumor volume ($mm^3$) over time in tumor transplanted mice administered with (1) S-TuD-141/200c-1_17-pf-S10-BT6-MBSB1 (S-TuD-141/200c) or (2) S-TuD-NCs-S10-BT6-MBSB1-s(S-TuDNCs) intravenously to the tail or intratumorally. The arrows indicate the timing of administration.

The results are shown in FIGS. 5 and 6.

As shown in FIG. 5, there was no change in the body weight of mice administered with each S-TuD through each route without side effects from S-TuD, suggesting that the S-TuD can be safely used.

As shown in FIG. 6, S-TuD-141/200c-1_17-pf-S10-BT6-MBSB1 (S-TuD-141/200c) reduced tumor growth compared to S-TuD-NCs-S10-BT6-MBSB1 (S-TuDNCs). This demonstrates that the hybrid miRNA inhibiting complex of the invention successfully inhibited two miRNAs (miR-141 and miR-200c), and thereby suppress tumor growth.

While the tumor growth was reduced with intravenous administration, tumor growth was significantly inhibited especially with intratumor administration, suggesting that delivery of S-TuD-141/200c to tumor using a suitable delivery system is very effective for treating or preventing tumor.

Since TuD is a system expressed from a vector, miRNA could not be successfully inhibited unless administered ex vivo by introducing a viral vector into cells in advance. Since the improved S-TuD of the invention has higher capability to inhibit miRNAs and better serum stability compared to conventional S-TuD, in vivo miRNA inhibition is significantly improved. For this reason, it is demonstrated when the improved S-TuD of the invention is used that inhibition of miRNAs was able to be achieved by intratumor administration or intravenous administration, i.e., in vivo.

Example 2: Suppression of Tumor In Vivo with Improved S-TuD Using DDS

In this Example, a drug delivery system (DDS) suitable for delivery of the improved S-TuD of the invention was studied.

<Materials and Methods>

Preparation of an animal tumor model, miRNA inhibiting complex, and the like was the same as Example 1, except for using a drug delivery system.

Lipid Nanoparticles (LNP)

Figure 7:
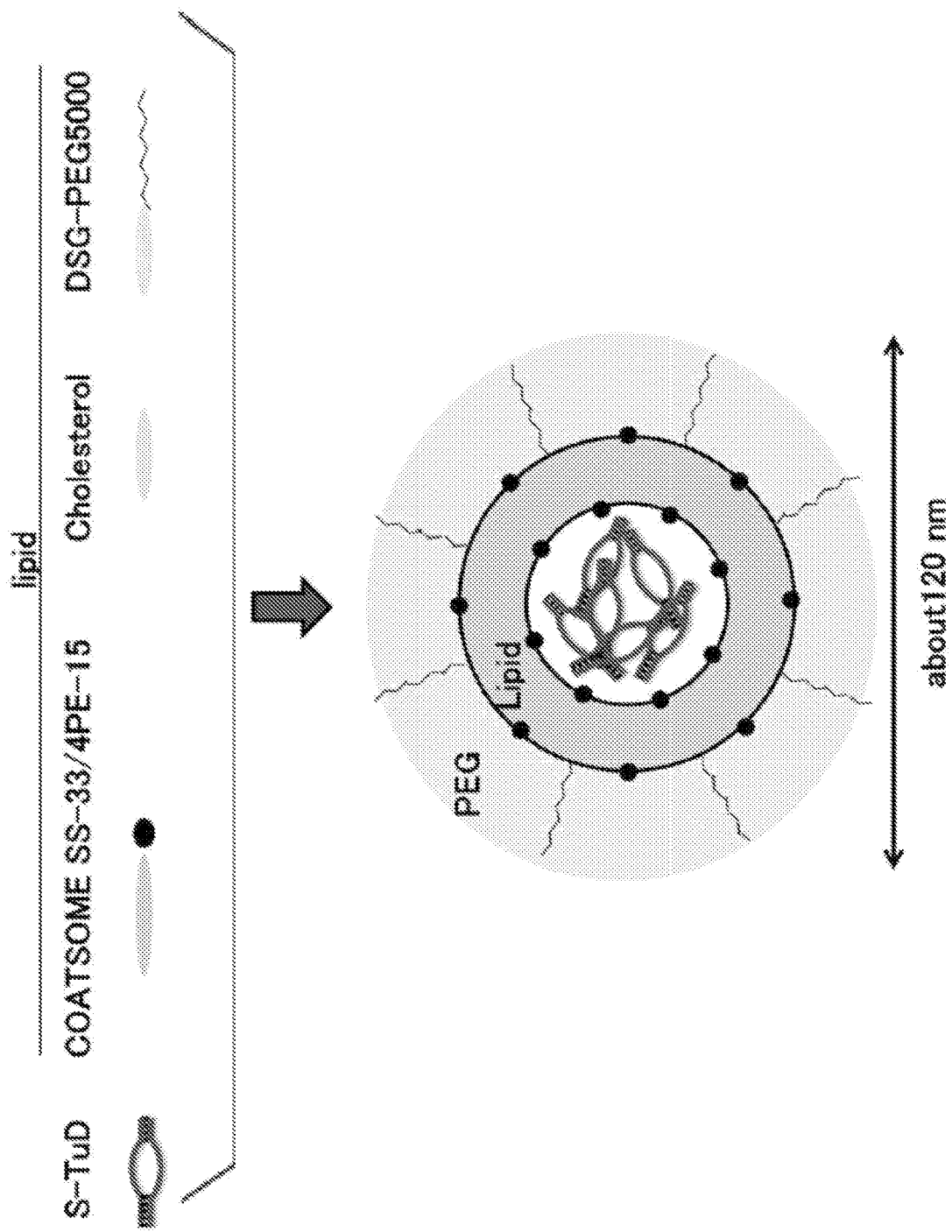
FIG. 7 is a diagram schematically depicting the composition of the lipid nanoparticles used in Example 2.

Lipid nanoparticles shown in FIG. 7 were used as the DDS. The lipid nanoparticles comprised the following components:

COATSOME SS-33/4PE-15

[Chemical Formula 41]

cholesterol

[Chemical Formula 42]

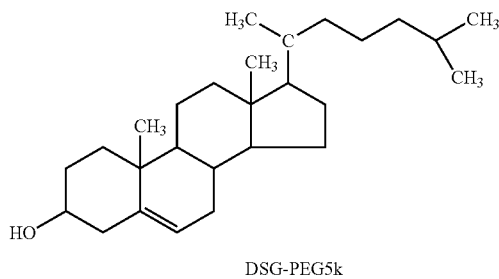

DSG-PEG5k

[Chemical Formula 43]

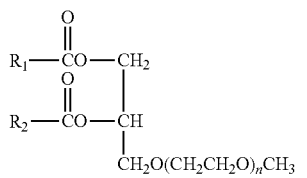

wherein $R_1$ and $R_2$ are C18:0 acyl.

Composition of LNP

Lipid nanoparticles with the following component ratio were prepared.

Formulation 1:

| Lipid | 6000 nmol |
|---|---|
| S-TuD | 6.72 nmol |
| Lipid/S-TuD ratio | 1000 |
| Recovery rate (%) | 81 |
| Encapsulation rate (%) | 35 |
| Diameter (d. nm) | 125 |

Formulation 2:

| Lipid | 3000 nmol |
|---|---|
| S-TuD | 6.72 nmol |
| Lipid/S-TuD ratio | 250 |
| Recovery rate (%) | 56 |
| Encapsulation rate (%) | 33 |
| Diameter (d. nm) | 122.2 |

Formulation 3:

| Lipid | 3000 nmol |
|---|---|
| S-TuD | 3.36 nmol |
| Lipid/S-TuD ratio | 1000 |
| Recovery rate (%) | 55 |
| Encapsulation rate (%) | 40 |
| Diameter (d. nm) | 114.6 |

Formulation 4:

| Lipid | 6000 nmol |
|---|---|
| S-TuD | 13.4 nmol |
| Lipid/S-TuD ratio | 500 |
| Recovery rate (%) | 94 |
| Encapsulation rate (%) | 28 |
| Diameter (d. nm) | 116.8 |

LNPs with the composition of Formulation 1 were used for further study in vivo. The ratio of each component for mice was

| S-TuD | 1 mg/kg |
|---|---|
| COATSOME SS-33/4PE-15 | 430 nmol/mouse |
| Cholesterol | 185 nmol/mouse |
| DSG-PEG5k | 18 nmol/mouse. |

With the date of transplantation of tumor cells being day 0, S-TuD-141/200c-1_17-pf-S10-BT6-MBSB1 (LNP-S-TuD-141/200c) (1 mg/kg) encapsulated in the LNP or PBS was injected intravenously on days 29, 36, 43, 50, and 57 from the tail vein into mice, which were transplanted with $5 \times 10^5$ SUM149PT cells into mammary fat pad in the same manner as Example 1. While LNP-S-TuD-141/200c (3 mg/kg) was also administered on day 29, this was not subsequently administered at this dosage due to one case of death.

<Results>

Figure 8:
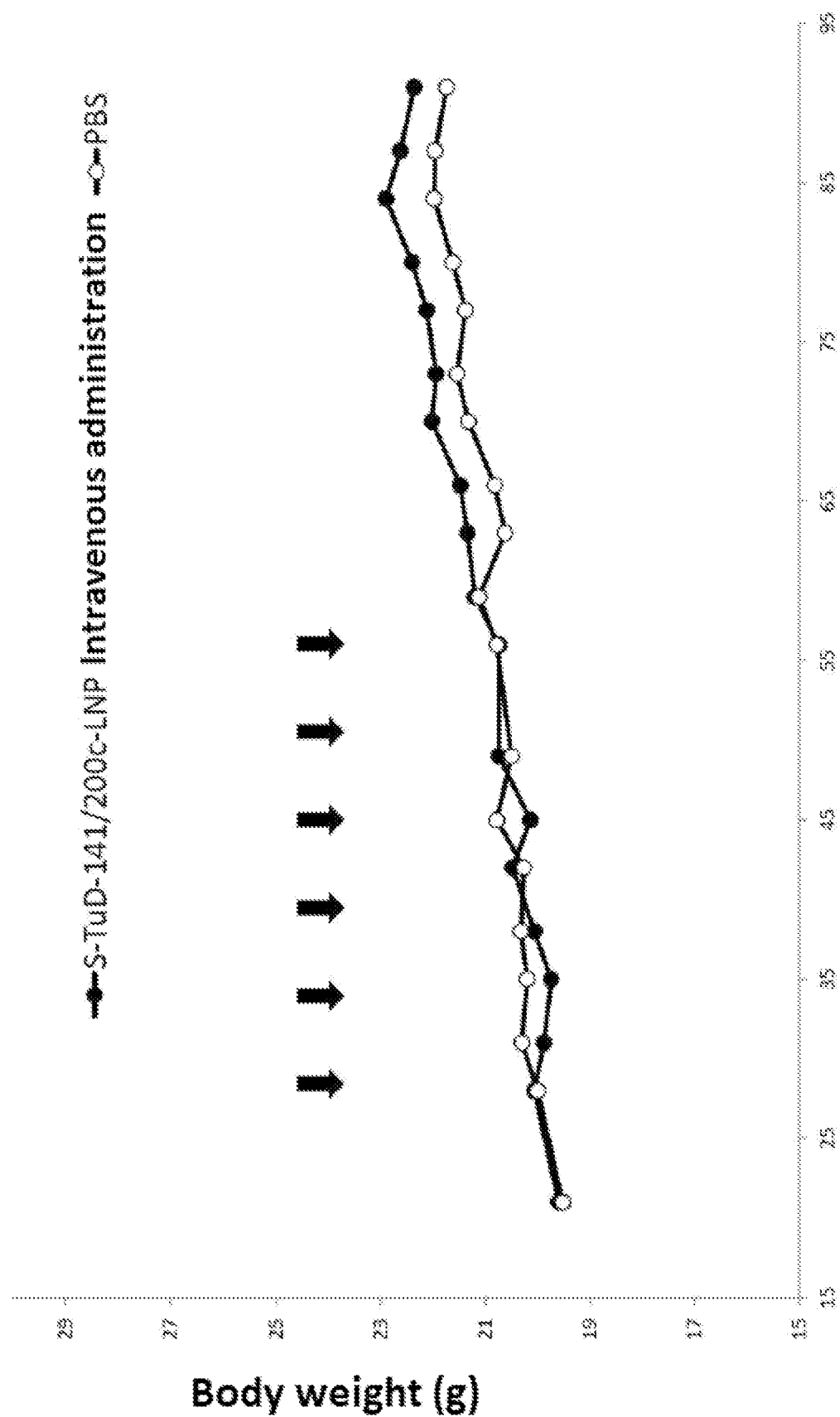
FIG. 8 is a diagram showing the change in the body weight (g) over time of tumor transplanted mice injected with S-TuD-141/200c-1_17-pf-S10-BT6-MBSB1 (LNP-S-TuD 141/200c) encapsulated in lipid nanoparticles or PBS intravenously to the tail. The arrows indicate the timing of administration.
Figure 9:
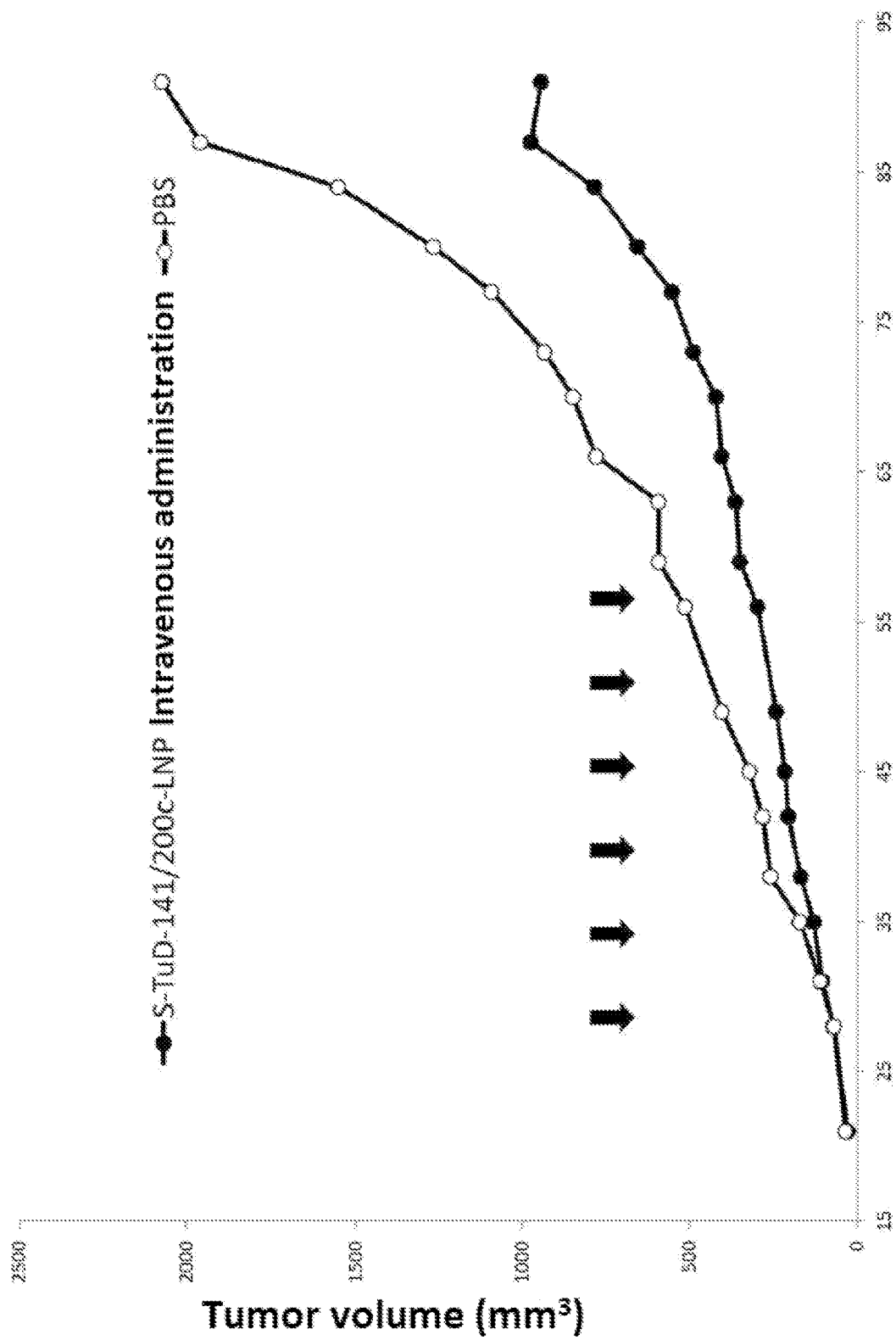
FIG. 9 is a diagram showing the change in the tumor volume ($mm^3$) over time of tumor transplanted mice injected with S-TuD-141/200c-1_17-pf-S10-BT6-MBSB1 (LNP-S-TuD 141/200c) encapsulated in lipid nanoparticles or PBS intravenously to the tail. The arrows indicate the timing of administration.

The results are shown in FIGS. 8 and 9. As shown in FIG. 8, there was no significant change in the body weight of mice administered with LNP-S-TuD-141/200c (1 mg/kg) or PBS, and side effects were not observed, suggesting that the LNP can be safely used.

As shown in FIG. 9, administration of LNP-S-TuD-141/200c (1 mg/kg) from the tail vein reduced tumor growth. Therefore, it is suggested that use of lipid nanoparticles used in this Example delivers the miRNA inhibiting complex used herein advantageously to a target site of tumor, whereby tumor can be treated and prevented.

Example 3: Suppression of Tumor with Improved S-TuD Against Non-Small Cell Lung Cancer Lung cancer cells were transplanted and analyzed to confirm that suppression of tumor in vivo by inhibition of the miR-200 family observed in breast cancer cell strains is also induced in cancer cells from other organs.

<Materials and Methods>

Cell Culture

Non-small cell lung cancer cell strains H596, A-427, and HCC827 were obtained from ATCC. H596 cells were cultured in DMEM comprising 10% fetal bovine serum (FBS) at 37° C. A-427 cells are cultured in EMEM comprising 10% fetal bovine serum (FBS) at 37° C. HCC827 cells were cultured in RPMI 1640 comprising 10% fetal bovine serum (FBS) at 37° C.

Animal Experiment

Female BALB/c nude mice were purchased from Japan SLC. All experiments use 6 week old mice. H596 cells transduced with a virus were suspended in a DMEM medium, and equal amount of Matrigel (BD) is mixed and injected into the right flank. The tumor volume was measured with a digital caliper.

miRNA Inhibiting Complex

The miRNA inhibiting complex (S-TuD-141/200c-1_17-pf-S10-BT6-MBSB1) is prepared in the same manner as Example 1.

The prepared miRNA inhibiting complex is administered intravenously to the tail vein or intratumorally to mice transplanted with tumor to study the reduction in tumor.

Example 4: Suppression of Tumor In Vivo with Improved S-TuD Using DDS

This Example studied the drug delivery system (DDS) suitable for delivery of the improved S-TuD of the invention.

<Materials and Methods>

Preparation of an animal tumor model, miRNA inhibiting complex, and the like was the same as Example 1, except for using a drug delivery system.

Lipid nanoparticles with the following components were used as the DDS.

COATSOME SS-33/1PZ-21

[Chemical Formula 44]

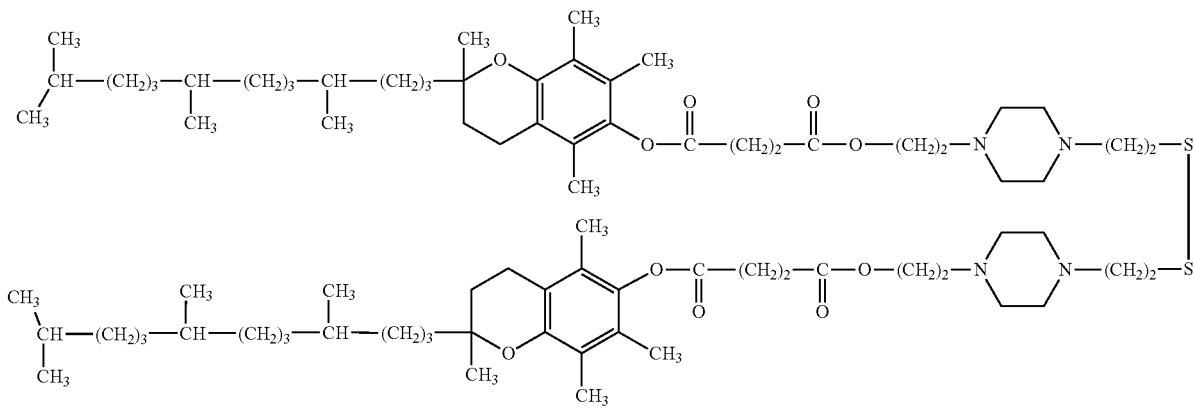

[Chemical Formula 45]    Cholesterol

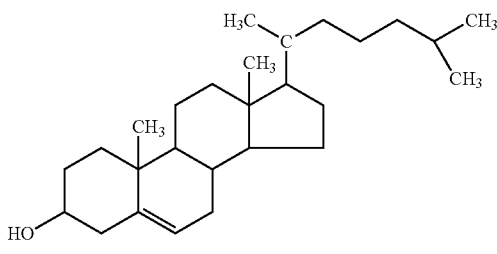

DSG-PEG5k

[Chemical Formula 46]

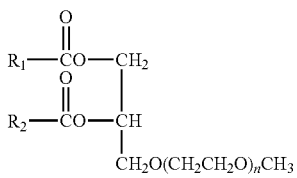

wherein $R_1$ and $R_2$ are C18:0 acyl.

Composition of LNP

Lipid nanoparticles with the following component ratio were prepared and used for in vivo study.

Formulation:

| Lipid | 3240 nmol |
|---|---|
| S-TuD | 1.67 nmol |
| Lipid/S-TuD ratio | 1940 |
| Recovery rate (%) | 91 |
| Encapsulation rate (%) | 81 |
| Diameter (d. nm) | 108 |

The ratio of each component for mice was

| S-TuD | 3 mg/kg |
|---|---|
| COATSOME SS-33/1PZ-21 | 2585 nmol/mouse |

-continued

| | |
|---|---|
| Cholesterol | 1108 nmol/mouse |
| DSG-PEG5k | 295 nmol/mouse. |

With the date of transplantation of tumor cells being day 0, S-TuD-141/200c-1_17-pf-S10-BT6-MBSB1 (LNP-S-TuD-141/200c) (3 mg/kg) encapsulated in the LNP or S-TuD-NCs-S10-BT6-MBSB1 (LNP-S-TuD negative control) (3 mg/kg) encapsulated in the LNP was injected from the tail vein on days 57, 64, 71, 76, 85, 92, 99, and 104 into mice, which were transplanted with 5×10$^5$ SUM149PT cells in mammary fat pad in the same manner as Example 1.

<Results>

Figure 11:
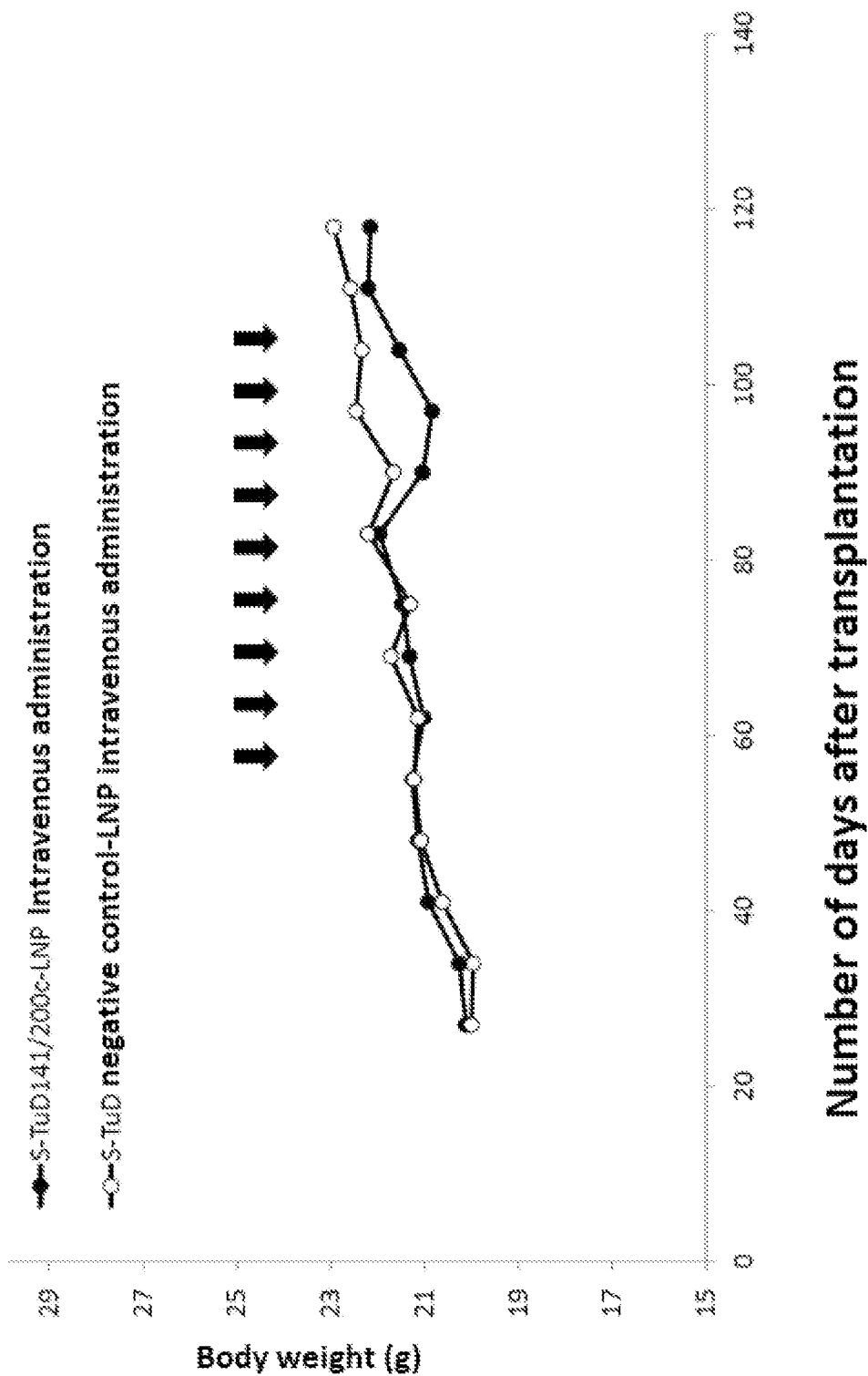
FIG. 11 is a diagram showing the change in the body weight (g) over time of tumor transplanted mice injected with S-TuD-141/200c-1_17-pf-S10-BT6-MBSB1 (LNP-S-TuD-141/200c) or S-TuD-NCs-S10-BT6-MBSB1 (LNP-S-TuD negative control) encapsulated in lipid nanoparticles intravenously to the tail. The arrows indicate the timing of administration.
Figure 12:
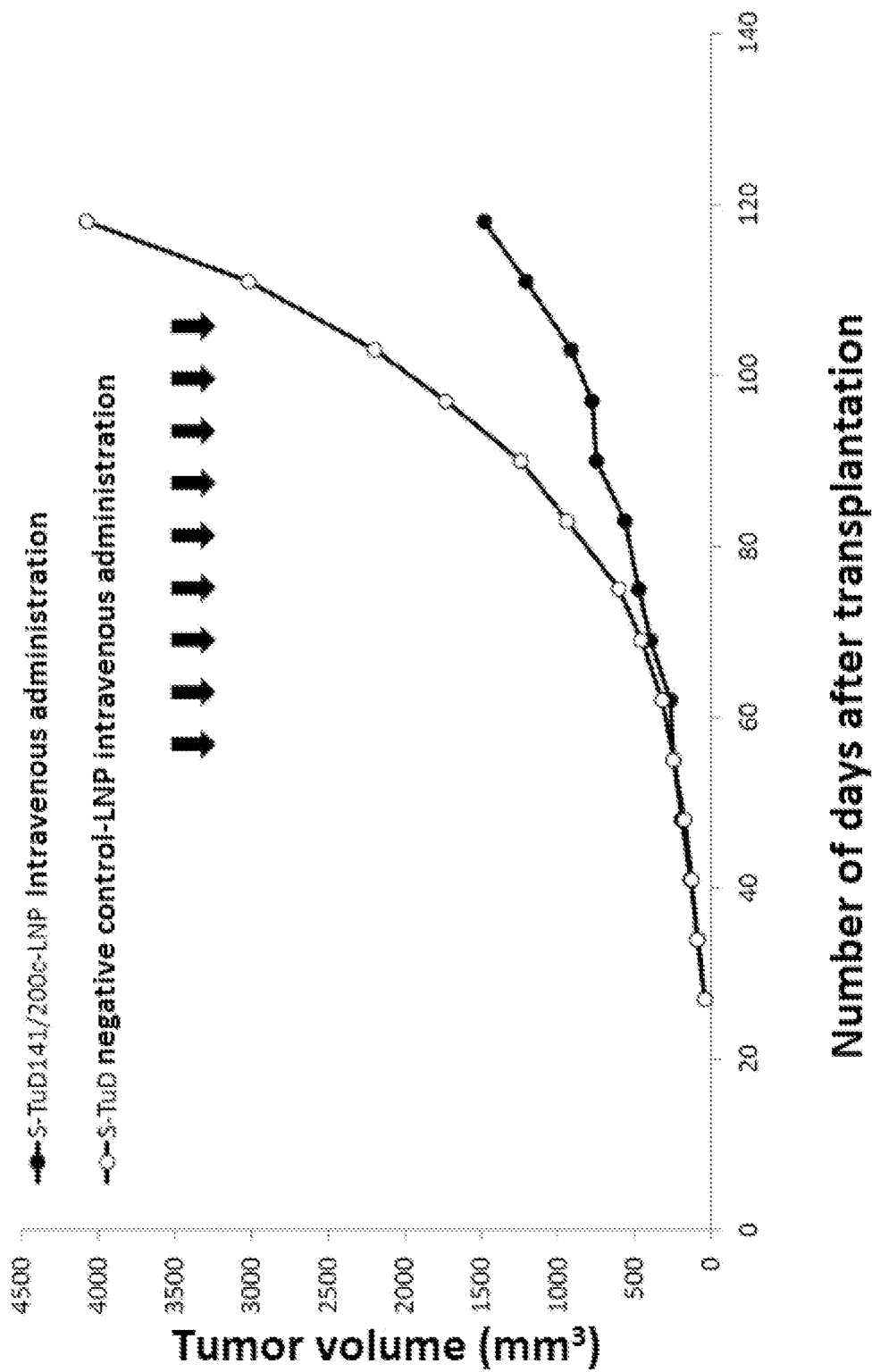
FIG. 12 is a diagram showing the change in the tumor volume (mm$^3$) over time of tumor transplanted mice injected with S-TuD-141/200c-1_17-pf-S10-BT6-MBSB1 (LNP-S-TuD-141/200c) or S-TuD-NCs-S10-BT6-MBSB1 (LNP-S-TuD negative control) encapsulated in lipid nanoparticles intravenously to the tail. The arrows indicate the timing of administration.

The results are shown in FIGS. 11 and 12. As shown in FIG. 11, there was no significant change in the body weight of mice administered with LNP-S-TuD-141/200c (3 mg/kg) or LNP-S-TuD negative control (3 mg/kg), and side effects were not observed, suggesting that the LNP can be safely used.

As shown in FIG. 12, administration of LNP-S-TuD-141/200c (3 mg/kg) from the tail vein reduced tumor growth compared to administration of LNP-S-TuD negative control (3 mg/kg) from the tail vein. Therefore, it is suggested that use of lipid nanoparticles used in this Example delivers the miRNA inhibiting complex used herein advantageously to a target site of tumor, whereby tumor can be treated and prevented.

Example 5: Suppression of miR-21 in Lung Cancer Cell Strain H358 with Improved S-TuD (Luciferase Assay)

H358 cells were spread on a 24-well plate on the day before introduction at 1.0×105 cells per well in RPMI 1640 comprising 10% foetal bovine serum (FBS), and were transfected in triplicate using Lipofectamine 2000 (Life Technologies) and 100 ng of reporter plasmid (psiCHECK2-UT or psiCHECK2-T21-5p) (see FIGS. 13, 14, and 15) and various S-TuDs. All assays were conducted using GLO-MAX™ (Promega) with dual luciferase assay (Promega) after 48 hours from transfection.

The protocol of the miR-21 inhibition assay using an improved S-TuD is the following.

The activity of a target miRNA was measured by measuring the ratio of *renilla* luciferase (RL) and firefly luciferase (FL) in the following Experiments 1 and 2.

(Experiment 1)

Lung cancer cell strain H358 cells endogenously expressing miR-21 were cultured in RPMI 1640 comprising 10% foetal bovine serum (FBS) at 37° C.

(Experiment 2)

Figure 13:
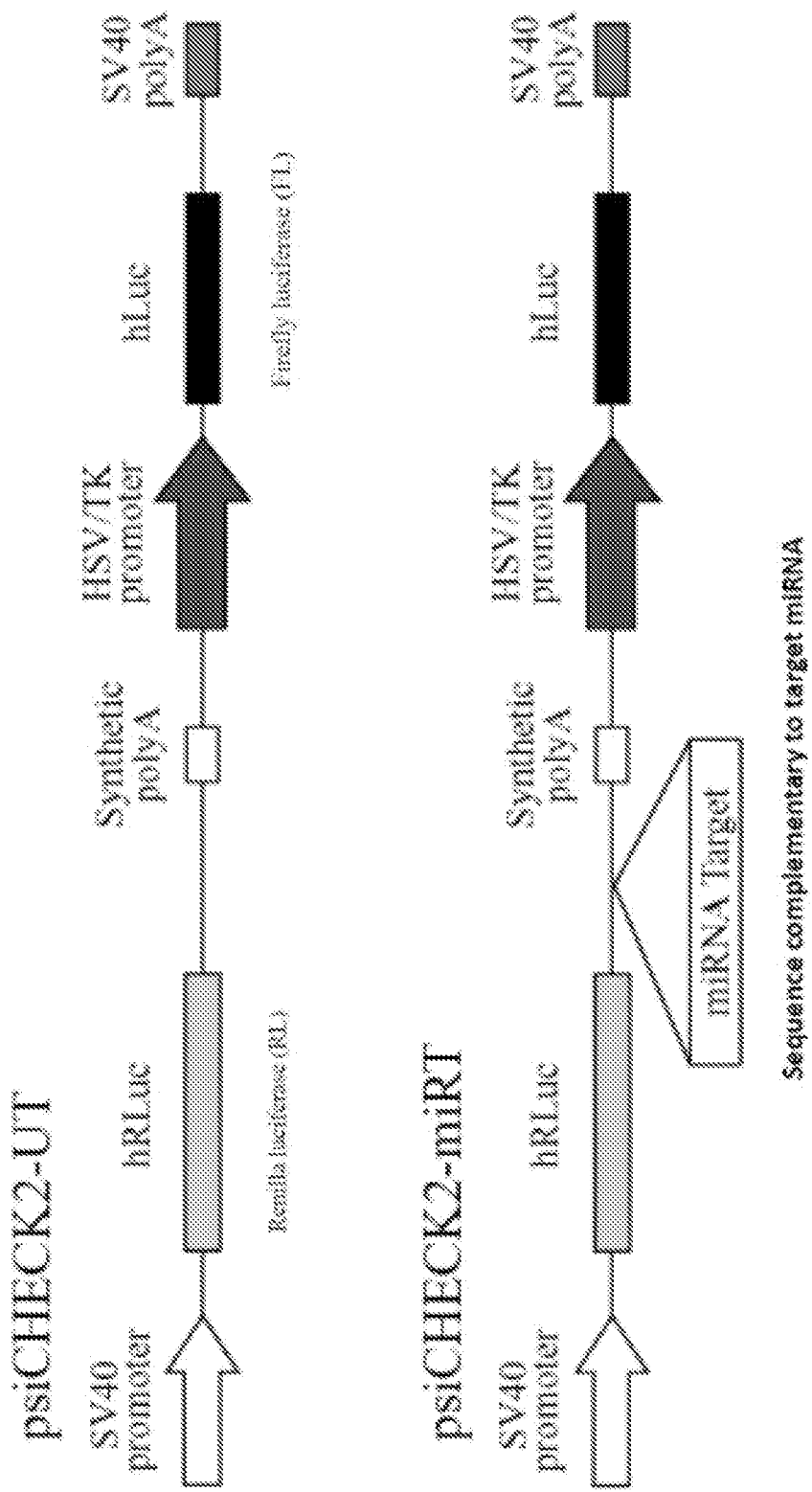
FIG. 13 depicts the structures of psiCHECK2-UT (top) and psiCHECK2-miRT (bottom).
Figure 14:
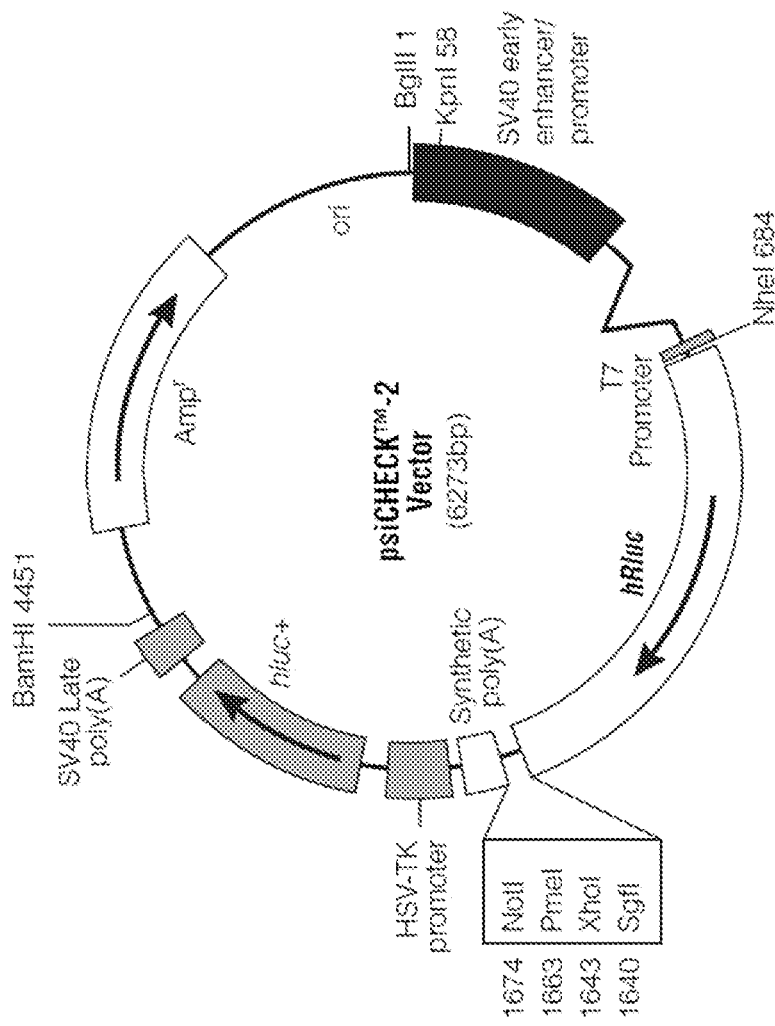
FIG. 14 depicts a schematic diagram of the luciferase reporter vector used in the Examples.
Figures 2, 16:
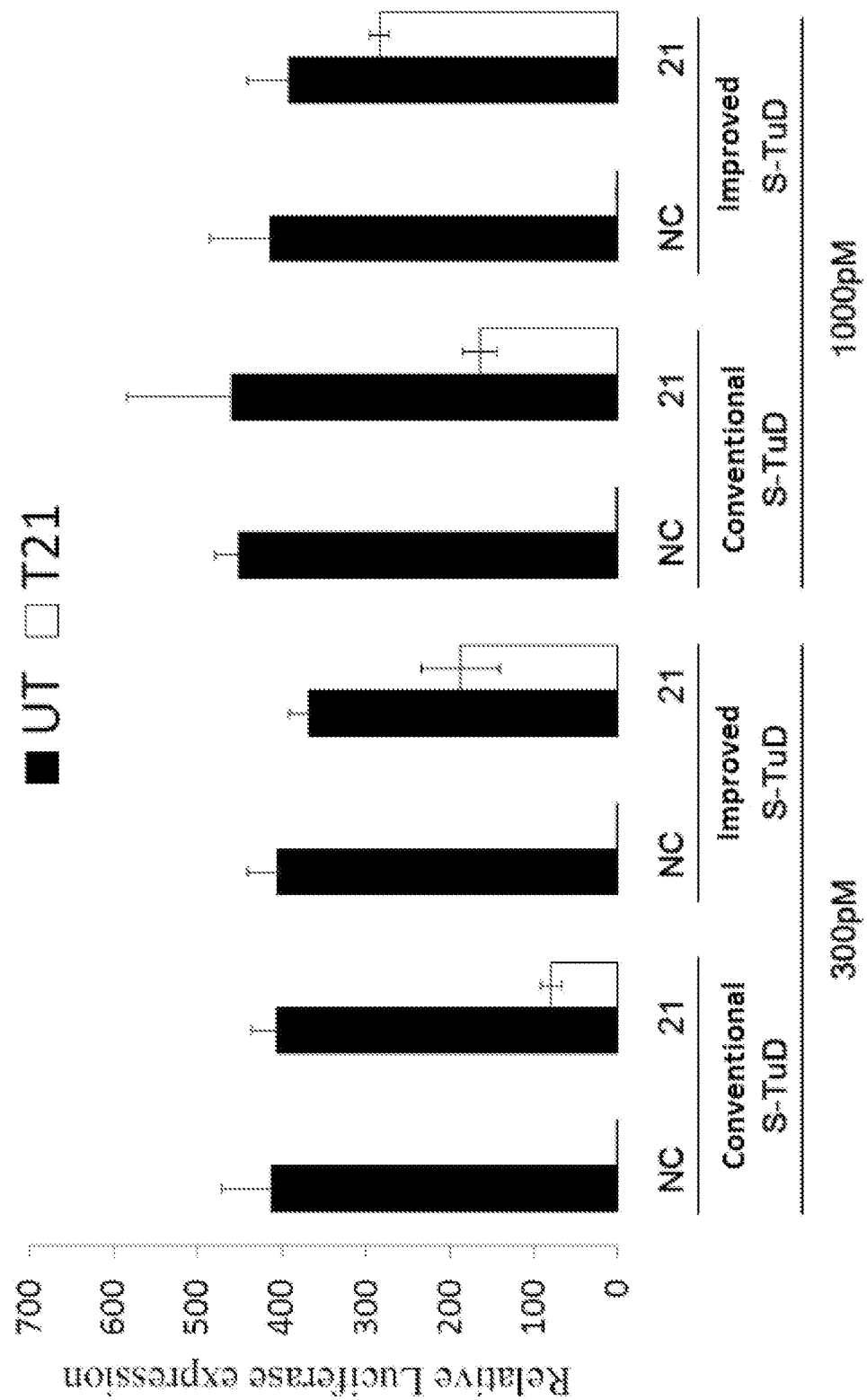

H358 cells were transfected with psiCHECK2-T21-5p (PROMEGA, prepared by inserting, for example, a sequence complementary to a target miRNA such as miR-21 into the XhoI-NotI site; the entire structure is shown in FIG. 13) and a synthetic modified S-TuD as shown in FIG. 16-1. Chemiluminescent signals generated by *renilla* luciferase (RL) and firefly luciferase (FL) expressed by transfected cells reacting with their respective specific substrate were then measured by a luminometer, and the ratio of *renilla* luciferase (RL) to firefly luciferase (FL) was obtained for the measured signals. The results are shown in FIG. 16-2. The results in FIG. 16-2 show that the improved S-TuD-21 completely inhibits miR-21 activity of H358 cells at a low concentration of 1000 pM, and has higher inhibitory activity compared to conventional S-TuD.

Example 6: Suppression of miR-200c in Lung Cancer Cell Strain H358 with Improved S-TuD (Luciferase Assay)

H358 cells were spread on a 24-well plate on the day before introduction at 1.0×10$^5$ cells per well in RPMI 1640 comprising 10% foetal bovine serum (FBS), and were transfected in triplicate using Lipofectamine 2000 (Life Technologies) and 100 ng of reporter plasmid (psiCHECK2-UT or psiCHECK2-T200c-3p) (see FIGS. 13, 14, and 15) and various S-TuDs. All assays were conducted using GLO-MAX™ (Promega) with dual luciferase assay (Promega) after 48 hours from transfection.

The protocol of the miR-200c inhibition assay using an improved S-TuD (sense sequence: SEQ ID NO: 26 and antisense sequence: SEQ ID NO: 27) is the following.

The activity of a target miRNA was measured by measuring the ratio of *renilla* luciferase (RL) and firefly luciferase (FL) in the following Experiments 5 and 6.

(Experiment 5)

Lung cancer cell strain H358 cells endogenously expressing miR-200c were cultured in RPMI 1640 comprising 10% foetal bovine serum (FBS) at 37° C.

(Experiment 6)

Figures 3, 17:
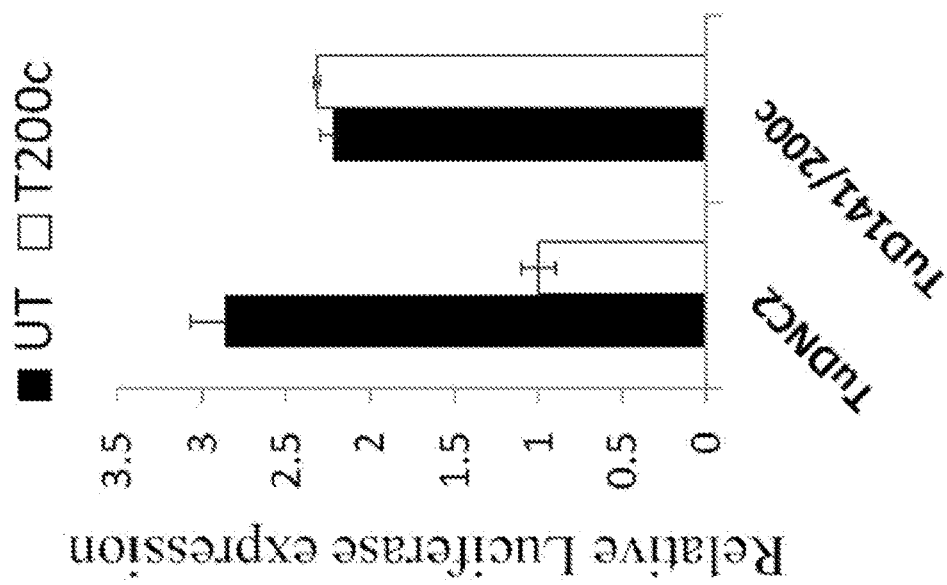
Figures 2, 17:
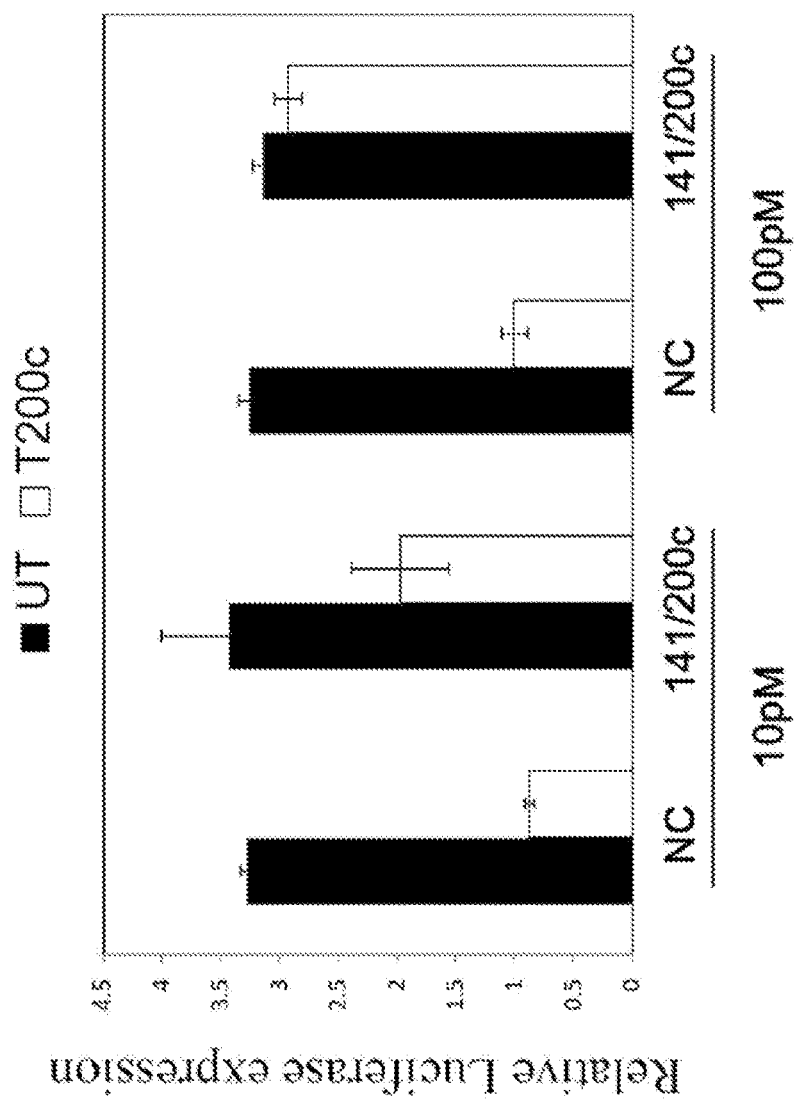

H358 cells were transfected with psiCHECK2-T200c-3p and a synthetic modified S-TuD as shown in FIG. 17-1. Chemiluminescent signals generated by *renilla* luciferase (RL) and firefly luciferase (FL) expressed by transfected cells reacting with their respective specific substrate were then measured by a luminometer, and the ratio of *renilla* luciferase (RL) to firefly luciferase (FL) was obtained for the measured signals. The results are shown in FIG. 17-2. The results in FIG. 17-2 show that the improved S-TuD-141/200c completely inhibits miR-200c activity of H358 cells at a low concentration of 100 pM.

The protocol of the miR-200c inhibition assay using a TuD expression lentiviral vector is the following.

The activity of a target miRNA was measured by measuring the ratio of *renilla* luciferase (RL) and firefly luciferase (FL) in the following Experiments 7 and 8.

(Experiment 7)

Lung cancer cell strain H358 cells endogenously expressing miR-200c were cultured in RPMI 1640 comprising 10% foetal bovine serum (FBS) at 37° C. H358 cells were spread on a 6-well plate at 1×105 cells per well. After 24 hours, a pLSP-TuD-141/200c viral vector (3×105 TU) was transduced in the presence of 8 μg/ml polybrene. After 24 hours from transduction, the cells were selected using Puromycin (1 ug/ml). After 1 week of selection, Puromycin was removed from the medium to obtain H358-TuD-141/200c cells retaining a TuD-141/200c expression cassette.

(Experiment 8)

psiCHECK2-T200c-3 cells were transfected into H358-TuD-141/200c cells. Chemiluminescent signals generated by *renilla* luciferase (RL) and firefly luciferase (FL) expressed by transfected cells reacting with their respective specific substrate were then measured by a luminometer, and the ratio of *renilla* luciferase (RL) to firefly luciferase (FL) was obtained for the measured signals. The results are shown in FIG. 17-3. The results in FIG. 17-3 showed that TuD-141/200c expressed from the transduced lentiviral vector completely inhibits miR-200c activity of H358 cells.

The present invention has been described based on the Examples. It is understood by those skilled in the art that these embodiments are exemplifications so that various modified examples are possible and such modified examples are also within the scope of the present invention.

As described above, the present invention is exemplified by the use of preferred embodiments of the invention. However, it is understood that the scope of the invention should be interpreted solely based on the Claims. It is also understood that any patent, patent application, and reference cited herein should be incorporated herein by reference in the same manner as the contents are specifically described. In particular, PCT/JP2016/078345, PCT/JP2016/004252, and Japanese Patent Application No. 2013-544251 can be referenced herein. The entire content thereof is incorporated herein by reference. The present application claims priority to Japanese Patent Application No. 2017-53124. The entire content thereof is incorporated herein by reference.

INDUSTRIAL APPLICABILITY

The present invention is useful in the drug development industry and reagent industry using nucleic acid medicaments and the like.

[Sequence Listing Free Text]
SEQ ID NO: 1: binding sequence for miR-141 of S-TuD-141/200c-1_17-pf-S10-BT6-MBSB1
SEQ ID NO: 2: binding sequence for miR-200c of S-TuD-141/200c-1_17-pf-S10-BT6-MBSB1
SEQ ID NO: 3: binding sequence for miR-141 of S-TuD-141/200c-1_17-pf-S10-BT6-MBSB1 (including BNA at a specific position)
SEQ ID NO: 4: binding sequence for miR-200c of S-TuD-141/200c-1_17-pf-S10-BT6-MBSB1 (including BNA at a specific position)
SEQ ID NO: 5: S-TuD-141/200c-1_17-pf-S10 sense sequence
SEQ ID NO: 6: S-TuD-141/200c-1_17-pf-S10 antisense sequence
SEQ ID NO: 7: S-TuD-NCs-S10 sense sequence
SEQ ID NO: 8: S-TuD-NCs-S10 antisense sequence
SEQ ID NO: 9: S-TuD-141/200c-1_17-pf-S10-BT6-MBSB1 sense sequence (including BNA at a specific position)
SEQ ID NO: 10: S-TuD-141/200c-1_17-pf-S10-BT6-MBSB1 antisense sequence (including BNA at a specific position)
SEQ ID NO: 11: S-TuD-NCs-S10-BT6-MBSB1 sense sequence (including BNA at a specific position)
SEQ ID NO: 12: S-TuD-NCs-S10-BT6-MBSB1 antisense sequence (including BNA at a specific position)
SEQ ID NO: 13: miR-200a
SEQ ID NO: 14: miR-141
SEQ ID NO: 15: miR-200b
SEQ ID NO: 16: miR-200c
SEQ ID NO: 17: miR-429
SEQ ID NO: 18: Sense sequence of FIG. 10 (41)
SEQ ID NO: 19: Antisense sequence of FIG. 10 (41)
SEQ ID NO: 20: Sense sequence of FIG. 10 (42)
SEQ ID NO: 21: Antisense sequence of FIG. 10 (42)
SEQ ID NO: 22: Sense sequence of FIG. 10 (43)
SEQ ID NO: 23: Antisense sequence of FIG. 10 (43)
SEQ ID NO: 24: Sense sequence of FIG. 10 (44)
SEQ ID NO: 25: Antisense sequence of FIG. 10 (44)
SEQ ID NO: 26: Sense sequence of FIG. 10 (45)
SEQ ID NO: 27: Antisense sequence of FIG. 10 (45)
SEQ ID NO: 28: psiCHECK2-T21-5p-s of FIG. 15
SEQ ID NO: 29: psiCHECK2-T21-5p-a of FIG. 15
SEQ ID NO: 30: psiCHECK2-T200c-3p-s of FIG. 15
SEQ ID NO: 31: psiCHECK2-T200c-3p-a of FIG. 15
SEQ ID NO: 32: Binding sequence for miR-21 of conventional S-TuD-21
SEQ ID NO: 33: Binding sequence for miR-21 of improved S-TuD-21
SEQ ID NO: 34: Binding sequence for miR-21 of improved S-TuD-21 (including BNA at a specific position)
SEQ ID NO: 35: Conventional S-TuD-21 sense sequence
SEQ ID NO: 36: Conventional S-TuD-21 antisense sequence
SEQ ID NO: 37: Improved S-TuD-21 sense sequence
SEQ ID NO: 38: Improved S-TuD-21 antisense sequence
SEQ ID NO: 39: Improved S-TuD-21 sense sequence (including BNA at a specific position)
SEQ ID NO: 40: Improved S-TuD-21 antisense sequence (including BNA at a specific position)
SEQ ID NO: 41: miR-21.

The invention claimed is:

1. A nucleic acid molecule comprising:
   (a) two miRNA binding sequences, one of the miRNA binding sequences comprising 5'-CAGUGUU-3' wherein each U is either a uracil base or a thymine base, and the other miRNA binding sequence comprising 5'-CAGUAUU-3' wherein each U is either a uracil base or a thymine base; and at least one bridged nucleic acid (BNA), or
   (b) an miRNA binding sequence comprising the sequence of SEQ ID NO: 1 wherein each U is either a uracil base or a thymine base; an miRNA binding sequence comprising the sequence of SEQ ID NO: 2; and at least one bridged nucleic acid (BNA), or
   (c) the sequence of SEQ ID NO: 9 wherein each U is either a uracil base or a thymine base; and the sequence of SEQ ID NO: 10 wherein each U is either a uracil base or a thymine base, or
   (d) the sequence of 5'-AUAAGCU-3' wherein each U is either a uracil base or a thymine base; and at least one bridged nucleic acid (BNA).

* * * * *

SEQUENCE LISTING

```
<160> NUMBER OF SEQ ID NOS: 42

<210> SEQ ID NO 1
<211> LENGTH: 17
<212> TYPE: DNA
<213> ORGANISM: artificial sequence
<220> FEATURE:
<223> OTHER INFORMATION: S-TuD-141/200c-1_17-pf-S10-BT6-MBSB1 MBS
      miR-141

<400> SEQUENCE: 1
uuuaccagac aguguua                                                 17

<210> SEQ ID NO 2
<211> LENGTH: 17
<212> TYPE: DNA
<213> ORGANISM: artificial sequence
<220> FEATURE:
<223> OTHER INFORMATION: S-TuD-141/200c-1_17-pf-S10-BT6-MBSB1 MBS
      miR-200c

<400> SEQUENCE: 2
```

```
auuacccggc aguauua                                                      17

<210> SEQ ID NO 3
<211> LENGTH: 17
<212> TYPE: DNA
<213> ORGANISM: artificial sequence
<220> FEATURE:
<223> OTHER INFORMATION: S-TuD-141/200c-1_17-pf-S10-BT6-MBSB1 MBS
      miR-141 (BNA)
<220> FEATURE:
<221> NAME/KEY: BNANC(NMe)
<222> LOCATION: (2)..(2)
<220> FEATURE:
<221> NAME/KEY: BNANC(NMe)
<222> LOCATION: (5)..(5)

<400> SEQUENCE: 3
utuaccagac aguguua                                                      17

<210> SEQ ID NO 4
<211> LENGTH: 17
<212> TYPE: DNA
<213> ORGANISM: artificial sequence
<220> FEATURE:
<223> OTHER INFORMATION: S-TuD-141/200c-1_17-pf-S10-BT6-MBSB1 MBS
      miR-200c (BNA)
<220> FEATURE:
<221> NAME/KEY: BNANC(NMe)
<222> LOCATION: (2)..(2)
<220> FEATURE:
<221> NAME/KEY: BNANC(NMe)
<222> LOCATION: (5)..(5)

<400> SEQUENCE: 4
atuacccggc aguauua                                                      17

<210> SEQ ID NO 5
<211> LENGTH: 43
<212> TYPE: DNA
<213> ORGANISM: artificial sequence
<220> FEATURE:
<223> OTHER INFORMATION: S-TuD-141/200c-1_17-pf-S10 Sense

<400> SEQUENCE: 5
uaggaucauc agauuuacca gacaguguua agaguauucu ggu                         43

<210> SEQ ID NO 6
<211> LENGTH: 43
<212> TYPE: DNA
<213> ORGANISM: artificial sequence
<220> FEATURE:
<223> OTHER INFORMATION: S-TuD-141/200c-1_17-pf-S10 Antisense

<400> SEQUENCE: 6
accagaauac agaauuaccc ggcaguauua agagaugauc cua                         43

<210> SEQ ID NO 7
<211> LENGTH: 43
<212> TYPE: DNA
<213> ORGANISM: artificial sequence
<220> FEATURE:
<223> OTHER INFORMATION: S-TuD-NCs-S10 Sense

<400> SEQUENCE: 7
uaggaucauc aacguaucga cgucgaggcc caaguauucu ggu                         43

<210> SEQ ID NO 8
<211> LENGTH: 43
```

```
<212> TYPE: DNA
<213> ORGANISM: artificial sequence
<220> FEATURE:
<223> OTHER INFORMATION: S-TuD-NCs-S10 Antisense

<400> SEQUENCE: 8
accagaauac aacguaucga cgucgaggcc caagaugauc cua            43

<210> SEQ ID NO 9
<211> LENGTH: 43
<212> TYPE: DNA
<213> ORGANISM: artificial sequence
<220> FEATURE:
<223> OTHER INFORMATION: S-TuD-141/200c-1_17-pf-S10-BT6-MBSB1 Sense
      (BNA)
<220> FEATURE:
<221> NAME/KEY: BNANC(NMe)
<222> LOCATION: (1)..(1)
<220> FEATURE:
<221> NAME/KEY: BNANC(NMe)
<222> LOCATION: (15)..(15)
<220> FEATURE:
<221> NAME/KEY: BNANC(NMe)
<222> LOCATION: (18)..(18)
<220> FEATURE:
<221> NAME/KEY: BNANC(NMe)
<222> LOCATION: (38)..(38)
<220> FEATURE:
<221> NAME/KEY: BNANC(NMe)
<222> LOCATION: (43)..(43)

<400> SEQUENCE: 9
taggaucauc agauuuacca gacaguguua agaguautcu ggt            43

<210> SEQ ID NO 10
<211> LENGTH: 43
<212> TYPE: DNA
<213> ORGANISM: artificial sequence
<220> FEATURE:
<223> OTHER INFORMATION: S-TuD-141/200c-1_17-pf-S10-BT6-MBSB1 Antisense
      (BNA)
<220> FEATURE:
<221> NAME/KEY: BNANC(NMe)
<222> LOCATION: (8)..(8)
<220> FEATURE:
<221> NAME/KEY: BNANC(NMe)
<222> LOCATION: (15)..(15)
<220> FEATURE:
<221> NAME/KEY: BNANC(NMe)
<222> LOCATION: (18)..(18)
<220> FEATURE:
<221> NAME/KEY: BNANC(NMe)
<222> LOCATION: (36)..(36)
<220> FEATURE:
<221> NAME/KEY: BNANC(NMe)
<222> LOCATION: (39)..(39)

<400> SEQUENCE: 10
accagaatac agaatuaccc ggcaguauua agagatgatc cua            43

<210> SEQ ID NO 11
<211> LENGTH: 43
<212> TYPE: DNA
<213> ORGANISM: artificial sequence
<220> FEATURE:
<223> OTHER INFORMATION: S-TuD-NCs-S10-BT6-MBSB1 Sense (BNA)
<220> FEATURE:
<221> NAME/KEY: BNANC(NMe)
<222> LOCATION: (1)..(1)
<220> FEATURE:
<221> NAME/KEY: BNANC(NMe)
<222> LOCATION: (15)..(15)
<220> FEATURE:
```

```
<221> NAME/KEY: BNANC(NMe)
<222> LOCATION: (18)..(18)
<220> FEATURE:
<221> NAME/KEY: BNANC(NMe)
<222> LOCATION: (38)..(38)
<220> FEATURE:
<221> NAME/KEY: BNANC(NMe)
<222> LOCATION: (43)..(43)

<400> SEQUENCE: 11
taggaucauc aacguaucga cgucgaggcc caaguaucu ggt                 43

<210> SEQ ID NO 12
<211> LENGTH: 43
<212> TYPE: DNA
<213> ORGANISM: artificial sequence
<220> FEATURE:
<223> OTHER INFORMATION: S-TuD-NCs-S10-BT6-MBSB1 Antisense (BNA)
<220> FEATURE:
<221> NAME/KEY: BNANC(NMe)
<222> LOCATION: (8)..(8)
<220> FEATURE:
<221> NAME/KEY: BNANC(NMe)
<222> LOCATION: (15)..(15)
<220> FEATURE:
<221> NAME/KEY: BNANC(NMe)
<222> LOCATION: (18)..(18)
<220> FEATURE:
<221> NAME/KEY: BNANC(NMe)
<222> LOCATION: (36)..(36)
<220> FEATURE:
<221> NAME/KEY: BNANC(NMe)
<222> LOCATION: (39)..(39)

<400> SEQUENCE: 12
accagaauac aacguaucga cgucgaggcc caagaugauc cua               43

<210> SEQ ID NO 13
<211> LENGTH: 22
<212> TYPE: DNA
<213> ORGANISM: Homo sapiens

<400> SEQUENCE: 13
uaacacuguc ugguaacgau gu                                       22

<210> SEQ ID NO 14
<211> LENGTH: 22
<212> TYPE: DNA
<213> ORGANISM: Homo sapiens

<400> SEQUENCE: 14
uaacacuguc ugguaaagau gg                                       22

<210> SEQ ID NO 15
<211> LENGTH: 22
<212> TYPE: DNA
<213> ORGANISM: Homo sapiens

<400> SEQUENCE: 15
uaauacugcc ugguaaugau ga                                       22

<210> SEQ ID NO 16
<211> LENGTH: 23
<212> TYPE: DNA
<213> ORGANISM: Homo sapiens

<400> SEQUENCE: 16
uaauacugcc ggguaaugau gga                                      23
```

<210> SEQ ID NO 17
<211> LENGTH: 22
<212> TYPE: DNA
<213> ORGANISM: Homo sapiens

<400> SEQUENCE: 17
uaauacuguc ugguaaaacc gu                                              22

<210> SEQ ID NO 18
<211> LENGTH: 56
<212> TYPE: DNA
<213> ORGANISM: artificial sequence
<220> FEATURE:
<223> OTHER INFORMATION: sense sequence (41)
<220> FEATURE:
<221> NAME/KEY: 2'-OMe
<222> LOCATION: (1)..(56)

<400> SEQUENCE: 18
uacggcgcua ggaucaucaa cccaucauua cccggcagua uuacaaguau ucugga         56

<210> SEQ ID NO 19
<211> LENGTH: 56
<212> TYPE: DNA
<213> ORGANISM: artificial sequence
<220> FEATURE:
<223> OTHER INFORMATION: antisense sequence (41)
<220> FEATURE:
<221> NAME/KEY: 2'-OMe
<222> LOCATION: (1)..(56)

<400> SEQUENCE: 19
uccagaauac aacccaucau uacccggcag uauuacaaga ugauccuagc gccgua         56

<210> SEQ ID NO 20
<211> LENGTH: 56
<212> TYPE: DNA
<213> ORGANISM: artificial sequence
<220> FEATURE:
<223> OTHER INFORMATION: sense sequence (42)
<220> FEATURE:
<221> NAME/KEY: BNANC(NMe)
<222> LOCATION: (1)..(1)
<220> FEATURE:
<221> NAME/KEY: 2'-OMe
<222> LOCATION: (2)..(47)
<220> FEATURE:
<221> NAME/KEY: BNANC(NMe)
<222> LOCATION: (48)..(48)
<220> FEATURE:
<221> NAME/KEY: 2'-OMe
<222> LOCATION: (49)..(52)
<220> FEATURE:
<221> NAME/KEY: BNANC(NMe)
<222> LOCATION: (53)..(53)
<220> FEATURE:
<221> NAME/KEY: 2'-OMe
<222> LOCATION: (54)..(56)

<400> SEQUENCE: 20
tacggcgcua ggaucaucaa cccaucauua cccggcagua uuacaagtau uctgga         56

<210> SEQ ID NO 21
<211> LENGTH: 56
<212> TYPE: DNA
<213> ORGANISM: artificial sequence
<220> FEATURE:
<223> OTHER INFORMATION: antisense sequence (42)
<220> FEATURE:

```
<221> NAME/KEY: BNANC(NMe)
<222> LOCATION: (1)..(1)
<220> FEATURE:
<221> NAME/KEY: 2'-OMe
<222> LOCATION: (2)..(40)
<220> FEATURE:
<221> NAME/KEY: BNANC(NMe)
<222> LOCATION: (41)..(41)
<220> FEATURE:
<221> NAME/KEY: 2'-OMe
<222> LOCATION: (42)..(46)
<220> FEATURE:
<221> NAME/KEY: BNANC(NMe)
<222> LOCATION: (47)..(47)
<220> FEATURE:
<221> NAME/KEY: 2'-OMe
<222> LOCATION: (48)..(56)

<400> SEQUENCE: 21
tccagaauac aacccaucau uacccggcag uauuacaaga tgaucctagc gccgua         56

<210> SEQ ID NO 22
<211> LENGTH: 56
<212> TYPE: DNA
<213> ORGANISM: artificial sequence
<220> FEATURE:
<223> OTHER INFORMATION: sense sequence (43)
<220> FEATURE:
<221> NAME/KEY: BNANC(NMe)
<222> LOCATION: (1)..(1)
<220> FEATURE:
<221> NAME/KEY: 2'-OMe
<222> LOCATION: (2)..(38)
<220> FEATURE:
<221> NAME/KEY: BNANC(NMe)
<222> LOCATION: (39)..(39)
<220> FEATURE:
<221> NAME/KEY: 2'-OMe
<222> LOCATION: (40)..(41)
<220> FEATURE:
<221> NAME/KEY: BNANC(NMe)
<222> LOCATION: (42)..(42)
<220> FEATURE:
<221> NAME/KEY: 2'-OMe
<222> LOCATION: (43)..(47)
<220> FEATURE:
<221> NAME/KEY: BNANC(NMe)
<222> LOCATION: (48)..(48)
<220> FEATURE:
<221> NAME/KEY: 2'-OMe
<222> LOCATION: (49)..(52)
<220> FEATURE:
<221> NAME/KEY: BNANC(NMe)
<222> LOCATION: (53)..(53)
<220> FEATURE:
<221> NAME/KEY: 2'-OMe
<222> LOCATION: (54)..(56)

<400> SEQUENCE: 22
tacggcgcua ggaucaucaa cccaucauua cccggcagta utacaagtau uctgga         56

<210> SEQ ID NO 23
<211> LENGTH: 56
<212> TYPE: DNA
<213> ORGANISM: artificial sequence
<220> FEATURE:
<223> OTHER INFORMATION: antisense sequence (43)
<220> FEATURE:
<221> NAME/KEY: BNANC(NMe)
<222> LOCATION: (1)..(1)
<220> FEATURE:
<221> NAME/KEY: 2'-OMe
<222> LOCATION: (2)..(30)
<220> FEATURE:
<221> NAME/KEY: BNANC(NMe)
```

```
<222> LOCATION: (31)..(31)
<220> FEATURE:
<221> NAME/KEY: 2'-OMe
<222> LOCATION: (32)..(33)
<220> FEATURE:
<221> NAME/KEY: BNANC(NMe)
<222> LOCATION: (34)..(34)
<220> FEATURE:
<221> NAME/KEY: 2'-OMe
<222> LOCATION: (35)..(40)
<220> FEATURE:
<221> NAME/KEY: BNANC(NMe)
<222> LOCATION: (41)..(41)
<220> FEATURE:
<221> NAME/KEY: 2'-OMe
<222> LOCATION: (42)..(46)
<220> FEATURE:
<221> NAME/KEY: BNANC(NMe)
<222> LOCATION: (47)..(47)
<220> FEATURE:
<221> NAME/KEY: 2'-OMe
<222> LOCATION: (48)..(56)

<400> SEQUENCE: 23
tccagaauac aacccaucau uacccggcag tautacaaga tgauccuagc gccgua          56

<210> SEQ ID NO 24
<211> LENGTH: 56
<212> TYPE: DNA
<213> ORGANISM: artificial sequence
<220> FEATURE:
<223> OTHER INFORMATION: sense sequence (44)
<220> FEATURE:
<221> NAME/KEY: BNANC(NMe)
<222> LOCATION: (1)..(1)
<220> FEATURE:
<221> NAME/KEY: 2'-OMe
<222> LOCATION: (2)..(27)
<220> FEATURE:
<221> NAME/KEY: BNANC(NMe)
<222> LOCATION: (28)..(28)
<220> FEATURE:
<221> NAME/KEY: 2'-OMe
<222> LOCATION: (29)..(30)
<220> FEATURE:
<221> NAME/KEY: BNANC(NMe)
<222> LOCATION: (31)..(31)
<220> FEATURE:
<221> NAME/KEY: 2'-OMe
<222> LOCATION: (32)..(47)
<220> FEATURE:
<221> NAME/KEY: BNANC(NMe)
<222> LOCATION: (48)..(48)
<220> FEATURE:
<221> NAME/KEY: 2'-OMe
<222> LOCATION: (49)..(52)
<220> FEATURE:
<221> NAME/KEY: BNANC(NMe)
<222> LOCATION: (53)..(53)
<220> FEATURE:
<221> NAME/KEY: 2'-OMe
<222> LOCATION: (54)..(56)

<400> SEQUENCE: 24
tacggcgcua ggaucaucaa cccaucatua cccggcagua uuacaagtau uctgga          56

<210> SEQ ID NO 25
<211> LENGTH: 56
<212> TYPE: DNA
<213> ORGANISM: artificial sequence
<220> FEATURE:
<223> OTHER INFORMATION: antisense sequence (44)
<220> FEATURE:
<221> NAME/KEY: BNANC(NMe)
<222> LOCATION: (1)..(1)
```

```
<220> FEATURE:
<221> NAME/KEY: 2'-OMe
<222> LOCATION: (2)..(19)
<220> FEATURE:
<221> NAME/KEY: BNANC(NMe)
<222> LOCATION: (20)..(20)
<220> FEATURE:
<221> NAME/KEY: 2'-OMe
<222> LOCATION: (21)..(22)
<220> FEATURE:
<221> NAME/KEY: BNANC(NMe)
<222> LOCATION: (23)..(23)
<220> FEATURE:
<221> NAME/KEY: 2'-OMe
<222> LOCATION: (24)..(40)
<220> FEATURE:
<221> NAME/KEY: BNANC(NMe)
<222> LOCATION: (41)..(41)
<220> FEATURE:
<221> NAME/KEY: 2'-OMe
<222> LOCATION: (42)..(46)
<220> FEATURE:
<221> NAME/KEY: BNANC(NMe)
<222> LOCATION: (47)..(47)
<220> FEATURE:
<221> NAME/KEY: 2'-OMe
<222> LOCATION: (48)..(56)

<400> SEQUENCE: 25
tccagaauac aacccaucat uacccggcag uauuacaaga tgauccuagc gccgua        56

<210> SEQ ID NO 26
<211> LENGTH: 48
<212> TYPE: DNA
<213> ORGANISM: artificial sequence
<220> FEATURE:
<223> OTHER INFORMATION: sense sequence (45)
<220> FEATURE:
<221> NAME/KEY: BNANC(NMe)
<222> LOCATION: (1)..(1)
<220> FEATURE:
<221> NAME/KEY: 2'-OMe
<222> LOCATION: (2)..(19)
<220> FEATURE:
<221> NAME/KEY: BNANC(NMe)
<222> LOCATION: (20)..(20)
<220> FEATURE:
<221> NAME/KEY: 2'-OMe
<222> LOCATION: (21)..(22)
<220> FEATURE:
<221> NAME/KEY: BNANC(NMe)
<222> LOCATION: (23)..(23)
<220> FEATURE:
<221> NAME/KEY: 2'-OMe
<222> LOCATION: (24)..(42)
<220> FEATURE:
<221> NAME/KEY: BNANC(NMe)
<222> LOCATION: (43)..(43)
<220> FEATURE:
<221> NAME/KEY: 2'-OMe
<222> LOCATION: (44)..(47)
<220> FEATURE:
<221> NAME/KEY: BNANC(NMe)
<222> LOCATION: (48)..(48)

<400> SEQUENCE: 26
taggaucauc aacccaucat uacccggcag uauuacaagu autcuggt        48

<210> SEQ ID NO 27
<211> LENGTH: 48
<212> TYPE: DNA
<213> ORGANISM: artificial sequence
<220> FEATURE:
<223> OTHER INFORMATION: antisense sequence (45)
<220> FEATURE:
```

```
<221> NAME/KEY: 2'-OMe
<222> LOCATION: (1)..(7)
<220> FEATURE:
<221> NAME/KEY: BNANC(NMe)
<222> LOCATION: (2)..(2)
<220> FEATURE:
<221> NAME/KEY: 2'-OMe
<222> LOCATION: (9)..(19)
<220> FEATURE:
<221> NAME/KEY: BNANC(NMe)
<222> LOCATION: (20)..(20)
<220> FEATURE:
<221> NAME/KEY: 2'-OMe
<222> LOCATION: (21)..(22)
<220> FEATURE:
<221> NAME/KEY: BNANC(NMe)
<222> LOCATION: (23)..(23)
<220> FEATURE:
<221> NAME/KEY: 2'-OMe
<222> LOCATION: (24)..(40)
<220> FEATURE:
<221> NAME/KEY: BNANC(NMe)
<222> LOCATION: (41)..(41)
<220> FEATURE:
<221> NAME/KEY: 2'-OMe
<222> LOCATION: (42)..(43)
<220> FEATURE:
<221> NAME/KEY: BNANC(NMe)
<222> LOCATION: (44)..(44)
<220> FEATURE:
<221> NAME/KEY: 2'-OMe
<222> LOCATION: (45)..(48)

<400> SEQUENCE: 27
accagaatac aacccaucat uacccggcag uauuacaaga tgatccua                48

<210> SEQ ID NO 28
<211> LENGTH: 29
<212> TYPE: DNA
<213> ORGANISM: artificial sequence
<220> FEATURE:
<223> OTHER INFORMATION: psiCHECK2-T21-5p-s

<400> SEQUENCE: 28
tcgagtcaac atcagtctga taagctagc                                     29

<210> SEQ ID NO 29
<211> LENGTH: 29
<212> TYPE: DNA
<213> ORGANISM: artificial sequence
<220> FEATURE:
<223> OTHER INFORMATION: psiCHECK2-T21-5p-a

<400> SEQUENCE: 29
ggccgctagc ttatcagact gatgttgac                                     29

<210> SEQ ID NO 30
<211> LENGTH: 30
<212> TYPE: DNA
<213> ORGANISM: artificial sequence
<220> FEATURE:
<223> OTHER INFORMATION: psiCHECK2-T200c-3p-s

<400> SEQUENCE: 30
tcgagtccat cattacccgg cagtattagc                                    30

<210> SEQ ID NO 31
<211> LENGTH: 30
<212> TYPE: DNA
<213> ORGANISM: artificial sequence
<220> FEATURE:
```

```
<223> OTHER INFORMATION: psiCHECK2-T200c-3p-a

<400> SEQUENCE: 31
ggccgctaat actgccgggt aatgatggac                                              30

<210> SEQ ID NO 32
<211> LENGTH: 17
<212> TYPE: DNA
<213> ORGANISM: artificial sequence
<220> FEATURE:
<223> OTHER INFORMATION: Conventional S-TuD-21 MBS miR-21

<400> SEQUENCE: 32
aucagucgga uaagcua                                                            17

<210> SEQ ID NO 33
<211> LENGTH: 17
<212> TYPE: DNA
<213> ORGANISM: artificial sequence
<220> FEATURE:
<223> OTHER INFORMATION: Improved S-TuD-21 MBS miR-21

<400> SEQUENCE: 33
atcagucgga uaagcua                                                            17

<210> SEQ ID NO 34
<211> LENGTH: 17
<212> TYPE: DNA
<213> ORGANISM: artificial sequence
<220> FEATURE:
<223> OTHER INFORMATION: Conventional S-TuD-21 MBS miR-21 (BNA)
<220> FEATURE:
<221> NAME/KEY: 2'-OMe
<222> LOCATION: (1)..(1)
<220> FEATURE:
<221> NAME/KEY: BNANC(NMe)
<222> LOCATION: (2)..(2)
<220> FEATURE:
<221> NAME/KEY: 2'-OMe
<222> LOCATION: (3)..(4)
<220> FEATURE:
<221> NAME/KEY: BNANC(NMe)
<222> LOCATION: (5)..(5)
<220> FEATURE:
<221> NAME/KEY: 2'-OMe
<222> LOCATION: (6)..(17)

<400> SEQUENCE: 34
atcagucgga uaagcua                                                            17

<210> SEQ ID NO 35
<211> LENGTH: 51
<212> TYPE: DNA
<213> ORGANISM: artificial sequence
<220> FEATURE:
<223> OTHER INFORMATION: Conventional S-TuD-21 Sense sequence

<400> SEQUENCE: 35
uacggcgcua ggaucaucaa caucagucgg auaagcuaca aguauucugg a                      51

<210> SEQ ID NO 36
<211> LENGTH: 51
<212> TYPE: DNA
<213> ORGANISM: artificial sequence
<220> FEATURE:
<223> OTHER INFORMATION: Conventional S-TuD-21 Antisense sequence

<400> SEQUENCE: 36
```
uccagaauac aacaucaguc ggauaagcua caagaugauc cuagcgccgu a    51

<210> SEQ ID NO 37
<211> LENGTH: 43
<212> TYPE: DNA
<213> ORGANISM: artificial sequence
<220> FEATURE:
<223> OTHER INFORMATION: Improved S-TuD-21 Sense sequence

<400> SEQUENCE: 37
taggaucauc aacatcaguc ggauaagcua caaguautcu ggt    43

<210> SEQ ID NO 38
<211> LENGTH: 43
<212> TYPE: DNA
<213> ORGANISM: artificial sequence
<220> FEATURE:
<223> OTHER INFORMATION: Improved S-TuD-21 Antisense sequence

<400> SEQUENCE: 38
accagaatac aacatcaguc ggauaagcua caagatgatc cua    43

<210> SEQ ID NO 39
<211> LENGTH: 43
<212> TYPE: DNA
<213> ORGANISM: artificial sequence
<220> FEATURE:
<223> OTHER INFORMATION: Improved S-TuD-21 Sense sequence (BNA)
<220> FEATURE:
<221> NAME/KEY: BNANC(NMe)
<222> LOCATION: (1)..(1)
<220> FEATURE:
<221> NAME/KEY: 2'-OMe
<222> LOCATION: (2)..(14)
<220> FEATURE:
<221> NAME/KEY: BNANC(NMe)
<222> LOCATION: (15)..(15)
<220> FEATURE:
<221> NAME/KEY: 2'-OMe
<222> LOCATION: (16)..(17)
<220> FEATURE:
<221> NAME/KEY: BNANC(NMe)
<222> LOCATION: (18)..(18)
<220> FEATURE:
<221> NAME/KEY: 2'-OMe
<222> LOCATION: (19)..(37)
<220> FEATURE:
<221> NAME/KEY: BNANC(NMe)
<222> LOCATION: (38)..(38)
<220> FEATURE:
<221> NAME/KEY: 2'-OMe
<222> LOCATION: (39)..(42)
<220> FEATURE:
<221> NAME/KEY: BNANC(NMe)
<222> LOCATION: (43)..(43)

<400> SEQUENCE: 39
taggaucauc aacatcaguc ggauaagcua caaguautcu ggt    43

<210> SEQ ID NO 40
<211> LENGTH: 43
<212> TYPE: DNA
<213> ORGANISM: artificial sequence
<220> FEATURE:
<223> OTHER INFORMATION: Improved S-TuD-21 Antisense sequence (BNA)
<220> FEATURE:
<221> NAME/KEY: 2'-OMe
<222> LOCATION: (1)..(7)
<220> FEATURE:
<221> NAME/KEY: BNANC(NMe)
<222> LOCATION: (8)..(8)
<220> FEATURE:

```
<221> NAME/KEY: 2'-OMe
<222> LOCATION: (9)..(14)
<220> FEATURE:
<221> NAME/KEY: BNANC(NMe)
<222> LOCATION: (15)..(15)
<220> FEATURE:
<221> NAME/KEY: 2'-OMe
<222> LOCATION: (16)..(17)
<220> FEATURE:
<221> NAME/KEY: BNANC(NMe)
<222> LOCATION: (18)..(18)
<220> FEATURE:
<221> NAME/KEY: 2'-OMe
<222> LOCATION: (19)..(35)
<220> FEATURE:
<221> NAME/KEY: BNANC(NMe)
<222> LOCATION: (36)..(36)
<220> FEATURE:
<221> NAME/KEY: 2'-OMe
<222> LOCATION: (37)..(38)
<220> FEATURE:
<221> NAME/KEY: BNANC(NMe)
<222> LOCATION: (39)..(39)
<220> FEATURE:
<221> NAME/KEY: 2'-OMe
<222> LOCATION: (40)..(43)

<400> SEQUENCE: 40
accagaatac aacatcaguc ggauaagcua caagatgatc cua          43

<210> SEQ ID NO 41
<211> LENGTH: 22
<212> TYPE: DNA
<213> ORGANISM: Homo sapiens

<400> SEQUENCE: 41
uagcuuauca gacugauguu ga                                 22

<210> SEQ ID NO 42
<211> LENGTH: 12
<212> TYPE: DNA
<213> ORGANISM: Artificial Sequence
<220> FEATURE:
<223> OTHER INFORMATION: Synthetic sequence
<220> FEATURE:
<221> NAME/KEY: modified_base
<222> LOCATION: (3)...(4)
<223> OTHER INFORMATION: loop
<220> FEATURE:
<221> NAME/KEY: modified_base
<222> LOCATION: (6)...(7)
<223> OTHER INFORMATION: loop
<220> FEATURE:
<221> NAME/KEY: modified_base
<222> LOCATION: (9)...(10)
<223> OTHER INFORMATION: loop

<400> SEQUENCE: 42
gggggggggg gg                                            12
```